United States Patent
Fischer et al.

(10) Patent No.: US 12,370,158 B2
(45) Date of Patent: *Jul. 29, 2025

(54) ANALOGS OF CYP-EICOSANOIDS FOR USE IN TREATING OR PREVENTING A DISORDER ASSOCIATED WITH NEOVASCULARIZATION AND/OR INFLAMMATION

(71) Applicants: OMEICOS Therapeutics GmbH, Berlin (DE); Max Delbrück-Centrum für Molekulare Medizin, Berlin (DE)

(72) Inventors: Robert Fischer, Berlin (DE); Wolf-Hagen Schunck, Berlin (DE); Dominik Müller, Berlin (DE); Tim Wesser, Berlin (DE); Anne Konkel, Berlin (DE); Janine Lossie, Berlin (DE)

(73) Assignees: OMEICOS Therapeutics GmbH, Berlin (DE); Max Delbrück-Centrum Für Molekulare Medizin, Berlin (DE)

( * ) Notice: Subject to any disclaimer, the term of this patent is extended or adjusted under 35 U.S.C. 154(b) by 93 days.

This patent is subject to a terminal disclaimer.

(21) Appl. No.: 17/383,131

(22) Filed: Jul. 22, 2021

(65) Prior Publication Data

US 2021/0353569 A1  Nov. 18, 2021

Related U.S. Application Data

(63) Continuation of application No. 16/089,461, filed as application No. PCT/EP2017/057830 on Apr. 3, 2017, now abandoned.

(60) Provisional application No. 62/317,253, filed on Apr. 1, 2016.

(30) Foreign Application Priority Data

Jan. 26, 2017  (EP) .................................... 17153412

(51) Int. Cl.
| | | |
|---|---|---|
| A61K 31/192 | (2006.01) | |
| A61K 31/165 | (2006.01) | |
| A61K 31/22 | (2006.01) | |
| A61K 31/341 | (2006.01) | |
| A61K 31/351 | (2006.01) | |
| A61K 31/40 | (2006.01) | |
| A61K 31/4196 | (2006.01) | |
| A61K 31/421 | (2006.01) | |
| A61K 31/5375 | (2006.01) | |
| A61P 27/02 | (2006.01) | |
| A61P 29/00 | (2006.01) | |

(52) U.S. Cl.
CPC .......... *A61K 31/165* (2013.01); *A61K 31/192* (2013.01); *A61K 31/22* (2013.01); *A61K 31/341* (2013.01); *A61K 31/351* (2013.01); *A61K 31/40* (2013.01); *A61K 31/4196* (2013.01); *A61K 31/421* (2013.01); *A61K 31/5375* (2013.01); *A61P 27/02* (2018.01); *A61P 29/00* (2018.01)

(58) Field of Classification Search
CPC .................................................... A61K 31/192
See application file for complete search history.

(56) References Cited

FOREIGN PATENT DOCUMENTS

| | | |
|---|---|---|
| KR | 10-2071813 | 1/2020 |
| RU | 2545675 | 4/2015 |
| WO | 2010/081683 A1 | 7/2010 |
| WO | 2010/106571 A1 | 9/2010 |
| WO | 2012/138706 A1 | 10/2012 |
| WO | 2015/110262 A1 | 7/2015 |
| WO | 2017/013265 A1 | 1/2017 |

OTHER PUBLICATIONS

Lambert et al. Nature Protocols vol. 8, pp. 2197-2211 (2013).*
The International Search Report (ISR) with Written Opinion for PCT/EP2017/057830 dated May 16, 2017, pp. 1-13.
Second Written Opinion of the International Preliminary Examining Authority for PCT/EP2017/057830 dated Mar. 8, 2018, pp. 1-6.
The International Preliminary Report on Patentability (IPRP) for PCT/EP2017/057830 dated Jun. 15, 2018, pp. 1-44.
Kharkevitch, D.A., Pharmacology, 10th ed. M.: Geotar-Media, 2010, p. 7374.
Belikov V.G., Pharmaceutical Chemistry, Chapter 2.2 "Relationship between the structure of a molecule and its effect over an organism".- M.: Vyshchaya Schkola, 1993, p. 43-47.
Dyson G, May P. "Chemistry of synthetic drugs", translation from English—M.: MIR, 1964, pp. 12-19.
Yanai R., et al. "Cytochrome P450-generated metabolites derived from omega-3 fatty acids attenuate neovascularization", PNAS, [Online] vol. 111, No. 26, Jul. 1, 2014 (Jul. 1, 2014), pp. 9603-9608, retrieved from the Internet: URL:www.pnas.org/cgi/doi/10.1073/pnas.1401191111.
Falck et al., "14, 15-Epoxyeicosa-5,8,11-trienoic Acid (14,15-EET) Surrogates Containing Epoxide Bioisosteres: Influence upon Vascular Relaxation and Soluble Epoxide Hydrolase Inhibition", Journal of Medicinal Chemistry, 2009, vol. 52, 5069-5075.
Zhulenko V.N., Gorshkov G.I. "Pharmacology". M.:KolosS, 2008, p. 34-35.

* cited by examiner

*Primary Examiner* — Brian E McDowell
(74) *Attorney, Agent, or Firm* — McDonnell Boehnen Hulbert & Berghoff LLP

(57) ABSTRACT

The present invention relates to compounds according to general formula (I) which are metabolically robust analogues of bioactive lipid mediators derived from omega-3 polyunsaturated fatty acids (n-3 PUFAs) for use in treating or reducing the risk of developing or preventing: (i) neovascularization and/or (ii) inflammatory disorder, in particular, ophthalmic disorders associated with neovascularization and/or inflammation.

5 Claims, 5 Drawing Sheets

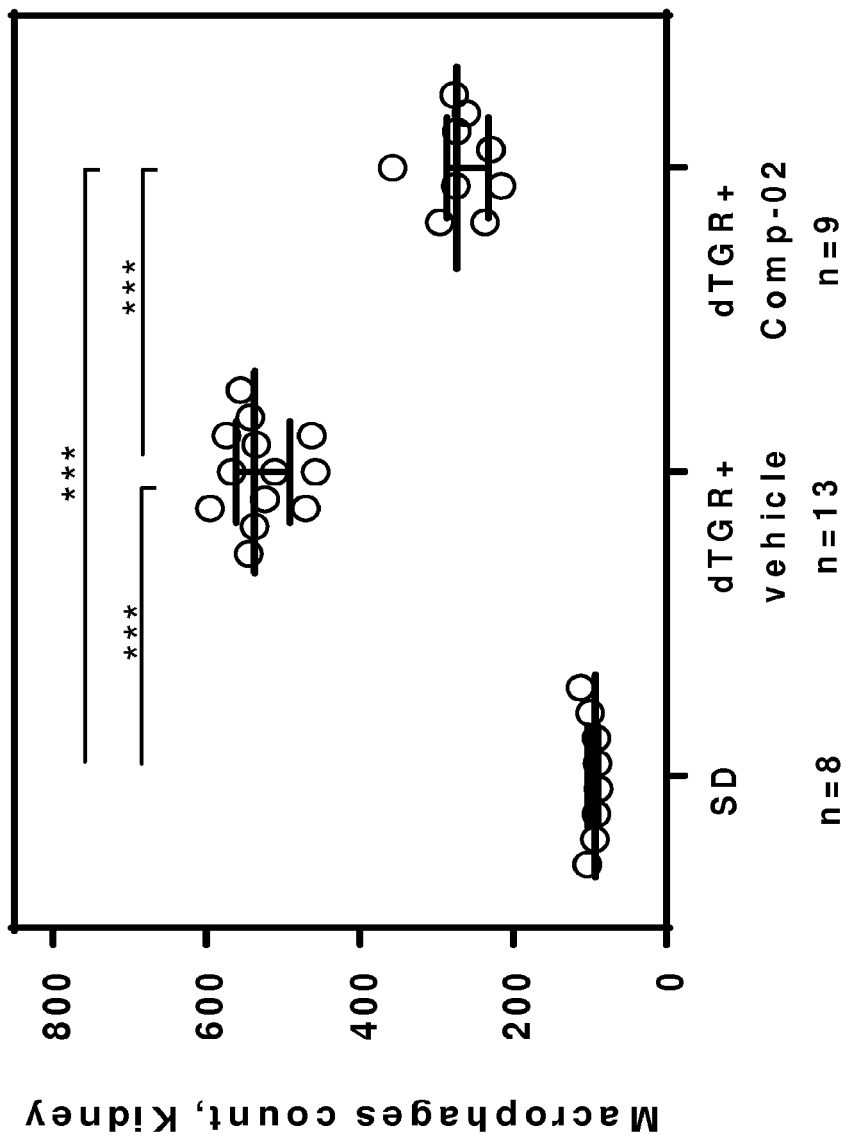

Figure 1:
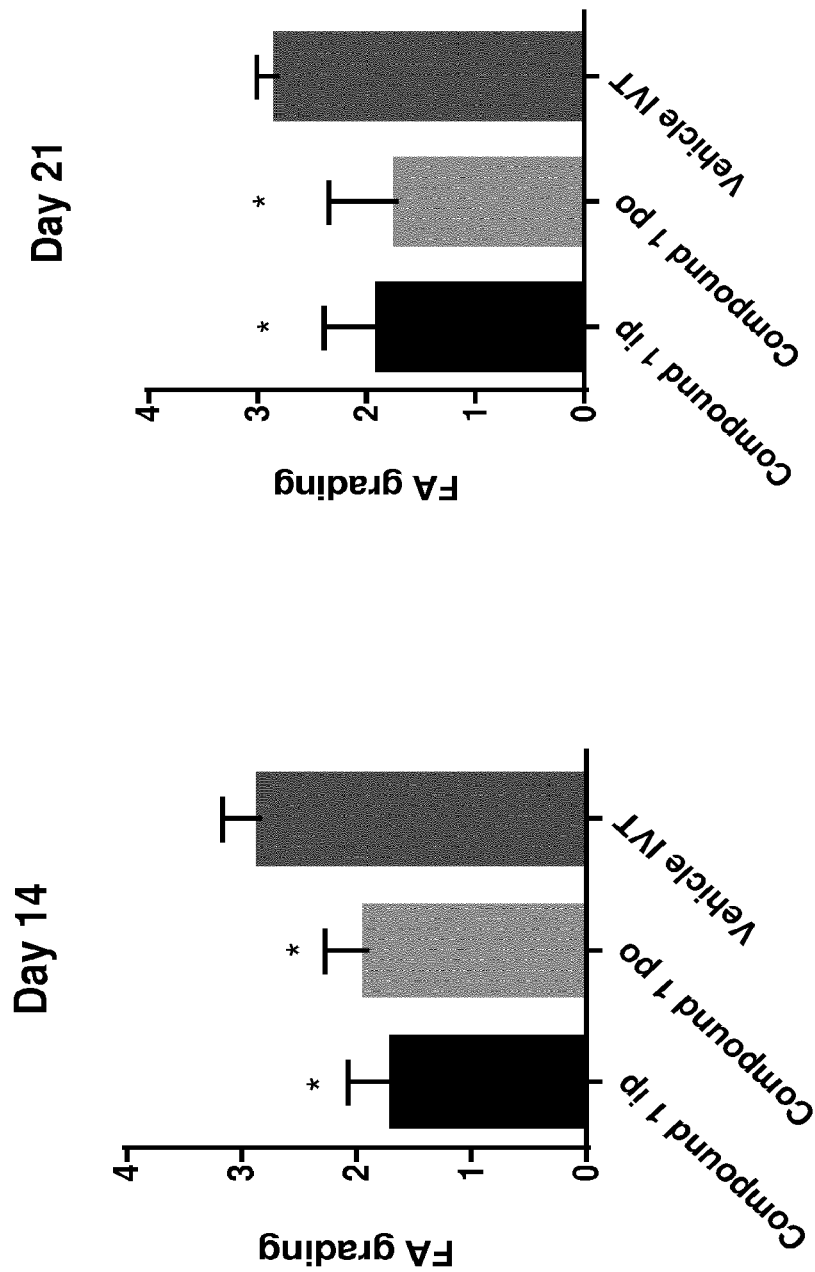

ANALOGS OF CYP-EICOSANOIDS FOR USE IN TREATING OR PREVENTING A DISORDER ASSOCIATED WITH NEOVASCULARIZATION AND/OR INFLAMMATION

CROSS-REFERENCE TO RELATED APPLICATION

This application is a continuation of U.S. patent application Ser. No. 16/089,461, filed Sep. 28, 2018, which is a U.S. national phase of International Application No. PCT/EP2017/057830, filed Apr. 3, 2017, which claims priority to European Patent Application No. 17153412.6, filed Jan. 26, 2017 and U.S. Provisional Application No. 62/317,253 filed Apr. 1, 2016, the contents of all of which are incorporated by reference herein in their entirety.

The present invention relates to compounds according to general formula (I) which are metabolically robust analogues of bioactive lipid mediators derived from omega-3 polyunsaturated fatty acids (n-3 PUFAs) for use in treating or reducing the risk of developing or preventing: (i) neovascularization and/or (ii) inflammatory disorder, in particular, ophthalmic disorders associated with neovascularization and/or inflammation.

BACKGROUND OF THE INVENTION

Omega-6 and omega-3 polyunsaturated fatty acids (n-6 and n-3 PUFAs) are essential components of the mammalian diet. Biologically most important n-3 PUFAs are eicosapentaenoic acid (EPA, 20:5 n-3) and docosahexaenoic acid (DHA, 22:6 n-3). Dietary n-3 PUFAs have effects on diverse physiological processes impacting normal health and chronic disease, such as the regulation of plasma lipid levels, cardiovascular and immune function, inflammation, insulin action, and neuronal development and visual function.

Ingestion of n-3 PUFA will lead to their distribution to virtually every cell in the body with effects on membrane composition and function, eicosanoid synthesis, and signaling as well as the regulation of gene expression.

Epidemiological and experimental studies showed that n-3 PUFA consumption is associated with a reduced risk of macular degeneration. A major common mechanism in protecting against macular degeneration and cancer consists in the capacity of n-3 PUFAs to inhibit pathological angiogenesis. EPA and DHA inhibit abnormal retinal neovascularization, vascular permeability, and inflammation. Angiogenesis is an essential step in tumor growth and metastasis that is promoted by n-6 PUFAs and n-6 PUFA-derived metabolites but inhibited by n-3 PUFAs and n-3 PUFA-derived metabolites.

Simopoulos and colleagues summarized animal experiments and clinical intervention studies indicating that n-3-PUFAs have anti-inflammatory properties and, therefore, might be useful in the management of inflammatory and autoimmune diseases (Simopoulos A P. Omega-3 fatty acids in inflammation and autoimmune diseases. J Am. Coll. NutL 2L 495-505 (2002)). Among the n-3-PUFAs, EPA and DHA play an important and potent role with regard to anti-inflammatory effects. (Calder C. P., Marine omega-3 fatty acids and inflammatory processes: Effects, mechanisms and clinical relevance, Biochimica et Biophsica Acta—Molecular and Cell Biology of Lipids, Volume 1851 (4), April 2015, 469-484).

Koto and colleagues showed that EPA has anti-inflammatory activity in a mouse model for choroidal neovascularization (CNV) (Koto et al. Eicosapentaenoic Acid Is Anti-Inflammatory in Preventing Choroidal Neovascularization in Mice. Invest Ophthalmol Vis Sci. 2007; 48:4328-4334). They demonstrated that an EPA-rich diet results in significant suppression of CNV-related inflammatory molecules in vivo and in vitro such as ICAM-1 and MCP-1 in endothelial cells and VEGF and IL-6 in macrophages. Yanai and colleagues demonstrated that dietary enrichment with n-3 PUFAs suppresses choroidal neovascularization in a mouse model of age-related macular degeneration (AMD) (Yanai et al. Cytochrome P450-generated metabolites derived from ω-3 fatty acids attenuate neovascularization. Proc Natl Acad Sci USA. 2014 Jul. 1; 111(26):9603-8.). Furthermore, they have shown that n-3 PUFAs have anti-inflammatory properties in this model. This has been shown by significantly reduced systemic immune-cell recruitment and down regulation of Icam-1 and E-selectin expression on endothelial cells and the ICAM-1 ligand CD11b-CD18 on the surface of circulating leukocytes. N-3 PUFAs result also in suppression of macrophage invasion into CNV lesions. They have further shown that this effect is mediated by CYP-generated bioactive lipid mediators derived from ω-3 LCPUFAs, specifically by the major CYP epoxygenase metabolites derived from EPA (17,18-EEQ) and DHA (19, 20-EDP) (Yanai et al. Cytochrome P450-generated metabolites derived from ω-3 fatty acids attenuate neovascularization Proc Natl Acad Sci USA. 2014 Jul. 1; 111(26):9603-8 and WO 2014/110261 A1).

Laser induced CNV model in mice is a widely accepted model for testing potential drugs for their effectiveness in treating ophthalmic disorders associated with neovascularization and/or inflammation, in particular AMD. Furthermore, ocular neovascular diseases such as AMD are also suspected to have a significant inflammatory component (Lopez et al. Pathologic features of surgically excised subretinal neovascular membranes in age-related macular degeneration. Am J Ophthalmol. 1991; 112(6):647-656.; Grossniklaus et al. Macrophage and retinal pigment epithelium expression of angiogenic cytokines in choroidal neovascularization. Mol Vis. 2002 Apr. 21; 8:119-26; Lopez et al. Transdifferentiated retinal pigment epithelial cells are immunoreactive for vascular endothelial growth factor in surgically excised age-related macular degeneration-related choroidal neovascular membranes. Invest Ophthalmol Vis Sci. 1996, 37(5):855-868; Tezel et al. Pathogenesis of age-related macular degeneration. Trends Mol Med. 2004; 10(9): 417-420.; Schlingemann R O—Role of growth factors and the wound healing response in age-related macular degeneration. Graefes Arch Clin Exp Ophthalmol. 2004; 242(1): 91-101). Grossniklaus and colleagues have shown in choroidal membrane specimen from AMD patients that progression of CNV represents a dynamic process with not only angiogenesis but also with a strong inflammatory component in particular macrophages. Based on the work by Ambati and colleagues (Ambati et al. An animal model of age-related macular degeneration in senescent Ccl-2- or Ccr-2-deficient mice. Nat. Med. 2003, 9, 1390-1397) linking AMD pathogenesis to complement system and macrophages the inflammatory component of AMD was further deciphered and changed the understanding of AMD pathogenesis dramatically. Afterwards many research groups further explored the role of inflammatory processes in AMD and CNV pathogenesis such as recent work analyzed the macrophage polarization in experimental and clinical choroidal neovascularization (Yang et al. Macrophage polarization in experimental and clinical choroidal neovascularization. Sci Rep., 2016 Aug. 4, 6:30933). Recent reviews by the group of David Hinton, a pioneer of CNV research, and Campa et al. (Inflammatory mediators and angiogenic factors in choroidal neovascularization: pathogenetic interactions and therapeutic implications. Mediators of Inflammation, 2010) nicely summarizes the impact of inflammation in AMD pathogenesis and resulting fibrosis (Ishikawa et al. Molecular mechanisms of subretinal fibrosis in age-related macular degeneration. Exp Eye Res. 2016 January, 142:19-252016) and concluding CNV causing a heterogeneous disease affecting the posterior segment of the eye which is more properly definable as an aberrant tissue invasion of endothelial and inflammatory cells, in which both angiogenesis and inflammation are involved.

It becomes obvious that the laser-induced CNV model which is widely used to elucidate the pathobiology of choroidal angiogenesis and to identify novel therapeutic applications (Grossniklaus et al. 2010) has a strong inflammatory stimulus due to the injury after laser burn of Bruch's membrane. Therefore, beside anti-angiogenic compounds, many anti-inflammatory compounds showed broad activity and the model can be also considered as a model for ocular inflammation and treatment response and a model of ocular inflammation would be considered by the skilled person to be evidence of the suitability of a compound in the treatment of inflammation as such.

During inflammation, circulating monocytes increasingly leave the circulation and migrate into tissues where, following conditioning by local growth factors, pro-inflammatory cytokines and microbial products, they differentiate into macrophage or dendritic cell populations. In the rat model shown in Example 5, this event is visible by staining the infiltrated ED1-positive monocytes/macrophages in heart and kidney slices with a respective antibody. In general, recruitment of monocytes is essential for effective control and clearance of viral, bacterial, fungal and protozoal infections, but recruited monocytes also contribute to the pathogenesis of inflammatory and degenerative diseases (Shi C., et al., Monocyte recruitment during infection and inflammation. Nat Rev Immunol. 2011 Oct. 10; 11 (11) 762-74). Beyond promoting atheroclerosis, recruited monocytes/macrophages are known to contribute to acute and chronic inflammatory diseases of the heart and kidney (Ingersoll et al., Monocyte trafficking in acute and chronic inflammation. Trends Immuno 2011 October 32 (10) 470-7; Hansson G., Inflammation, Atherosclerosis, and Coronary Artery Disease. New Engl Jour Med 2005, (352) 1685-95; Kinsey et al, Inflammation in Acute Kidney Injury. Experim Nephro 2008, (109) e102-e107; Bonventre, J. Cellular pathophysiology of ischemic acute kidney injury. J Clinic Invest 2011 November, (121) 4210-4221; Guiteras R., et al., Macrophage in chronic kidney disease. Cli Kid j 2016, vol. 9, no 6, 765-771).

The production of TNF-alpha plays an important role in chronic inflammatory conditions, intemediary metabolism and cardiovascular risk (Popa C. et al., The role of TNF-alpha in chronic inflammatory conditions, intermediary metabolism, and cardiovascular risk. J Lipid Res 2007, (48) 752-761). Aberrant TNF-alpha production and TNF receptor signaling have been associated with the pathogenesis of several chronic inflammatory diseases (Parameswaran N. et al., Tumor Necrosis Factor-α Signaling in Macrophages. Crit Rev Eukaryot Gene Expr 2010 20 (2) 87-103). TNF-alpha has both diverse and potentially conflicting roles in cardiac function and pathology (Sack M., Tumor necrosis factor-alpha in cardiovascular biology and the potential role for anti-tumor necrosis factor-alpha therapy in heart disease. Pharmacol Ther 2002 April-May, 94 (1-2) 123-135). As also shown in Example 4, TNF-alpha can be produced in response to pro-inflammatory stimuli by cardiomyocytes themselves. After release into the surrounding tissue, TNF-alpha together with a wide range of further mediators triggers leucocyte activation and recruitment (Ghigo A. et al., Myocyte signalling in leucocyte recruitment to the heart. Cardicovasc Res 2014 May. 102 (2) 270-280).

One of the PUFAs most important biological roles is to supply precursors for the production of bioactive fatty acid metabolites that can modulate many functions. For instance, arachidonic acid (AA; 20:4, n-6) is metabolized by Cytochrome P450 (CYP) enzymes to several classes of oxygenated metabolites with potent biological activities. Major metabolites include 20-hydroxyeicosatetraenoic acid (20-HETE) and a series of regio- and stereoisomeric epoxyeicosatrienoic acids (EETs). CYP4A and CYP4F isoforms produce 20-HETE and CYP2C and CYP2J isoforms EETs.

It is known that EPA (20:5, n-3) and DHA (22:6, n-3) may serve as alternative substrates for AA-metabolizing CYP isoforms (Arnold C. et al., J Biol Chem. 2010 Oct. 22; 285(43):32720-33.; Fischer R. et al., J Lipid Res. 2014 Mar. 16; 55(6):1150-1164.). CYP2C and CYP2J subfamily members that epoxidize AA to EETs, metabolize EPA to epoxyeicosatetraenoic acids (EEQs), and DHA to epoxydocosapentaenoic acids (EDPs). The ω-3 double bond distinguishing EPA and DHA from AA is the preferred site of attack by most of the epoxygenases resulting in the formation of 17,18-EEQ and 19,20-EDP as main metabolites. CYP4A and CYP4F isoforms, hydroxylating AA to 20-HETE, metabolize EPA to 20-hydroxyeicosapentaenoic acid (20-HEPE) and DHA to 22-hydroxydocosahexaenoic acid (22-HDHA). CYP1A1, CYP2E1 and other isoforms converting AA predominantly to 19-HETE show pronounced ω-3 epoxygenase activities with EPA and DHA. Human CYP1A1 variants lead to differential eicosapentaenoic acid metabolite patterns. Cytochrome P450-dependent eicosapentaenoic acid metabolites are novel BK channel activators. A remarkable feature of CYP-dependent n-3 PUFA metabolism is the preferred epoxidation of the n-3 double bond, which distinguishes EPA and DHA from AA. The resulting metabolites—17,18-EEQ from EPA and 19,20-EDP from DHA—are unique in having no homolog within the series of AA products. In line with the substrate specificity of the CYP isoforms, dietary EPA/DHA supplementation causes a profound shift from AA- to EPA- and DHA-derived epoxy- and w-hydroxy-metabolites in all major organs and tissues of the rat and presumably also in human.

EETs and 20-HETE play important roles in the regulation of various cardiovascular functions (Roman R J., *Physiol Rev.* 2002; 82:131-85). It has been shown that Ang II-induced hypertension is associated with a down-regulation of CYP-dependent AA metabolism (Kaergel et I., *Hypertension.* 2002; 40:273-9) in a double-transgenic rat (dTGR) model of Ang II-induced hypertension and end-organ damage (Luft et al., *Hypertension.* 1999; 33:212-8). The transgenic rats harbor the human renin and angiotensinogen genes, produce Ang II locally and develop significant hypertension, myocardial infarction and albuminuria. The animals die of myocardial and renal failure before the eighth week of age. The model shows severe features of Ang II-induced inflammation. Reactive oxygen species are generated, the transcription factors NF-κB and AP-1 are activated, and genes harboring binding sites for these transcription factors are activated.

Recently, it has been shown that eicosapentaenoic acid (EPA) supplementation significantly reduced the mortality of dTGR (Theuer et al., Kidney Int. 2005; 67:248-58). Additionally, it has been shown that dTGR develop ventricular arrhythmias based on Ang II-induced electrical remodeling (Fischer et sl. *Am J Physiol Heart Circ Physiol.* 2007; 293:H1242-1253). Treatment of the dTGR rats with a PPAR-alpha activator strongly induced CYP2C23-dependent EET production and protected against hypertension and end-organ damage (Muller et al., *Am J Pathol.* 2004; 164: 521-32).

Long-term feeding of dTGR (from week 4 to 7 of age) with a mixture of pure EPA- and DHA-ethyl esters (Omacor from Solvay Arzneimittel, Hannover, Germany) improved the electrical remodeling of the heart in this model of angiotensin II-induced hypertension. In particular, EPA and DHA reduced the mortality, suppressed the inducibility of cardiac arrhythmias and protected against connexin 43-gap junctional remodeling (Fischer et al., Hypertension. 2008 February; 51(2):540-6). In general, CYP-dependent eicosanoids have to be considered as second messengers: EETs and 20-HETE are produced by CYP enzymes after extracellular signal induced release of AA from membrane phospholipids (by phospholipase A2) and exert their function in the context of signaling pathways modulating ion transport, cell proliferation and inflammation. Depending on the diet, n-3 PUFAs partially replace AA at the sn2-position of phospholipids and may thus become involved as alternative molecules in the subsequent signaling pathways.

The few studies on the biological activities of CYP-dependent eicosanoids in the heart indicate important roles for EETs and 20-HETE in the regulation of L-type $Ca^{2+}$ and sarcolemmal and mitochondrial ATP-sensitive potassium ($K_{ATP}$) channels. In cardiac myocytes, L-type $Ca^{2+}$ currents and cell shorting are reduced upon inhibition of EET generation and these effects can be reversed by adding 11,12-EET (Xiao et al., *J Physiol.* 1998; 508 (Pt 3):777-92). EETs were also shown to activate cardiac $K_{ATP}$ channels. This effect is highly stereoselective: only the S,R but not the R,S-enantiomer of 11,12-EET was effective (Lu et al., *Mol Pharrmacol.* 2002; 62:1076-83). Overexpression of the EET-generating human CYP2J2 resulted in an improved postischemic functional recovery of the transgenic mouse heart via activation of $K_{ATP}$ channels (Seubert et al., *Circ Res.* 2004; 95:506-14). 20-HETE appears to play an opposite role by acting as an endogenous $K_{ATP}$ channel blocker (Gross et al., *J Mol Cell Cardiol.* 2004; 37:1245-9; Nithipatikom et al., *Circ Res.* 2004; 95:e65-71).

Although n-3 PUFA-derived CYP metabolites, such as 17,18-EEQ and 19,20-EDP, play important roles in mediating the beneficial effects of n-3 PUFAs in the mammalian body, they are not used as therapeutics due to their limited bioavailability as well as chemical and metabolic instability. These epoxymetabolites of n-3 PUFAs are prone to autoxidation, rapid inactivation by the soluble epoxide hydrolase, and degradation by 3-oxidation.

Therefore, the problem underlying the present invention is to provide improved analogues of n-3 PUFA metabolites for treating or reducing the risk of developing or preventing disorders associated with neovascularization and/or inflammation, in particular ophthalmic disorders associated with neovascularization and/or inflammation.

In a first aspect the above problem is solved by the provision of compounds of the general formula (I):

P-E-I  (I)

or a pharmaceutically acceptable salt thereof, wherein

P is a group represented by the general formula (II):

wherein n is 0 or an integer of from 3 to 8, i.e. 3, 4, 5, 6, 7, or 8, preferably 3; and k is 0, 1, or 2; preferably with the proviso that when n is 0 k is 1, most preferably k is 1;

X represents $CH_2OH$, $CH_2OAc$, $CH(O)$ or a group selected from the group consisting of:

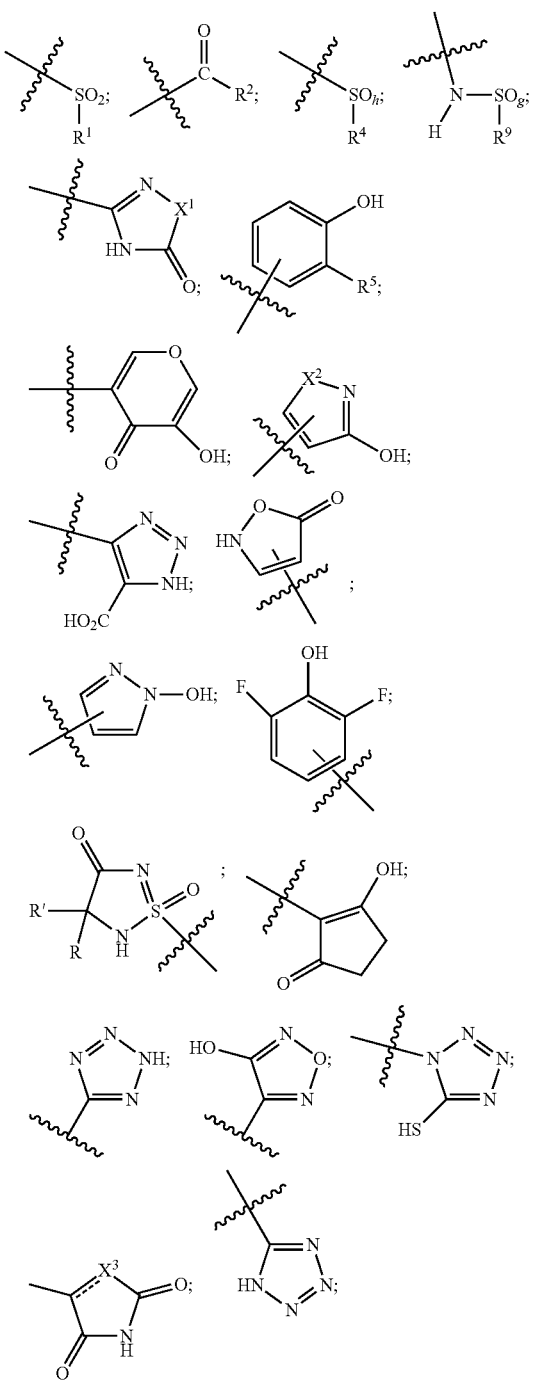

-continued

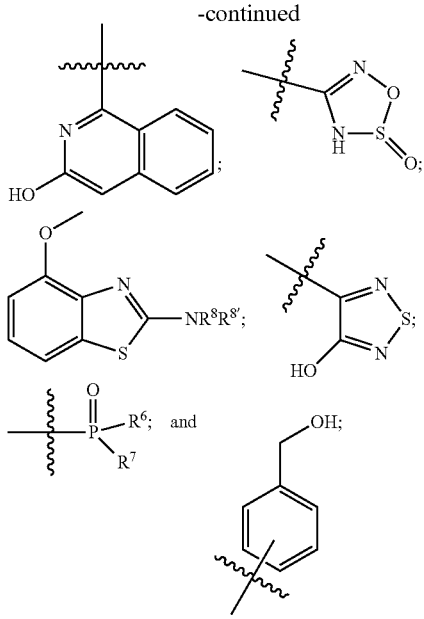

preferably X is

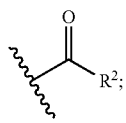

wherein
R and R' each independently represents a hydrogen atom; or a $C_1$-$C_6$alkyl group which may be substituted with one or more fluorine or chlorine atom(s) or hydroxyl group(s);

$R^1$ represents a hydroxyl group, $C_1$-$C_6$alkoxy, —NHCN, —NH($C_1$-$C_6$alkyl), —NH($C_3$-$C_6$cycloalkyl), —NH(aryl), or —O($C_1$-$C_6$alkyldiyl)O(C=O)$R^{11}$; $R^{11}$ is a $C_1$-$C_6$alkyl group which is optionally substituted with one or more fluorine or chlorine atom(s); or a $C_3$-$C_6$cycloalkyl group which is optionally substituted with one or more fluorine or chlorine atom(s) or hydroxyl group(s);

$R^2$ represents —$NHR^3$; —$NR^{20}R^{21}$; —$OR^{22}$; —$(OCH_2—CH_2)_i$—$R^{23}$; —$C_3$-$C_{10}$-heterocyclyl optionally substituted with one, two or three substituents independently selected from the group consisting of hydroxyl group, $C_1$-$C_6$alkoxy, $C_1$-$C_6$alkyl, and oxo; -$(Xaa)_o$; a mono-, or disaccharide, or a derivative thereof, which is joined to —C(O) by an ester bond via the 1-O-, 3-O-, or 6-O-position of the saccharide; or is selected from the group consisting of:

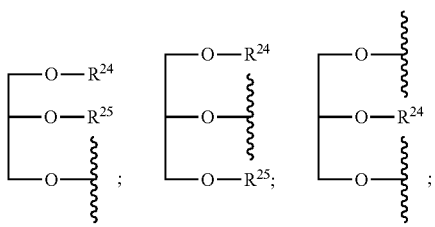

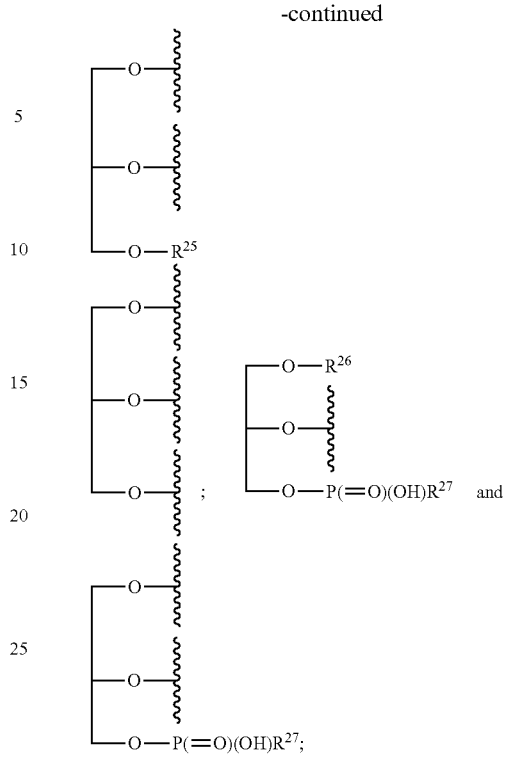

wherein
$R^3$ represents $(SO_2R^{30})$; $(OR^{31})$; —$C_1$-$C_6$alkanediyl$(SO_2R^{32})$; —$C_1$-$C_6$alkanediyl$(CO_2H)$, an aryl group, a heteroaryl group, a cycloalkyl group or a heterocycloalkyl group, wherein the aryl group is optionally substituted with one, two or three substituents independently selected from the group consisting of $C_1$-$C_6$alkyl, $C_1$-$C_6$alkoxy, $C_1$-$C_6$alkylthio, fluorine or chlorine atom, hydroxyl group, amino group, —NH($C_1$-$C_6$alkyl), —N($C_1$-$C_6$)dialkyl, and —C(=O)$OR^{51}$; wherein the heteroaryl group, is optionally substituted with one, two or three substituents independently selected from the group consisting of $C_1$-$C_6$alkyl, $C_1$-$C_6$alkoxy, $C_1$-$C_6$alkylthio, fluorine or chlorine atom, hydroxyl group, amino group, —NH($C_1$-$C_6$alkyl), —N($C_1$-$C_6$)dialkyl and —C(=O)$OR^{51}$; where the cycloalkyl group is optionally substituted with one, two or three substituents independently selected from the group consisting of $C_1$-$C_6$alkyl, $C_1$-$C_6$alkoxy, $C_1$-$C_6$alkylthio, fluorine or chlorine atom, hydroxyl group, amino group, —NH($C_1$-$C_6$alkyl), —N($C_1$-$C_6$)dialkyl, and —C(=O)$OR^{51}$; and wherein the heterocycloalkyl group is optionally substituted with one, two or three substituents independently selected from the group consisting of $C_1$-$C_6$alkyl, $C_1$-$C_6$alkoxy, $C_1$-$C_6$alkylthio, fluorine or chlorine atom, hydroxyl group, amino group, —NH($C_1$-$C_6$alkyl), —N($C_1$-$C_6$)dialkyl and —C(=O)$OR^{51}$;

$R^{30}$ is a $C_1$-$C_6$alkyl, or an aryl group, wherein the $C_1$-$C_6$alkyl group is optionally substituted with —$NH_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, one, two or three fluorine or chlorine atoms, or a hydroxyl group; and wherein the aryl group is optionally substituted with one, two or three substituents independently selected from the group consisting of $C_1$-$C_6$alkyl, $C_1$-$C_6$alkoxy, $C_1$-$C_6$alkylthio, fluorine or chlorine atom, hydroxyl group, amino group, —NH($C_1$-$C_6$alkyl), and —N($C_1$-$C_6$)dialkyl;

$R^{31}$ is a $C_1$-$C_6$alkyl group which is optionally substituted with one or more fluorine or chlorine atom(s) or hydroxyl group(s); or a $C_3$-$C_6$cycloalkyl group which is optionally substituted with one or more fluorine or chlorine atom(s) or hydroxyl group(s);

$R^{32}$ is a $C_1$-$C_6$alkyl group which is optionally substituted with one or more fluorine or chlorine atom(s) or hydroxyl group(s); or a $C_3$-$C_6$cycloalkyl group which is optionally substituted with one or more fluorine or chlorine atom(s) or hydroxyl group(s);

$R^{20}$ and $R^{21}$ each independently represents a hydrogen atom; a $C_1$-$C_6$alkyl group which may be substituted with one or more fluorine or chlorine atom(s) or hydroxyl group(s); a $C_3$-$C_6$cycloalkyl group which may be substituted with one or more fluorine or chlorine atom(s) or hydroxyl group(s); —$C_1$-$C_6$alkyldiyl($CO_2H$) or together form a $C_3$-$C_{10}$-heterocycloalkyl which may be substituted with one or more $C_1$-$C_6$alkyl group(s), $C_1$-$C_6$alkoxy group(s), fluorine or chlorine atom(s) or hydroxyl group(s);

$R^{22}$ is a hydrogen atom, a $C_1$-$C_6$alkyl group; or a $C_3$-$C_6$cycloalkyl group; wherein the $C_1$-$C_6$alkyl group or the $C_3$-$C_6$cycloalkyl group is optionally substituted with —$NH_2$, —NH($C_1$-$C_6$)alkyl, —N($C_1$-$C_6$)dialkyl, —NH($C_1$-$C_6$)alkyldiyl-$C_1$-$C_6$alkoxy, one, two or three fluorine or chlorine atom(s), hydroxyl, or $C_1$-$C_6$alkoxy, an aralkyl group, a heteroalkyl group or a heteroalkylcycloalkyl group;

$R^{23}$ is —OH, —O($C_1$-$C_3$)alkyl, or —N($C_1$-$C_3$)dialkyl;

i is an integer of from 1 to 10;

$R^{24}$, $R^{25}$, and $R^{26}$ each independently represents a hydrogen atom; —C(=O)$C_{11}$-$C_{21}$alkyl; or —C(=O)$C_{11}$-$C_{21}$alkenyl;

$R^{27}$ represents —OH; —O($CH_2$)$_2$$NH_2$, —$OCH_2$—[CH($NH_2$)($CO_2H$)], —O($CH_2$)$_2$N($CH_3$)$_3$; or

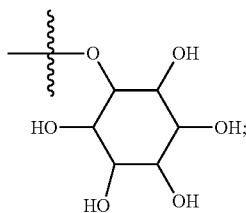 [SMILES: *OC1C(O)C(O)C(O)C(O)C1O]

Xaa represents Gly, a conventional D,L-, D- or L-amino acid, a non-conventional D,L-, D- or L-amino acid, or a 2- to 10-mer peptide; and is joined to —C(=O) by an amide bond;

o is an integer of from 1 to 10;

$R^4$ is selected from the group consisting of:

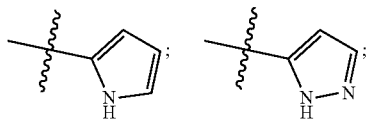

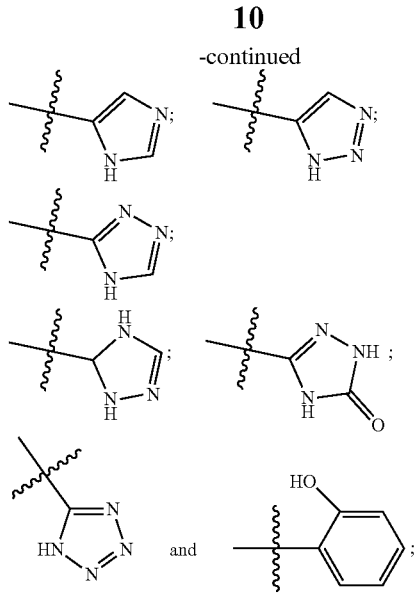

h is 0, 1, or 2;

$R^5$ represents a hydrogen atom; a fluorine or chlorine atom; —$CF_3$; —C(=O)$OR^{51}$; —NHC(=O)$R^{52}$; —C(=O)$NR^{53}R^{54}$; or —S($O_2$)OH;

$R^{51}$ represents a hydrogen atom; a $C_1$-$C_6$alkyl group; or a $C_3$-$C_6$cycloalkyl group; wherein the $C_1$-$C_6$alkyl group or the $C_3$-$C_6$cycloalkyl group is optionally substituted with —$NH_2$, —NH($C_1$-$C_6$)alkyl, —N($C_1$-$C_6$)dialkyl, —NH($C_1$-$C_6$)alkyldiyl-$C_1$-$C_6$alkoxy, one, two or three fluorine or chlorine atom(s), hydroxyl, or $C_1$-$C_6$alkoxy;

$R^{52}$, $R^{53}$ and $R^{54}$ each independently represents a $C_1$-$C_6$alkyl group which is optionally substituted with one or more fluorine or chlorine atom(s); a $C_3$-$C_6$cycloalkyl group which is optionally substituted with one or more fluorine or chlorine atom(s); or an aryl group which is optionally substituted with one, two or three substituents independently selected from the group consisting of $C_1$-$C_6$alkyl, $C_1$-$C_6$haloalkyl, $C_1$-$C_6$alkoxy, $C_1$-$C_6$alkylthio, fluorine or chlorine atom, hydroxyl group, amino group, —NH($C_1$-$C_6$alkyl), —N($C_1$-$C_6$)dialkyl, and an oxo substituent;

$R^6$ and $R^7$ each independently represents a hydroxyl group; an —O($C_1$-$C_6$)alkyl group, an —O($C_2$-$C_6$)alkenyl group, a, —O($C_1$-$C_6$)alkyldiylO(C=O)($C_1$-$C_6$) alkyl group, or a —O($C_1$-$C_6$)alkyldiylO(C=O)($C_2$-$C_6$) alkenyl group; wherein the $C_1$-$C_6$alkyl group and the $C_2$-$C_6$alkenyl group may be substituted with $NH_2$, —NH($C_1$-$C_6$)alkyl, —N($C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$ alkylaminocarbonyl-, di($C_1$-$C_6$)alkylaminocarbonyl-, or one, two or three fluorine or chlorine atom(s); or $R^6$ represents a hydroxyl group and $R^7$ represents a group:

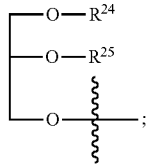

$R^9$ represents $C_1$-$C_6$alkyl, or aryl; wherein the $C_1$-$C_6$alkyl is optionally substituted with —$NH_2$, —$NH(C_1$-$C_6)$alkyl, —$N(C_1$-$C_6)$dialkyl, —$NH(C_1$-$C_6)$alkyldiyl-$C_1$-$C_6$alkoxy, one, two or three fluorine or chlorine atom(s), hydroxy, $C_1$-$C_6$alkoxy, aryl, aryloxy, —C(=O)-aryl, —C(=O)$C_1$-$C_6$alkoxy; and wherein the aryl group is optionally substituted with one, two or three substituents independently selected from the group consisting of $C_1$-$C_6$alkyl, $C_1$-$C_6$alkoxy, $C_1$-$C_6$alkylthio, fluorine or chlorine atom, hydroxyl group, amino group, —$NH(C_1$-$C_6$alkyl), —$N(C_1$-$C_6)$dialkyl, and an oxo substituent;

g is 1 or 2, preferably 2;

$X^1$ represents an oxygen atom; sulfur atom; or NH;

$X^2$ represents an oxygen atom; sulfur atom; NH; or $N(CH_3)$;

$X^3$ represents an oxygen atom; sulfur atom; nitrogen atom; carbon atom; or C—OH; and the dashed line represents a carbon-carbon bond or a carbon-carbon double bond;

E is a group represented by the general formula (III) or (IV):

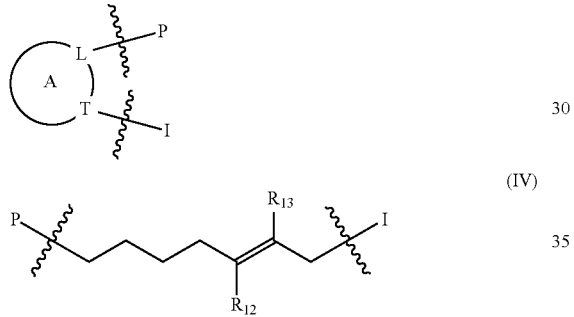

wherein R12 and R13 are preferably in cis configuration, and wherein ring A in formula (III) represents a 5-membered or 6-membered carbocyclic or heterocyclic ring containing at least one double bond, including an aromatic carbocyclic or heterocyclic ring, which can be substituted with one to three or one to four substituents independently selected from the group consisting of $C_1$-$C_6$alkyl, $C_1$-$C_6$alkoxy, $C_1$-$C_6$alkylthio, fluorine or chlorine atom, hydroxyl group, amino group, —NH($C_1$-$C_6$alkyl), and —N($C_1$-$C_6$)dialkyl; and L and T each independently represents a ring atom, wherein L and T are adjacent to another;

$R^{12}$ and $R^{13}$ each independently represents a hydrogen atom, a fluorine atom, hydroxyl, —$NH_2$, $C_1$-$C_6$alkyl, $C_1$-$C_6$alkoxy, —C(=O)-aryl, —C(=O)$C_1$-$C_6$alkyl, or —$SO_2(C_1$-$C_6$alkyl); or —$SO_2$aryl; wherein any of the foregoing $C_1$-$C_6$alkyl, $C_1$-$C_6$alkoxy, or aryl are optionally substituted with one, two or three substituents independently selected from the group of —$NH_2$, —$NH(C_1$-$C_6$)alkyl, —$N(C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxyl; or $R^{12}$ and $R^{13}$ are taken together to form a 5-membered or 6-membered ring, which ring is optionally substituted with one, two or three substituents independently selected from the group consisting of —$NH_2$, —$NH(C_1$-$C_6$)alkyl, —$N(C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxyl;

I is —$(CH_2)_m$—Y, wherein m is an integer of from 3 to 6, i.e. 3, 4, 5, or 6, provided that m is an integer of from 3 to 5 when E is a group according to general formula (III);

Y represents —U—V—W—$(CH_2)_p$—$(CH_3)_q$, wherein p is an integer from 0 to 6; q is 0 or 1; U is absent or selected from the group consisting of CH, $CH_2$ and $NR^{40}$, with the proviso that U is only CH if it forms an epoxy group together with V and W; V is selected from the group consisting of —C(O)—, —C(O)—C(O)—, —O—, and —S—; W is selected from the group consisting of CH, $CH_2$ and $NR^{40}$ with the proviso that W is only CH if it forms an epoxy group together with U and V;

or Y represents a group selected from the group consisting of:

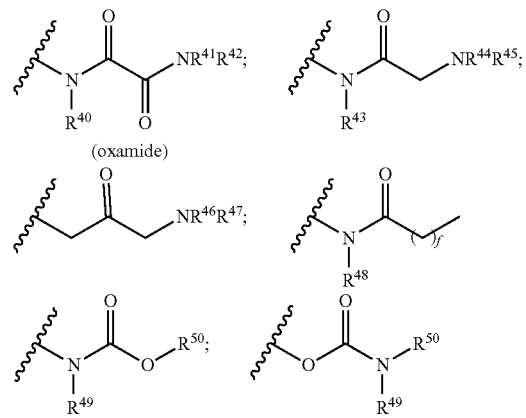

wherein $R^{40}$, $R^{41}$, $R^{43}$, $R^{44}$, $R^{46}$, $R^{4'}$ and $R^{49}$ each independently represents a hydrogen atom, —$C_1$-$C_6$alkyl, —$C_3$-$C_6$cycloalkyl, —$C_1$-$C_6$alkoxy, —C(=O)aryl, or —C(=O)$C_1$-$C_6$alkyl, wherein any of the foregoing $C_1$-$C_6$alkyl, $C_3$-$C_6$cycloalkyl, $C_1$-$C_6$alkoxy, or aryl are optionally substituted with one, two or three substituents independently selected from the group consisting of —$NH_2$, —$NH(C_1$-$C_6$)alkyl, —$N(C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxy; or $R^{40}$ and $R^{41}$, or $R^{43}$ and $R^{44}$, are taken together to form a 5-membered or 6-membered ring, which ring may be substituted with one, two or three substituents independently selected from the group consisting of —$NH_2$, —$NH(C_1$-$C_6$)alkyl, —$N(C_1$-$C_6$)dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxyl;

$R^{42}$, $R^{45}$, $R^{47}$ and $R^{50}$ each independently represents a —$C_1$-$C_3$alkyl, wherein the $C_1$-$C_3$alkyl may be substituted with one, two or three substituents independently selected from the group consisting of —$NH_2$, —NH($C_1$-$C_3$)alkyl, —N($C_1$-$C_3$)dialkyl, $C_1$-$C_3$alkylcarbonyloxy-, $C_1$-$C_3$alkoxycarbonyloxy-, $C_1$-$C_3$alkylcarbonylthio-, $C_1$-$C_3$alkylaminocarbonyl-, di($C_1$-$C_3$)alkylaminocarbonyl-, fluorine or chlorine atom, and hydroxyl; or $R^{40}$ and $R^{41}$; $R^{43}$ and $R^{44}$; $R^{49}$ and $R^{50}$ are taken together to form a 5-membered or 6-membered ring, which ring may be substituted with one, two or three substituents independently selected from the group consisting of —$NH_2$, —$NH(C_1$-$C_6)$alkyl, —$N(C_1$-$C_6)$dialkyl, $C_1$-$C_6$alkylcarbonyloxy-, $C_1$-$C_6$alkoxycarbonyloxy-, $C_1$-$C_6$alkylcarbonylthio-, $C_1$-$C_6$alkylaminocarbonyl-, di($C_1$-$C_6$)alkylaminocarbonyl-, fluorine or chlorine atom, and hydroxyl;

f is an integer of from 0 to 2;

with the proviso that when X does not comprise a —C(=O)O-motif with the carbonyl carbon in alpha or beta position to the oxygen atom of general formula (II), Y is an oxamide, a carbamate or a carbamide, preferably Y is an oxamide as defined above for use in treating, reducing the risk of developing or preventing a disorder associated with neovascularization and/or inflammation.

In a preferred embodiment, the compounds of present invention are compounds of formula (I) as described above with the proviso that when X does not comprise a —C(=O)O-motif with the carbonyl carbon in alpha or beta position to the oxygen atom of general formula (II), Y is an oxamide, a carbamate or a carbamide, preferably Y is an oxamide as defined above.

In a preferred embodiment, the compounds of formula (I) are compounds as described above with the further proviso that when n is 3, 5, 6, 7 or 8, preferably 3 k is 1 and E is a group according to general formula (III) or general formula (IV), wherein each of $R^{12}$ and $R^{13}$ is a hydrogen atom;

P represents a group:

—(CH$_2$)$_3$—O—(CH$_2$)—X$^{81}$; —(CH$_2$)$_s$—O—(CH$_2$)—X$^{81}$;

wherein

X$^{81}$ represents a group selected from the group consisting of:

$R^{1'}$ is defined as $R^1$ above;

$R^{2'}$ represents —NHR$^{3'}$; —OR$^{22'}$; —(OCH$_2$—CH$_2$)$_i$—R$^{23}$; a mono-, or disaccharide, or a derivative thereof, which is joined to —C(=O) by an ester bond via the 1-O-, 3-O-, or 6-O-position of the saccharide;

or wherein $R^2$ is selected from the group consisting of:

wherein $R^{3'}$ represents (SO$_2$R$^{30}$); (OR$^{31}$); —C$_1$-C$_6$alkanediyl (SO$_2$R$^{32}$); or —C$_2$-C$_6$alkanediyl(CO$_2$H);

$R^{22'}$ is a hydrogen or a C$_3$-C$_6$cycloalkyl group, which is optionally substituted with —NH$_2$, —NH(C$_1$-C$_6$)alkyl, —N(C$_1$-C$_6$)dialkyl, —NH(C$_1$-C$_6$)alkyldiyl-C$_1$-C$_6$alkoxy, one, two or three fluorine or chlorine atom(s), hydroxy, or C$_1$-C$_6$alkoxy;

$R^{23}$ and i are as defined above;

$R^{24}$, $R^{25}$, $R^{26}$, and $R^{22}$ are as defined above;

$R^{4'}$ is defined as $R^4$ above; and h is defined as above;

$R^{6'}$ and $R^{7'}$ are defined as $R^6$ and $R^7$ above;

$R^{8''}$ and $R^{8'''}$ are defined as $R^8$ and $R^{8'}$ above;

$R^{9''}$ is defined as $R^9$ above; $R^{9'''}$ represents aryl which is optionally substituted with one, two or three substituents independently selected from the group consisting of C$_1$-C$_6$alkyl, C$_1$-C$_6$alkoxy, C$_1$-C$_6$alkylthio, fluorine or chlorine atom, hydroxyl group, amino group, —NH(C$_1$-C$_6$alkyl), —N(C$_1$-C$_6$)dialkyl, and an oxo substituent.

In a more preferred embodiment the compound of the present invention is one, wherein X is

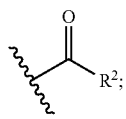

wherein R² is —OR²²; —(OCH₂—CH₂)ᵢ—R²³; a mono-, or disaccharide, or a derivative thereof, which is joined to —C(=O) by an ester bond via the 1-O-, 3-O-, or 6-O-position of the saccharide;

or wherein R² is selected from the group consisting of:

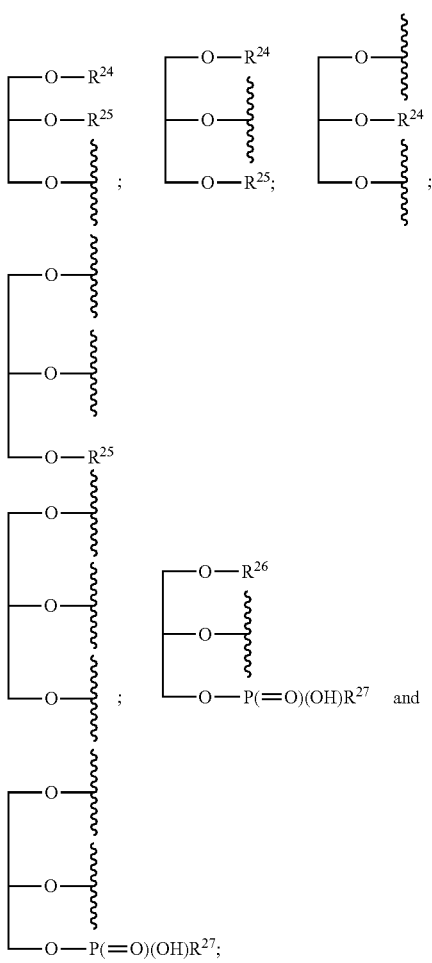

wherein R²³ and i are as defined above, preferable i is 3;
and wherein R²², and R²³ to R²⁷ are as defined in claim 1, preferably R²² is a hydrogen atom or a C₁-C₆alkyl group, more preferably a hydrogen atom.

In a further more preferred embodiment, the compound of the present invention is one, wherein X is —C(=O)OH or a suitable salt of the carboxylic acid, preferably a free carboxylic acid.

In another more preferred embodiment, the compound of the present invention is one, wherein Y is one of the oxamides as defined above.

It is further preferred that the compound of the present invention is one, wherein X is

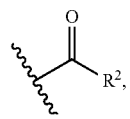

wherein R² is —OR²²; —(OCH₂—CH₂)ᵢ—R²³; a mono-, or disaccharide, or a derivative thereof, which is joined to —C(=O) by an ester bond via the 1-O-, 3-O-, or 6-O-position of the saccharide; or wherein R² is selected from the group consisting of:

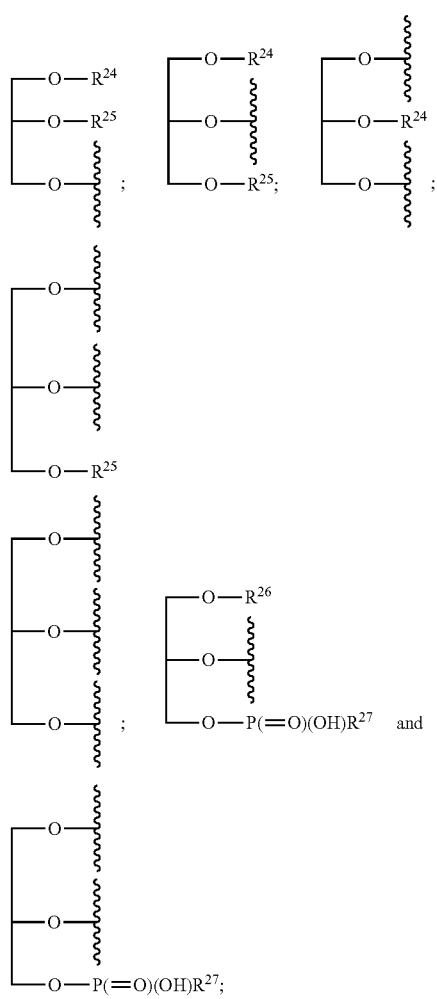

wherein and R²², R²³ to R²⁷ and i are as defined above, preferably R²² is a hydrogen atom or a C₁-C₆alkyl group, more preferably a hydrogen atom, preferably i is 2 to 4, more preferably 3, and wherein Y is preferably one of the oxamides defined above.

In a more preferred embodiment, the compound of the present invention is one, wherein X is C(=O)OH, preferably the free carboxylic acid, and Y is preferably one of the oxamides defined above.

In another more preferred embodiment, the compound of the present invention is one with the following formula (V):

formula (V)

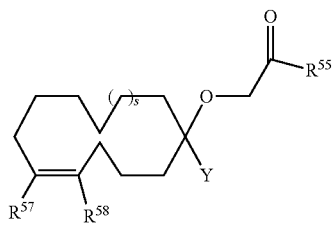

wherein
$R^{55}$ represents —OH; —OR$^{22}$; —(OCH$_2$—CH$_2$)$_i$—R$^{23}$; a mono-, or disaccharide, or a derivative thereof, which is joined to —C(=O) by an ester bond via the 1-O-, 3-O-, or 6-O-position of the saccharide;

$R^{22}$, $R^{23}$ and i are as defined above, preferably $R^{22}$ is a hydrogen atom or a $C_1$-$C_6$alkyl group, more preferably a hydrogen atom and i is preferably 2 to 4, more preferably 3;

Y represents a group selected from the group consisting of:

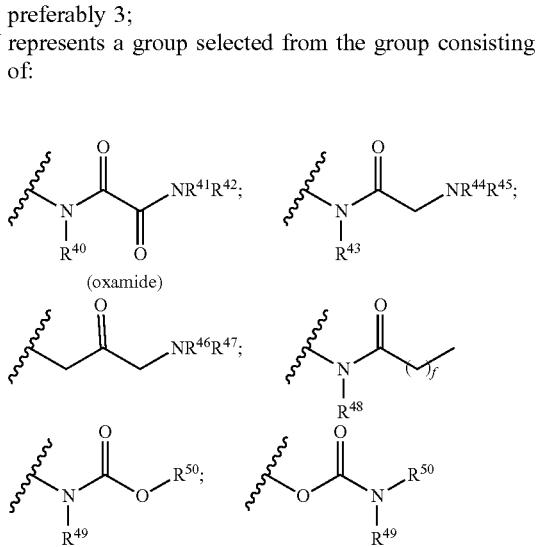

wherein

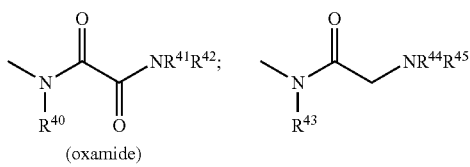

are preferred, and

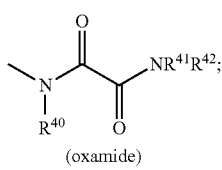

is particularly preferred; and
wherein $R^{40}$ to $R^{50}$ are defined above, preferably $R^{40}$ is a hydrogen atom or a $C_1$-$C_6$alkyl group, more preferably a hydrogen atom $R^{57}$ and $R^{58}$ are hydrogen; or form together a five- or six-membered ring, preferably an aromatic ring, optionally substituted with one to three or one to four substituents independently selected from the group consisting of $C_1$-$C_6$alkyl, $C_1$-$C_6$alkoxy, $C_1$-$C_6$alkylthio, fluorine or chlorine atom, hydroxyl group, amino group, —NH($C_1$-$C_6$alkyl), —N($C_1$-$C_6$)dialkyl, and an oxo substituent;

s is 0, 1 or 2, with the proviso that s is 0 if $R^{57}$ and $R^{58}$ form together a five- or six-membered ring;

the double bond in formula (V) represents a double carbon-carbon bond in cis-configuration, if $R^{57}$ and $R^{58}$ are hydrogen, or this double bond is part of a five- or six-membered ring formed together by $R^{57}$ and $R^{58}$.

In a further most preferred embodiment the compounds of formula (V) are those wherein $R^{55}$ represents —OH or —(OCH$_2$—CH$_2$)$_i$—R$^{23}$; i is 2 to 4, preferably i is 3; $R^{23}$ is preferably OH;

Y is an oxamide, a carbamide or a carbamate, preferably a $C_1$-$C_6$alkyl substituted oxamide, carbamide or carbamate;

$R^{57}$ and $R^{58}$ are both H, or together form a substituted or non-substituted five- or six-membered aromatic ring, preferably form a substituted or non-substituted benzyl ring; and s is 1 or s is 0 if $R^{57}$ and $R^{58}$ together form a substituted or non-substituted five- or six-membered aromatic ring.

The most preferred specific compounds of the present invention are those selected from the group consisting of:

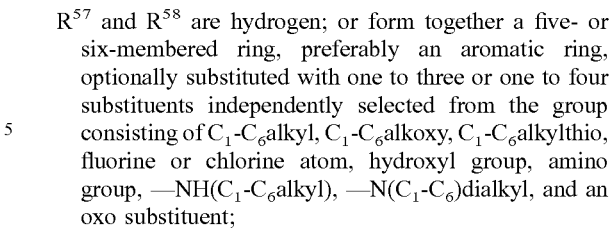

-continued
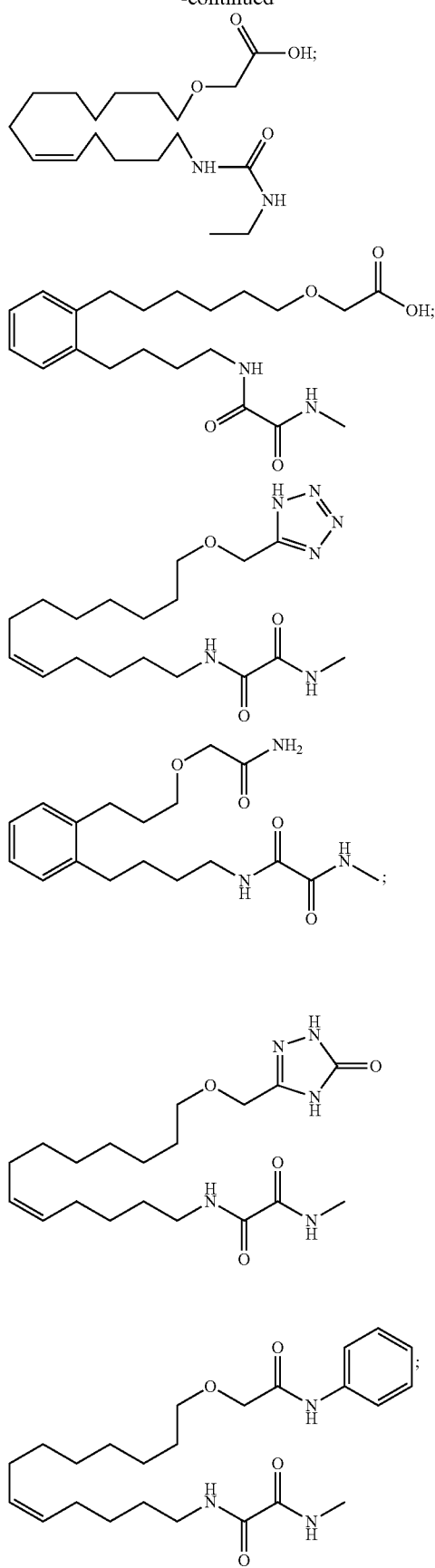
-continued
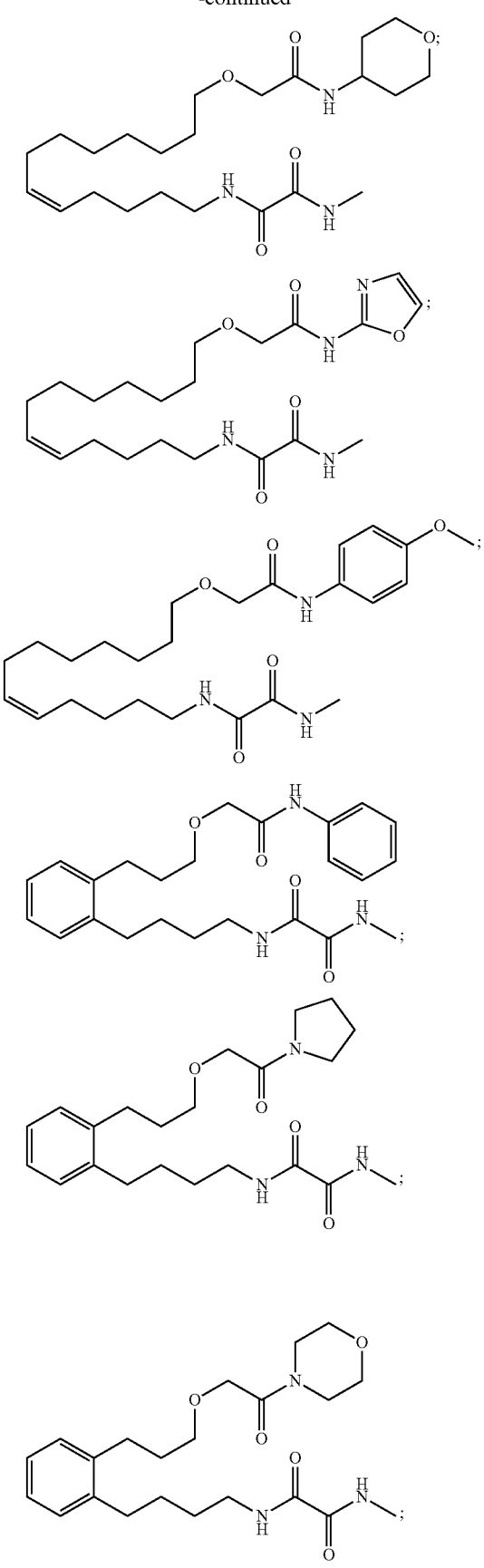

-continued

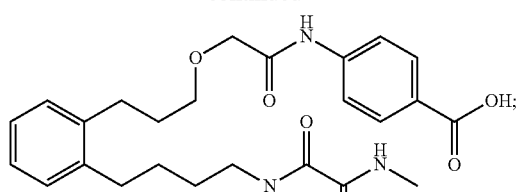

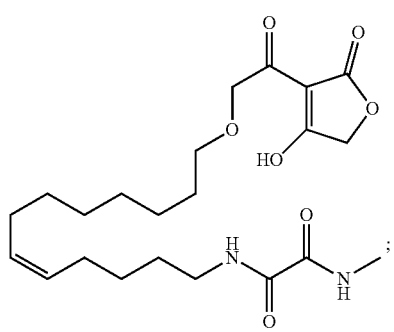

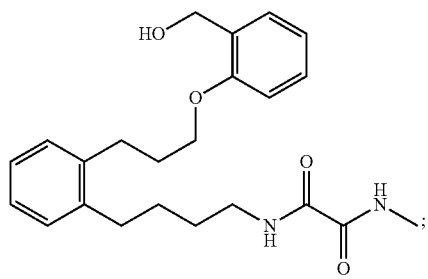

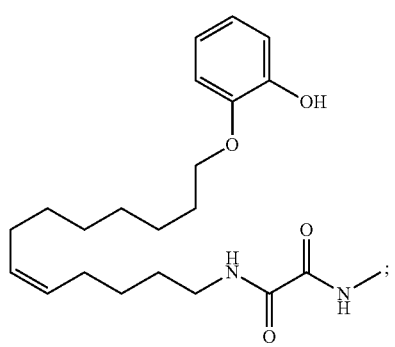

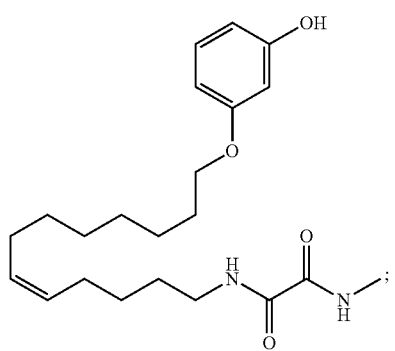

-continued

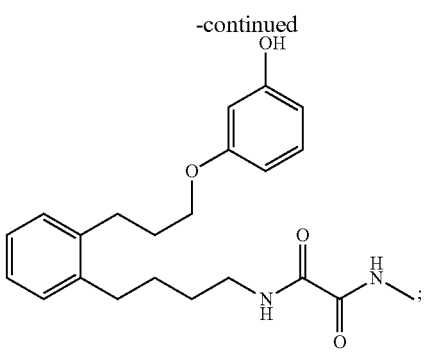

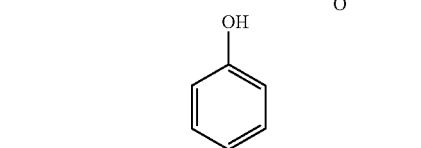

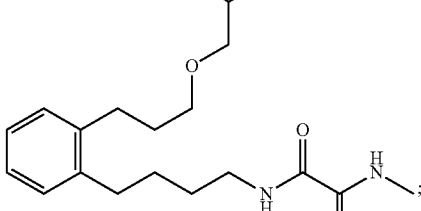

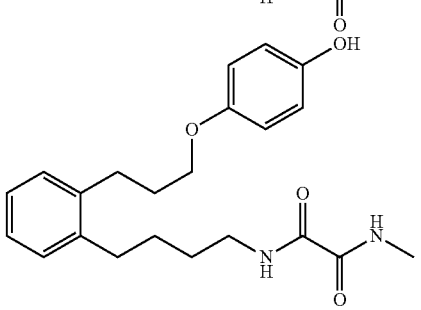

and or a pharmaceutically acceptable salt thereof.

Among the above, the compound with the following formula (VI)

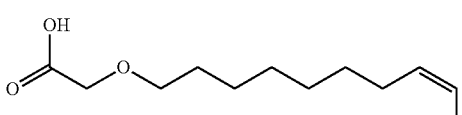

formula (VI)

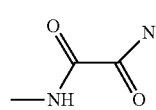

or a pharmaceutically acceptable salt thereof is most preferred.

The compounds of the present invention have the advantage as demonstrated below in the experimental section that they are effective for treating, reducing the risk of developing or preventing a disorder associated with neovascularization and/or inflammation, in particular an ophthalmic disorder associated with neovascularization and/or inflammation. They are at the same time metabolically robust for pharmaceutical formulation and administration to subjects in need thereof.

The compounds described herein are generally described using standard nomenclature. For compounds having asymmetric centers, it is understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic center(s), have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors, biosynthesis, e.g. using modified CYP102 (CYP BM-3) or by resolution of the racemates, e.g. enzymatic resolution or resolution by conventional methods such as crystallization in the presence of a resolving agent, or chromatography, using, for example, a chiral HPLC column.

Certain compounds are described herein using a general formula that includes variables such as, e.g. P, E, I, $R^1$-$R^{50}$, X—$X^{81}$, and Y. Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted or substituted with up to two R* groups, and R* at each occurrence is selected independently from the definition of R*. Also, combinations of substituents and/or variables are permissible only if such combinations result in stable compounds, i.e., compounds that can be isolated, characterized and tested for biological activity.

A "pharmaceutically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzenesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is any integer from 0 to 6, i.e. 0, 1, 2, 3, 4, 5 or 6, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

It will be apparent that each compound of formula (I) may, but need not, be present as a hydrate, solvate or non-covalent complex. In addition, the various crystal forms and polymorphs are within the scope of the present invention as are prodrugs of the compounds of formula (I) provided herein".

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

A "substituent," as used herein, refers to a molecular moiety that is covalently bonded to an atom within a molecule of interest. For example, a "ring substituent" may be a moiety such as a halogen, alkyl group, haloalkyl group or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity. When a substituent is oxo, i.e., =O, then 2 hydrogens on the atom are replaced. An oxo group that is a substituent of an aromatic carbon atom results in a conversion of —CH— to —C(=O)— and a loss of aromaticity. For example a pyridyl group substituted by oxo is a pyridone.

The expression "optionally substituted" refers to a group in which one, two, three or more hydrogen atoms may have been replaced independently of each other by the respective substituents.

As used herein, the term "amino acid" refers to any organic acid containing one or more amino substituents, e.g. α-, β- or γ-amino, derivatives of aliphatic carboxylic acids. In the polypeptide notation used herein, e.g. $Xaa_5$, i.e. $Xaa_1Xaa_2Xaa_3Xaa_4Xaa_5$, wherein $Xaa_1$ to $Xaa_5$ are each and independently selected from amino acids as defined, the left hand direction is the amino terminal direction and the right hand direction is the carboxy terminal direction, in accordance with standard usage and convention.

The term "conventional amino acid" refers to the twenty naturally occurring amino acids, and encompasses all stereomeric isoforms, i.e. D,L-, D- and L-amino acids thereof. These conventional amino acids can herein also be referred to by their conventional three-letter or one-letter abbreviations and their abbreviations follow conventional usage (see, for example, *Immunology—A Synthesis*, 2$^{nd}$ Edition, E. S. Golub and D. R. Gren, Eds., Sinauer Associates, Sunderland Mass. (1991)).

The term "non-conventional amino acid" refers to unnatural amino acids or chemical amino acid analogues, e.g. α,α-disubstituted amino acids, N-alkyl amino acids, homo-amino acids, dehydroamino acids, aromatic amino acids (other than phenylalanine, tyrosine and tryptophan), and ortho-, meta- or para-aminobenzoic acid. Non-conventional amino acids also include compounds which have an amine and carboxyl functional group separated in a 1,3 or larger substitution pattern, such as β-alanine, γ-amino butyric acid, Freidinger lactam, the bicyclic dipeptide (BTD), aminomethyl benzoic acid and others well known in the art. Statine-like isosteres, hydroxyethylene isosteres, reduced amide bond isosteres, thioamide isosteres, urea isosteres, carbamate isosteres, thioether isosteres, vinyl isosteres and other amide bond isosteres known to the art may also be used. The use of analogues or non-conventional amino acids may improve the stability and biological half-life of the added peptide since they are more resistant to breakdown under physiological conditions. The person skilled in the art will be aware of similar types of substitution which may be made. A non limiting list of non-conventional amino acids which may be used as suitable building blocks for a peptide and their standard abbreviations (in brackets) is as follows: a-aminobutyric acid (Abu), L-N-methylalanine (Nmala), a-amino-α-methylbutyrate (Mgabu), L-N-methylarginine (Nmarg), aminocyclopropane (Cpro), L-N-methylasparagine (Nmasn), carboxylate L-N-methylaspartic acid (Nmasp), aniinoisobutyric acid (Aib), L-N-methylcysteine (Nmcys), aminonorbornyl (Norb), L-N-methylglutamine (Nmgln), carboxylate L-N-methylglutamic acid (Nmglu), cyclohexylalanine (Chexa), L-N-methylhistidine (Nmhis), cyclopentylalanine (Cpen), L-N-methylisolleucine (Nmile), L-N-methylleucine (Nmleu), L-N-methyllysine (Nmlys), L-N-methylmethionine (Nmmet), L-N-methylnorleucine (Nmnle), L-N-methylnorvaline (Nmnva), L-N-methylornithine (Nmorn), L-N-methylphenylalanine (Nmphe), L-N-methylproline (Nmpro), L-N-methylserine (Nmser), L-N-methylthreonine (Nmthr), L-N-methyltryptophan (Nmtrp), D-ornithine (Dorn), L-N-methyltyrosine (Nmtyr), L-N-methylvaline (Nmval), L-N-methylethylglycine (Nmetg), L-N-methyl-t-butylglycine (Nmtbug), L-norleucine (Nie), L-norvaline (Nva), a-methyl-aminoisobutyrate (Maib), a-methyl-γ-aminobutyrate (Mgabu), D-α-methylalanine (Dmala), a-methylcyclohexylalanine (Mchexa), D-α-methylarginine (Dmarg), a-methylcylcopentylalanine (Mcpen), D-α-methylasparagine (Dmasn), a-methyl-α-napthylalanine (Manap), D-α-methylaspartate (Dmasp), a-methylpenicillamine (Mpen), D-a-methylcysteine (Dmcys), N-(4-aminobutyl)glycine (Nglu), D-α-methylglutamine (Dmgln), N-(2-aminoethyl)glycine (Naeg), D-α-methylhistidine (Dmhis), N-(3-aminopropyl)glycine (Norn), D-α-methylisoleucine (Dmile), N-amino-α-methylbutyrate (Nmaabu), D-α-methylleucine (Dmleu), a-napthylalanine (Anap), D-α-methyllysine (Dmlys), N-benzylglycine (Nphe), D-α-methylmethionine (Dmmet), N-(2-carbamylethyl)glycine (NgIn), D-α-methylornithine (Dmorn), N-(carbamyl-methyl)glycine (Nasn), D-α-methylphenylalanine (Dmphe), N-(2-carboxyethyl)glycine (Nglu), D-α-methylproline (Dmpro), N-(carboxymethyl)glycine (Nasp), D-α-methylserine (Dmser), N-cyclobutylglycine (Ncbut), D-α-methylthreonine (Dmthr), N-cycloheptylglycine (Nchep), D-α-methyltryptophan (Dmtrp), N-cyclohexylglycine (Nchex), D-α-methyltyrosine (Dmty), N-cyclo-decylglycine (Ncdec), D-α-methylvaline (Dmval), N-cylcododecylglycine (Ncdod), D-N-methylalanine (Dnmala), N-cyclooctylglycine (Ncoct), D-N-methylarginine (Dnmarg), N-cyclopropylglycine (Ncpro), D-N-methylasparagine (Dnmasn), N-cycloundecylglycine (Ncund), D-N-methylaspartate (Dnmasp), N-(2,2-diphenylethyl)glycine (Nbhm), D-N-methylcysteine (Dnmcys), N-(3,3-diphenylpropyl)glycine (Nbhe), D-N-methylglutamine (Dnmgln), N-(3-guanidinopropyl)glycine (Narg), D-N-methylglutamate (Dnmglu), N-(1-hydroxyethyl)glycine (Ntbx), D-N-methylhistidine (Dnmhis), N-(hydroxyethyl))glycine (Nser), D-N-methylisoleucine (Dnmile), N-(imidazolylethyl))glycine (Nhis), D-N-methylleucine (Dnmleu), N-(3-indolylyethyl)glycine (Nhtrp), D-N-methyllysine (Dnnilys), N-methyl-y-aminobutyrate (Nmgabu), N-methylcyclohexylalanine (Nmchexa), D-N-methylmethionine (Dnmmet), D-N-methylornithine (Dnmorn), N-methylcyclopentylalanine (Nmcpen), N-methylglycine (Nala), D-N-methylphenylalanine (Dnmphe), N-methylaminoisobutyrate (Nmaib), D-N-methylproline (Dnmpro), N-(1-methylpropyl)glycine (Nile), D-N-methylserine (Dnmser), N-(2-methylpropyl)glycine (Nleu), D-N-methylthreonine (Dnmthr), D-N-methyltryptophan (Dnmtrp), N-(1-methylethyl)glycine (Nval), D-N-methyltyrosine (Dnmtyr), N-methyla-napthylalanine (Nmanap), D-N-methylvaline (Dnmval), N-methylpenicillamine (Nmpen), y-aminobutyric acid (Gabu), N-(p-hydroxyphenyl)glycine (Nhtyr), L-/-butylglycine (Tbug), N-(thiomethyl)glycine (Ncys), L-ethylglycine (Etg), penicillamine (Pen), L-homophenylalanine (Hphe), L-α-methylalanine (Mala), L-α-methylarginine (Marg), L-α-methylasparagine (Masn), L-α-methylaspartate (Masp), L-α-methyl-t-butylglycine (Mtbug), L-α-methylcysteine (Mcys), L-methylethylglycine (Metg), L-α-methylglutamine (Mgln), L-α-methylglutamate (Mglu), L-α-methylhistidine (Mhis), L-α-methylhomophenylalanine (Mhphe), L-α-methylisoleucine (Mile), N-(2-methylthioethyl)glycine (Nmet), L-α-methylleucine (Mleu), L-α-methyllysine (Mlys), L-α-methylmethionine (Mmet), L-α-methylnorleucine (Mnle), L-α-methylnorvaline (Mnva), L-α-methylornithine (Morn), L-α-methylphenylalanine (Mphe), L-α-methylproline (Mpro), L-α-methylserine (Mser), L-α-methylthreonine (Mthr), L-α-methyltryptophan (Mtrp), L-α-methyltyrosine (Mtyr), L-α-methylvaline (Mval), L-N-methylhomophenylalanine (Nmhphe), N—(N-(2,2-diphenylethyl)carbamylmethyl)glycine (Nnbhm), N—(N-(3,3-diphenylpropyl)-carbamylmethyl)glycine (Nnbhe), 1-carboxy-1-(2,2-diphenyl-ethylamino)cyclopropane (Nmbc), L-O-methyl serine (Omser), L-O-methyl homoserine (Omhser).

The expression alkyl refers to a saturated, straight-chain or branched hydrocarbon group that contains from 1 to 20 carbon atoms, preferably from 1 to 10 carbon atoms, e.g. a n-octyl group, especially from 1 to 6, i.e. 1, 2, 3, 4, 5, or 6, carbon atoms, for example a methyl, ethyl, propyl, isopropyl, n-butyl, iso-butyl, sec-butyl, tert-butyl, n-pentyl, iso-pentyl, n-hexyl, or 2,2-dimethylbutyl.

The expression alkenyl refers to an at least partially unsaturated, straight-chain or branched, hydrocarbon group that contains from 2 to 21 carbon atoms, preferably from 2 to 6 carbon atoms, i.e. 2, 3, 4, 5 or 6 carbon atoms, for example an ethenyl (vinyl), propenyl (allyl), iso-propenyl, butenyl, isoprenyl or hex-2-enyl group, or from 11 to 21 carbon atoms, i.e. 11, 12, 13, 14, 15, 16, 17, 18, 19, 20 or 21 carbon atoms, for example a hydrocarbon group comprising a methylene chain interrupted by one double bond as, for example, found in monounsaturated fatty acids or a hydrocarbon group comprising methylene-interrupted polyenes, e.g. hydrocarbon groups comprising two or more of the following structural unit —[CH=CH—CH$_2$]—, as, for example, found in polyunsaturated fatty acids. Alkenyl groups have one or more, preferably 1, 2, 3, 4, 5, or 6 double bond(s).

The expression alkynyl refer to at least partially unsaturated, straight-chain or branched hydrocarbon groups that contain from 2 to 20 carbon atoms, preferably from 2 to 10 carbon atoms, especially from 2 to 6, i.e. 2, 3, 4, 5 or 6, carbon atoms, for example an ethinyl, propinyl, butinyl, acetylenyl, or propargyl group. Preferably, alkynyl groups have one or two (especially preferably one) triple bond(s).

Furthermore, the terms alkyl, alkenyl and alkynyl refer to groups in which one or more hydrogen atom(s) have been replaced, e.g. by a halogen atom, preferably F or C$_1$, such as, for example, a 2,2,2-trichloroethyl or a trifluoromethyl group.

The expression heteroalkyl refers to an alkyl, alkenyl or alkynyl group in which one or more, preferably 1, 2 or 3, carbon atoms, have been replaced independently of each other by an oxygen, nitrogen, phosphorus, boron, selenium, silicon or sulfur atom, preferably by an oxygen, sulfur or nitrogen atom. The expression heteroalkyl can also refer to a carboxylic acid or to a group derived from a carboxylic acid, such as, for example, acyl, acylalkyl, alkoxycarbonyl, acyloxy, acyloxyalkyl, carboxyalkylamide or alkoxycarbonyloxy.

Preferably, a heteroalkyl group contains from 1 to 10 carbon atoms and from 1 to 4 hetero atoms selected from oxygen, nitrogen and sulphur (especially oxygen and nitrogen). Especially preferably, a heteroalkyl group contains from 1 to 6, i.e. 1, 2, 3, 4, 5, or 6, carbon atoms and 1, 2 or 3, especially 1 or 2, hetero atoms selected from oxygen, nitrogen and sulphur, especially oxygen and nitrogen.

Examples of heteroalkyl groups are groups of formulae: $R^a$—O—$Y^a$—, $R^a$—S—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a C$_1$-C$_6$ alkyl, a C$_2$-C$_6$ alkenyl or a C$_2$-C$_6$ alkynyl group; $R^b$ being a hydrogen atom, a C$_1$-C$_6$ alkyl, a C$_2$-C$_6$ alkenyl or a C$_2$-C$_6$ alkynyl group; $R^c$ being a hydrogen atom, a C$_1$-C$_6$ alkyl, a C$_2$-C$_6$ alkenyl or a C$_2$-C$_6$ alkynyl group; $R^d$ being a hydrogen atom, a C$_1$-C$_6$ alkyl, a C$_2$-C$_6$ alkenyl or a C$_2$-C$_6$ alkynyl group and $Y^a$ being a direct bond, a C$_1$-C$_6$ alkylene, a C$_2$-C$_6$ alkenylene or a C$_2$-C$_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, isopropyloxy, butoxy, tert-butyloxy, methoxymethyl, ethoxymethyl, —CH$_2$CH$_2$OH, —CH$_2$OH, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropylethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression alkoxy refers to an alkyl group singular bonded to oxygen.

The expression alkylthio refers to an alkyl group singular bonded to sulfur.

The expressions cycloalkyl and carbocyclic ring refer to a saturated cyclic group of hydrocarbons that contains one or more rings, preferably 1 or 2), and contains from 3 to 14 ring carbon atoms, preferably from 3 to 10, especially 3, 4, 5, 6 or 7 ring carbon atoms, e.g. a cyclopropyl, cyclobutyl, cyclopentyl, spiro[4,5]decanyl, norbornyl, cyclohexyl, decalinyl, bicyclo[4.3.0]nonyl, tetraline, or cyclopentylcyclohexyl group. The expression cycloalkyl refers furthermore to groups in which one or more hydrogen atoms have been replaced by fluorine, chlorine, bromine or iodine atoms or by OH, =O, SH, NH$_2$, =NH, N$_3$ or NO$_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression aryl refers to an aromatic group that contains one or more rings containing from 6 to 14 ring carbon atoms, preferably from 6 to 10, especially 6, ring carbon atoms.

The expression heteroaryl refers to an aromatic group that contains one or more rings containing from 5 to 14 ring atoms, preferably from 5 to 10, especially 5 or 6, ring atoms, and contains one or more, preferably 1, 2, 3 or 4, oxygen, nitrogen, phosphorus or sulfur ring atoms, preferably 0, S or N. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups. The expression heterocycloalkyl refers to a cycloalkyl group as defined above in which one or more (preferably 1, 2 or 3) ring carbon atoms, each independently, have been replaced by an oxygen, nitrogen, silicon, selenium, phosphorus or sulfur atom (preferably by an oxygen, sulfur or nitrogen atom). A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups in which one or more hydrogen atoms have been replaced by fluorine, chlorine, bromine or iodine atoms or by OH, =O, SH, =S, NH$_2$, =NH, N$_3$ or NO$_2$ groups. Examples are a piperidyl, prolinyl, imidazolidinyl, piperazinyl, morpholinyl, urotropinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to a group that contains both cycloalkyl and also alkyl, alkenyl or alkynyl groups in accordance with the above definitions, for example alkylcycloalkyl, cyclo-alkylalkyl, alkylcycloalkenyl, alkenylcycloalkyl and alkynylcycloalkyl groups. An alkylcycloalkyl group preferably contains a cycloalkyl group that contains one or two ring systems having from 3 to 10 (especially 3, 4, 5, 6 or 7) ring carbon atoms, and one or two alkyl, alkenyl or alkynyl groups having 1 or 2 to 6 carbon atoms. The expression aralkyl refers to a group containing both aryl and also alkyl, alkenyl, alkynyl and/or cycloalkyl groups in accordance with the above definitions, such as, for example, an arylalkyl, arylalkenyl, arylalkynyl, arylcycloalkyl, arylcycloalkenyl, alkylarylcycloalkyl and alkylarylcycloalkenyl group. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroalkylcycloalkyl refers to alkylcycloalkyl groups as defined above in which one or more, preferably 1, 2 or 3, carbon atoms have been replaced independently of each other by an oxygen, nitrogen, silicon, selenium, phosphorus or sulfur atom (preferably by an oxygen, sulfur or nitrogen atom). A heteroalkylcycloalkyl group preferably contains 1 or 2 ring systems having from 3 to 10 (especially 3, 4, 5, 6 or 7) ring atoms, and one or two alkyl, alkenyl, alkynyl or heteroalkyl groups having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The expression heterocyclic ring refers to heteroaryl group as defined above as well as to a cycloalkyl group or carbocyclic ring as defined above in which one or more (preferably 1, 2 or 3) ring carbon atoms, each independently, have been replaced by an oxygen, nitrogen, silicon, selenium, phosphorus or sulfur atom, preferably by an oxygen, sulfur or nitrogen atom. A heterocyclic ring has preferably 1 or 2 ring(s) containing from 3 to 10, especially 3, 4, 5, 6 or 7 ring atoms, preferably selected from C, O, N and S. Examples are a aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, tetrahydrofuranyl, thiolanyl, phospholanyl, silolanyl, azolyl, thiazolyl, isothiazolyl, imidazolidinyl, pyrazolidinyl, oxazolidinyl, isoxazolidinyl, thiazolidinyl, isothiazolidinyl, dioxolanyl, dithiolanyl, piperazinyl, morpholinyl, thiopmorpholinyl, trioxanyl, azepanyl, oxepanyl, thiepanyl, homopiperazinyl, or urotropinyl group.

The expression heteroaralkyl refers to an aralkyl group as defined above in which one or more (preferably 1, 2, 3 or 4) carbon atoms, each independently, have been replaced by an oxygen, nitrogen, silicon, selenium, phosphorus, boron or sulfur atom (preferably oxygen, sulfur or nitrogen), that is to say to a group containing both aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, wherein 1, 2, 3 or 4 of these carbon atoms have been replaced by oxygen, sulfur or nitrogen atoms.

Examples are arylheteroalkyl, arylheterocycloalkyl, arylheterocycloalkenyl, arylalkyl-heterocycloalkyl, arylalkenylheterocycloalkyl, arylalkynylheterocycloalkyl, arylalkylheterocyclo-alkenyl, heteroarylalkyl, heteroarylalkenyl, heteroarylalkynyl, heteroarylheteroalkyl, heteroaryl-cycloalkyl, heteroarylcycloalkenyl, heteroarylheterocycloalkyl, heteroarylheterocycloalkenyl, hetero-arylalkylcycloalkyl, heteroarylalkylheterocycloalkenyl, heteroarylheteroalkylcycloalkyl, heteroaryl-heteroalkylcycloalkenyl and heteroarylheteroalkylheterocycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups in which one or more hydrogen atoms of such groups have been replaced independently of each other by fluorine, chlorine, bromine or iodine atoms or by OH, =O, SH, =S, NH$_2$, =NH, N$_3$ or NO$_2$ groups.

The general term ring as used herein, unless defined otherwise, includes cycloalkyl groups or carbocyclic rings, heterocyclic rings, aryl groups, and heteroaryl groups.

The expressions "halo", "halogen"" or "halogen atom" as used herein means fluorine, chlorine, bromine, or iodine, preferably fluorine and/or chlorine.

The expression mono- or disaccharide, and derivatives thereof as used herein means a carbohydrate or sugar belonging to or derived from the group of monosaccharides or disaccharides.

Examples of mono-, disaccharides, and derivatives include glucose, 3-O-methyl-glucose, 1-deoxy-glucose, 6-deoxy-glucose, galactose, mannose, fructose, xylose, ribose, cellobiose, maltose, lactose, gentiobiose, saccharose, trehalose and mannitol, sorbitol and ribitol. Preferably, the saccharides are D-form saccharides, e.g. D-glucose, 3-O-methyl-D-glucose, 1-deoxy-D-glucose, or 6-deoxy-D-glucose, D-galactose, D-mannose.

As used herein a wording defining the limits of a range of length such as, e. g., "from 1 to 5" means any integer from 1 to 5, i.e. 1, 2, 3, 4 and 5. In other words, any range defined by two integers explicitly mentioned is meantto comprise and disclose any integer defining said limits and any integer comprised in said range.

The expression "—C(=O)O-motif" is used herein in order to clearly define a group comprising an sp$^2$-hybridized carbonyl carbon attached (i) to any carbon or hetero atom and (ii) to an oxygen which in turn can be attached to hydrogen or any other chemical atom. The term "carboxyl group" is avoided for the description of a "—C(=O)O-motif" because it could be mistaken as describing the carboxylic acid only.

The term "in alpha position" is used to describe a directly adjacent position, while the term "in beta position" indicates a neighboring position of an atom or group A and an atom or group B, characterized in that one further atom or group is localized between A and B.

As used herein, the term oxamide refers to the arbitrarily substituted organic compound comprising 2 carbonyl carbons and two nitrogens, which compound is an arbitrarily substituted diamide derived from any oxalic acid.

Those skilled in the art will readily recognize that some of the n-3 PUFA analogues of general formula (I) of the present invention represent "bioisosteres" of the naturally occurring epoxymetabolites produced by cytochrome P450 (CYP) enzymes from omega-3 (n-3) polyunsaturated fatty acids (PUFAs). A bioisostere is a compound resulting from the exchange of an atom or of a group of atoms with an alternative, broadly similar, atom or group of atoms, thereby creating a new compound with similar biological properties to the parent compound. Bioisosterism has, for example, been used by medicinal chemists for improving desired biological or physical properties of a compound, e.g. to attenuate toxicity, modify activity, alter pharmacokinetics and/or metabolism of a compound. For example, the replacement of a hydrogen atom with fluorine at a site of metabolic oxidation in a compound may prevent such metabolism from taking place. Because fluorine is similar in size to the hydrogen atom the overall topology of the molecule is not significantly affected, leaving the desired biological activity unaffected. However, with a blocked pathway for metabolism, said compound may have a longer half-life. Another example is the bioisosteric replacement of carboxylic acid groups which has resulted in analogues showing improved bioavailability, enhanced blood-brain barrier penetration, increased activity, better chemical stability and/or selectivity towards the target (see, e.g. the textbook "The practice of medicinal chemistry", edited by Camille Georges Wermuth, $3^{rd}$ edition, Academic Press, 2008, e.g. p. 303-310; Ballatore C. et al. "Carboxylic Acid (Bio)Isosteres in Drug Design", ChemMedChem 8, 385-395 (2013)). Further, bioisosterism can also be used to provide a "prodrug" of a compound, i.e. a compound that is initially administered to a subject or patient in an inactive (or less active) form, and then becomes modified in vivo to its active form through the normal metabolic processes of the body. For example, conjugation of a compound with lipid and/or sugar units has resulted in analogues (prodrugs) showing increased drug delivery compared to the parent compound (see, e.g. Wong A. and Toth I. "Lipid, Sugar and Liposaccharide Based Delivery Systems", Current Medicinal Chemistry 8, 1123-1136 (2001)).

The n-3 PUFA analogues of general formula (I) of the present invention can be prepared in a number of ways well known to one skilled in the art of organic synthesis. For example, the compounds of the present invention can be synthesized according to the general reaction schemes shown below using synthetic methods known in the art of synthetic organic chemistry, or variations thereon as appreciated by those skilled in the art. Unless indicated otherwise, all variables, e.g. n, k, $R^2$ (also referred to as $R_2$), $R^6$, $R^7$, $R^8$, $R^{41}$, $R^{42}$, $R^{44}$ and $R^{45}$, have the above defined meaning. As starting materials reagents of standard commercial grade can be used without further purification, or can be readily prepared from such materials by routine methods. Those skilled in the art of organic synthesis will recognize that starting materials and reaction conditions may be varied including additional steps employed to produce compounds for use encompassed by the present invention.

The compounds of the present invention are effective for treating, reducing the risk of developing or preventing a disorder associated with neovascularization and/or inflammation. In one embodiment the disorder is a disorder associated with neovascularization. In another embodiment the disorder is a disorder associated with inflammation.

Examples of a disorder associated with inflammation include inflammatory disorders, inflammation caused by other diseases whatever type, etiology or pathogenesis, inflammation caused by inflammatory diseases exemplified below and immunological disorders.

In one embodiment the disorder associated with inflammation is an inflammatory disorder. Examples of inflammatory disorders are acute-phase reaction, local and systemic inflammation.

In one embodiment the disorder associated with inflammation is an immunological disorder. Examples of immunological disorders are hyperesthesia, autoimmune disorders, graft rejection in transplantation, transplant toxicity, granulomatous inflammation/tissue remodelling, myasthenia gravis, immunosuppression, immune-complex diseases, over- and underproduction of antibodies, and vasculitis.

In one embodiment the disorder associated with inflammation is inflammation caused by other diseases whatever type, etiology or pathogenesis, or inflammation caused by inflammatory diseases. Examples of such conditions and diseases include inflammatory bowel disease including Crohn's disease and ulcerative colitis, irritable bowel syndrome, enterocolitis, liver diseases, pancreatitis, nephritis, cystitis (interstitial cystitis), otitis media, peridontitis, inflammatory skin disorders such as psoriasis, eczema, atopic diseases, dermatitis, juvenile or adult onset rheumatoid arthritis and gouty arthritis, ankylosing spondylitis, adult onset or pediatric (systemic onset juvenile idiopathic arthritis) Still's disease, psoriatic arthritis, osteoarthritis and edema associated with burns, sprains or fracture, cerebral edema, angioedema, vasculitis, diabetic vasculopathy, type I diabetes, diabetic nephropathy, diabetic neuropathy, diabetic retinopathy, post capillary resistance or diabetic syndromes associated with insulitis (e.g. hyperglycemia, diuresis, proteinuria and increased nitrite and kallikrein urinary excretion), gall bladder diseases, multiple sclerosis, epilepsy, amyotrophic lateral sclerosis, systemic inflammatory response syndrome (SIRS), ischemia-reperfusion injury and atherosclerosis, septic shock, inflammation caused by anti-hypovolemic and/or anti-hypotensive agents, migraine, gingivitis, osteoporosis, benign prostatic hyperplasia, hyperactive bladder, fibrotic diseases such as pulmonary fibrosis, renal fibrosis, progressive sclerosis and recurrent stricture formation in Crohn's disease, disorders of the respiratory pathways in asthma, atopic or non-atopic asthma, occupational asthma, exercise-induced bronchoconstriction, bronchitis, pneumoconiosis including aluminosis, anhracosis, asbestosis, chalicosis, ptilosis, siderosis, silicosis, tabaccosis and byssinosis, chronic obstructive pulmonary disease including emphysema, adult respiratory distress syndrome, pneumonia, allergic rhinitis, vasomotor rhinitis and pleurisy, auto-inflammatory diseases such as familial Mediterranean fever (FMF), tumor-necrosis factor receptor associated periodic syndrome (TRAPS), neonatal onset multisystem inflammatory disease (NOMID), familial cold autoinflammatory syndrome (FCAS) including familial cold urticaria (FCU), pyogenic arthritis pyoderma gangrenosum acne (PAPA) syndrome and Muckle-Wells disease.

In a preferred embodiment the disorder associated with neovascularization and/or inflammation is an ophthalmological disorder associated with neovascularization, e.g., associated with corneal, retinal, choroidal, uveal, or iris neovascularization and/or an ophthalmological disorder associated with inflammation. A preferred ophthalmological disorder associated with neovascularization is age-related macular degeneration, e.g., neovascular (wet) AMD, or atrophic (dry) AMD. In this embodiment the treatment results in blood vessel regression. In some embodiments, the ophthalmological disorder associated with neovascularization is retinopathy, preferably retinopathy of prematurity (ROP); diabetic retinopathy; diabetic proliferative retinopathy, retinal vein occlusion; e.g. branch retinal vein occlusion, central retinal vein occlusion; sickle cell retinopathy; and radiation retinopathy; Best's disease; or Stargardt's disease. A preferred ophthalmological disorder associated with inflammation is age-related macular degeneration.

In one embodimentthe disorder associated with neovascularization and/or inflammation is not a cardiovascular disease.

In a preferred embodiment, the compound or composition for use according to the invention is administered orally, topically, subcutaneously, intravitrealy, intramuscularly, intraperitoneally, intravenously, or intranasally, preferably orally or intraveneously, more preferably orally or intraperitoneally. The preferred delivery route of ocular medications to the eye for the treatment of an ophthalmological disorder is topical, local ocular (e.g., subconjunctival, intravitreal, retrobulbar, intracameral), and systemic. The latter is preferably achieved through oral, intramuscular or intravenous administration.

It is further preferred that the compound or composition for use according to the invention is a dosage form selected from the group consisting of a spray, an aerosol, a foam, an inhalant, a powder, a tablet, a capsule, a soft gelatin capsule, a tea, a syrup, a granule, a chewable tablet, a salve, a cream, a gel, a suppository, a lozenge, a liposome composition and a solution suitable for injection.

The compound or composition for use according to the invention may further comprise at least one compound of formula (I) and, optionally, one or more carrier substances, e.g. cyclodextrins such as hydroxypropyl p-cyclodextrin, micelles or liposomes, excipients and/or adjuvants. It may additionally comprise, for example, one or more of water, buffers such as, e.g., neutral buffered saline or phosphate buffered saline, ethanol, mineral oil, vegetable oil, dimethylsulfoxide, carbohydrates such as e.g., glucose, mannose, sucrose or dextrans, mannitol, proteins, adjuvants, polypeptides or amino acids such as glycine, antioxidants, chelating agents such as EDTA or glutathione and/or preservatives. Furthermore, one or more other active ingredients may, but need not, be included compositions for us provided herein. For instance, the compounds of the invention may advantageously be employed in combination with an antibiotic, anti-fungal, or anti-viral agent, an anti-histamine, a non-steroidal anti-inflammatory drug, a disease modifying anti-rheumatic drug, an anti-inflammatory drug to treat an auto-immune disease, a cytostatic drug, an antiangiogenic drug or mixtures of the aforementioned. Preferably the drug is an antiangiogenic drug, more preferably an inhibitor of Vascular Endothelial Growth Factor (VEGF) or Vascular Endothelial Growth Factor Receptor (VEGFR).

The compositions for use may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, spinal, intracranial, intrathecal, intraocular, periocular, intraorbital, intrasynovial, intraperitoneal and local ocular (e.g., subconjunctival, intravitreal, retrobulbar, intracameral) injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents such as, e.g., calcium carbonate, sodium carbonate, lactose, calcium phosphate or sodium phosphate, granulating and disintegrating agents such as, e.g., corn starch or alginic acid, binding agents such as, e.g., starch, gelatin or acacia, and lubricating agents such as, e.g., magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed. Methods for preparing such compositions are known (see, for example, H. C. Ansel and N. G. Popovish, Pharmaceutical Dosage Forms and Drug Delivery Systems, 5th ed., Lea and Febiger (1990)).

Formulations for oral use may also be presented as hard gelatin capsules wherein the active ingredient is mixed with an inert solid diluent such as, e.g., calcium carbonate, calcium phosphate or kaolin, or as soft gelatin capsules wherein the active ingredient is mixed with water or an oil medium such as, e.g., peanut oil, liquid paraffin or olive oil.

Aqueous suspensions contain the active ingredient(s) in admixture with excipients suitable for the manufacture of aqueous suspensions. Such excipients include suspending agents suh as, e.g., sodium carboxymethylcellulose, methylcellulose, hydropropylmethylcellulose, sodium alginate, polyvinylpyrrolidone, gum tragacanth and gum acacia; and dispersing or wetting agents such as, e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil such as, e.g., arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Compositions for use may also be in the form of oil-in-water emulsions. The oily phase may be a vegetable oil such as, e.g., olive oil or arachis oil, a mineral oil such as, e.g., liquid paraffin, or a mixture thereof. Suitable emulsifying agents include naturally-occurring gums such as, e.g., gum acacia or gum tragacanth, naturally-occurring phosphatides such as, e.g., soy bean lecithin, and esters or partial esters derived from fatty acids and hexitol, anhydrides such as, e.g., sorbitan monoleate, and condensation products of partial esters derived from fatty acids and hexitol with ethylene oxide such as, e.g., polyoxyethylene sorbitan monoleate. An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Compounds for use according to the invention may be formulated for local or topical administration, such as for topical application to the skin or mucous membranes, such as in the eye. Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols such as, e.g., ethanol or isopropyl alcohol or glycerin; glycols such as, e.g., butylene, isoprene or propylene glycol; aliphatic alcohols such as, e.g., lanolin; mixtures of water and organic solvents and mixtures of organic solvents such as alcohol and glycerin; lipid-based materials such as fatty acids, acylglycerols including oils, such as, e.g., mineral oil, and fats of natural or synthetic origin, phosphoglycerides, sphingolipids and waxes; protein-based materials such as collagen and gelatin; silicone-based materials, both non-volatile and volatile; and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation for use may be prepared in a variety of physical forms including, for example, solids, pastes, creams, foams, lotions, gels, powders, aqueous liquids, emulsions, sprays, eye-drops and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included in a topical formulation include, but are not limited to, abrasives, absorbents, anti-caking agents, anti-foaming agents, anti-static agents, astringents such as, e.g., witch hazel, alcohol and herbal extracts such as chamomile extract, binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%); Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying including mist, aerosol or foam spraying; dropper application; sprinkling; soaking; and rinsing. Controlled release vehicles can also be used, and compositions may be formulated for transdermal administration as a transdermal patch.

A composition for use may be formulated as inhaled formulations, including sprays, mists, or aerosols. Such formulations are particularly useful for the treatment of asthma or other respiratory conditions. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations or compositions suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Compositions for use may also be prepared in the form of suppositories such as e.g., for rectal administration. Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Compositions for use may be formulated as sustained release formulations such as, i.e., a formulation such as a capsule that creates a slow release of modulator following administration. Such formulations may generally be prepared using well known technology and administered by, for example, oral, rectal or subcutaneous implantation, or by implantation at the desired target site.

Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

It will be understood, however, that the specific dose level for any particular patient will depend upon a variety of factors including the activity of the specific compound employed, the age, body weight, general health, sex, diet, time of administration, route of administration, and rate of excretion, drug combination, i.e. other drugs being used to treat the patient, and the severity of the particular disease undergoing therapy.

Preferred compounds of the invention will have certain pharmacological properties. Such properties include, but are not limited to oral bioavailability, such that the preferred oral dosage forms discussed above can provide therapeutically effective levels of the compound in vivo.

n-3 PUFA derivatives provided herein are preferably administered to a patient such as, e.g., a human, orally or parenterally, and are present within at least one body fluid or tissue of the patient.

As used herein, the term "treatment" encompasses both any type of disease-modifying treatment and including symptomatic treatment, i.e., a treatment after the onset of symptoms, either of which may be prophylactic. However, disease-modifying treatment may involve administration before the onset of symptoms, in order to prevent, at least delay or reduce the severity of symptoms after onset. A disease-modifying treatment may also be therapeutic, i.e., after the onset of symptoms, in order to reduce the severity and/or duration of symptoms. A treatment after onset of symptoms may also simply involve stopping progressing of the disease (stable disease). In certain embodiment, the n-3 PUFA derivatives provided herein are administered prophylactically, i.e., before the onset of the disease and/or symptoms, ideally, but not necessarily, to actually prevent the diseases and/or symptoms. It is to be understood that the term prophylaxis and prophylactic in the context of the present invention, simply describes that the compound(s) of the present invention are administered before the onset of symptoms. A prophylactic administration may an administration before the onset of symptoms that are clearly associated with a disease discussed herein: the n-3 PUFA derivatives provided herein may, e.g., be administered to a subject prophylactically when he or she displays certain conditions that may indicate a propensity to develop one of the conditions or diseases that can be treated with one of the n-3 PUFA derivatives of the present invention. Such indicative conditions are, e.g. high blood pressure or diabetes. Such a prophylactic treatment is called primary prophylaxis. In another embodiment, the n-3 PUFA derivatives provided herein may be administered to a subject prophylactically when he or she has previously suffered from a condition or disease that can be treated with the n-3 PUFA derivatives of the present invention, but currently does not display any symptoms. Such a prophylactic treatment is called secondary prophylaxis. Patients receiving the n-3 PUFA derivatives for the purpose of primary or secondary prophylaxis are considered to be in need of such a treatment. Patients may include but are not limited to mammals, especially humans, domesticated companion animals such as dogs, cats, horses, and livestock such as cattle, pigs, sheep, with dosages as described herein.

The activity of the n-3 PUFA analogues according to the invention can, for example, be determined in appropriate in vitro and/or in vivo assays. For instance, the biological activity of the n-3 PUFA analogues according to the present invention may be determined using the established cell model of Kang and Leaf (*Proc Natl Acad Sci USA*, 1994. 91 (21): p. 9886-90.) known to those skilled in the art.

The following figure and examples serve to illustrate the invention and are not intended to limit the scope of the invention as described in the appended claims.

FIGURES

Figure 2:
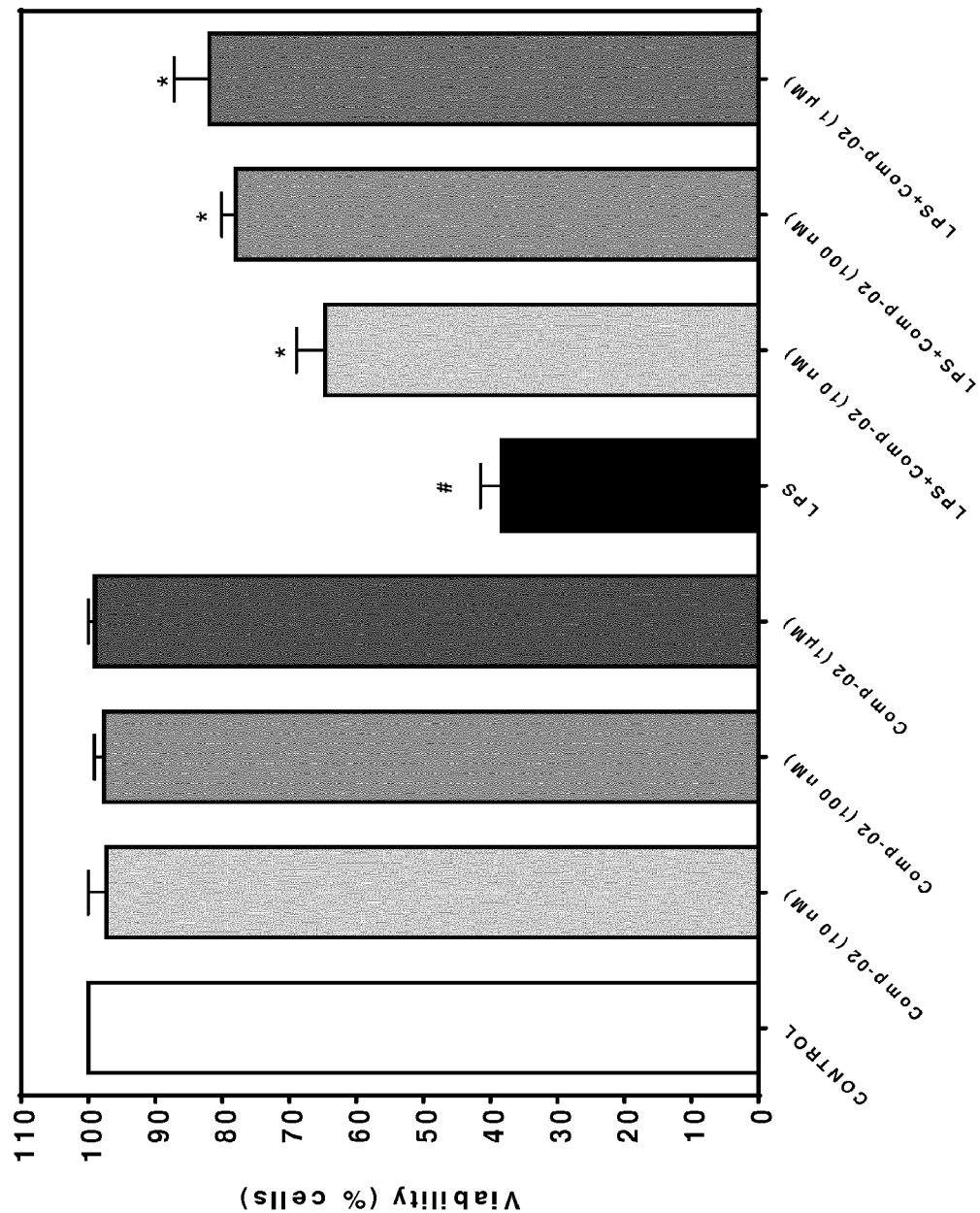

FIG. 1: Efficacy of compound with the structure according to Formula (VI), which is referred to as "Compound 1" in a laser induced choroidal neovascularization model in rat evaluated by measuring vascular leakage using fluorescence angiography:
Fluorescence angiography grading data (mean±SD) on day 14 and 21 after induction of choroidal neovascularization (laser burn), grading scale: 0-3 arbitrary unit. The leakage of fluorescein was evaluated in the fluorescence angiograms by two independent examiners masked to the study groups and graded as follows: Score 0: no leakage; Score 1: slightly stained; Score 2: moderately stained; Score 3: strongly stained, n=10 animals/group with 6 lesions per animal, statistic: Kruskal-Wallis-test and Dunn's multiple comparisons test, * p<0.05, po: oral administration, ip: intraperitoneal administration, IVT: intravitreal administration, FA: Fluorescence angiography FIG. 2: FIG. 2 shows the anti-inflammatory effect of a metabolically robust analog of 17,18-EEQ (Comp-02) on HL-1 cardiomyocytes. A cardiomyocyte cell line was used (mouse derived immortalized cardiomyocytes, HL-1 cells). Cells were either treated with vehicle (0.01% ethanol) or different concentrations of test compound (Comp-02: cE=10 nM, 100 nM or 1 μM). Simultaneously, the cells were challenged with 1 μg/mL lipopolysaccharide (LPS). After 24 h of incubation, the cells were processed to measure viability.

Figure 3:
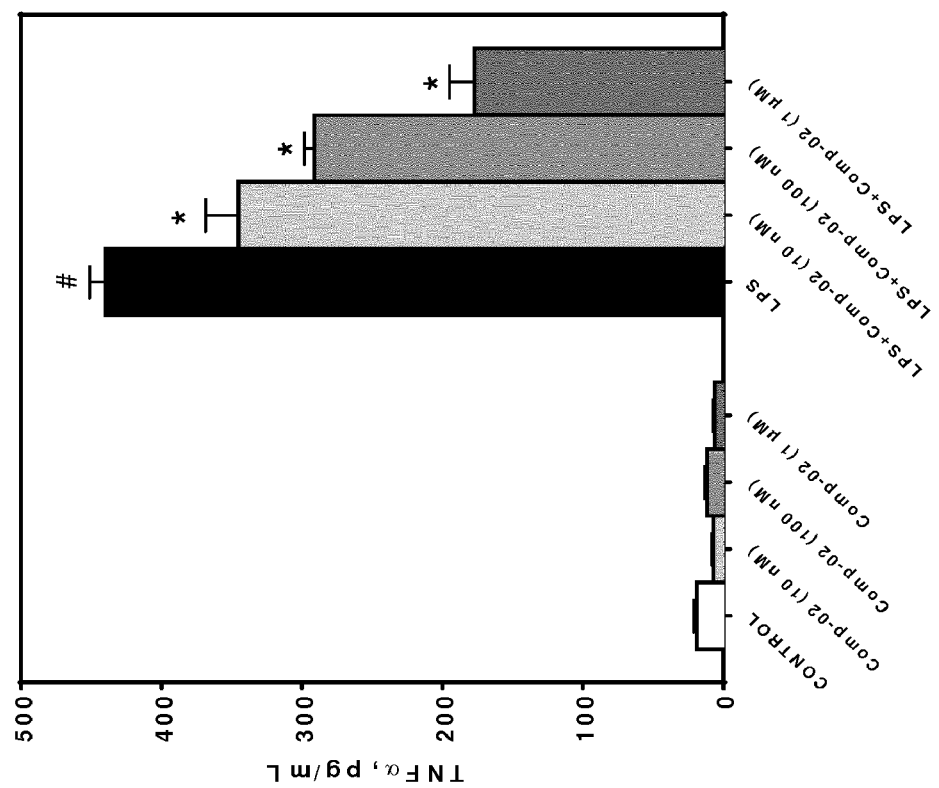

FIG. 3: FIG. 3 shows the anti-inflammatory effect of a metabolically robust analog of 17,18-EEQ (Comp-02) on HL-1 cardiomyocytes. A cardiomyocyte cell line was used (mouse derived immortalized cardiomyocytes, HL-1 cells). Cells were either treated with vehicle (0.01% ethanol) or different concentrations of test compound (Comp-02: cE=10 nM, 100 nM or 1 μM). Simultaneously, the cells were challenged with 1 μg/mL lipopolysaccharide (LPS). After 24 h of incubation, the cells were processed to measure release of the pro-inflammatory cytokine TNF alpha.

Figure 4:
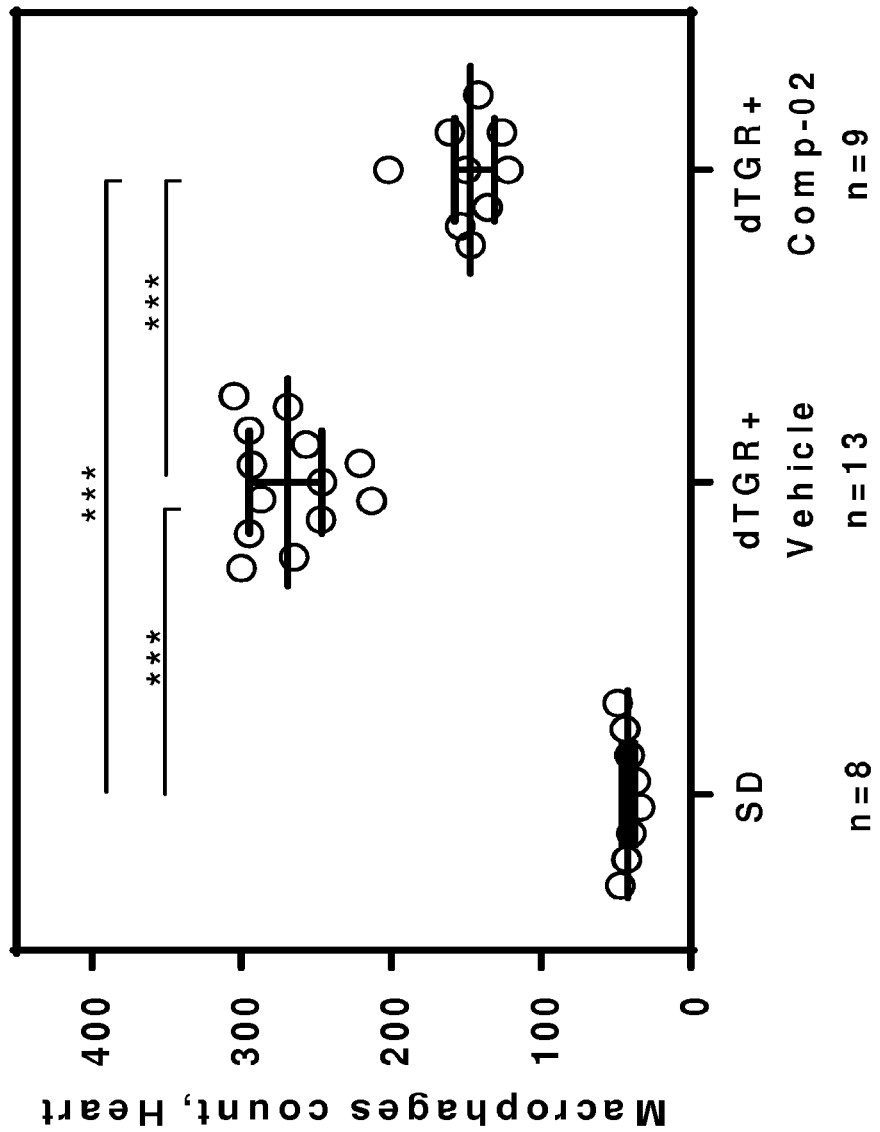

FIG. 4: FIG. 4 shows the inhibitory effect of a metabolically robust analog of 17,18-EEQ (Comp-02) on cardiac inflammation in a rat model of severe hypertension and end-organ damage. Modulation of inflammation was measured with macrophages infiltration via ED1 staining as a marker for inflammation. The values shown are expressed as median with interquartile range. Count values are pooled in bins of 20 view fields. The results show that dTGR animals have significant higher amounts of infiltrated macrophages in the cardiac tissue compared to non-treated SD animals. However, Comp-02 treatment led to a significant reduction of macrophage infiltration (ED1 positive cells) in dTGR animals compared to vehicle treated dTGRs.

FIG. 5: FIG. 5 shows the inhibitory effect of a metabolically robust analog of 17,18-EEQ (Comp-02) on renal inflammation in a rat model of severe hypertension and end-organ damage. Modulation of inflammation was measured with macrophages infiltration via ED1 staining as a marker for inflammation. The values shown are expressed as median with interquartile range. Count values are pooled in bins of 20 view fields. The results show that dTGR animals have significant higher amounts of infiltrated macrophages in the renal tissue compared to non-treated SD animals. However, Comp-02 treatment led to a significant reduction of macrophage infiltration (ED1 positive cells) in dTGR animals compared to vehicle treated dTGRs.

EXAMPLE 1 SYNTHESIS OF COMPOUNDS

In the following the synthesis of selected compounds of the invention is illustrated.

Compound 1 (Comp-01)

Synthesis of compound 1 (Comp-01) was analogous to synthesis of compound 3 (Comp-03), while the urea-group was introduced following the synthetic route described in patent application WO2010/081683 (example 13).

Compound 2 (Comp-02)

Summary of Synthesis

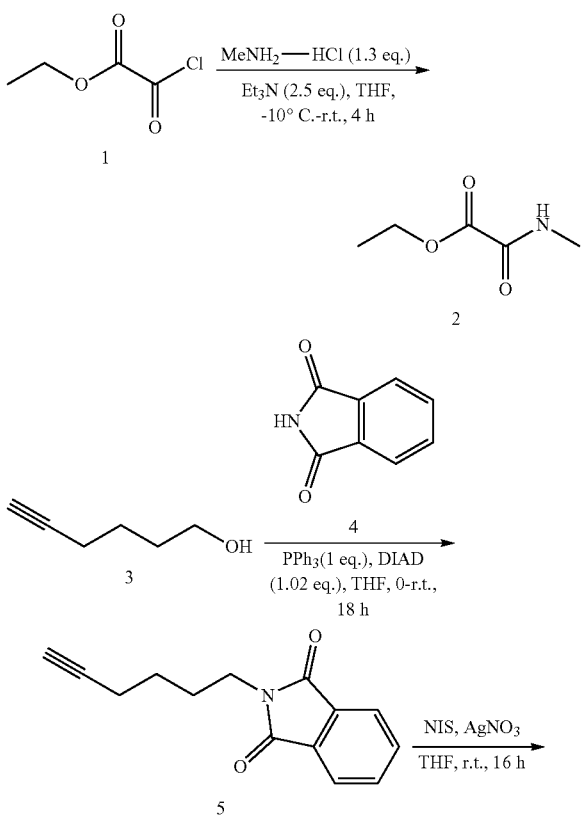

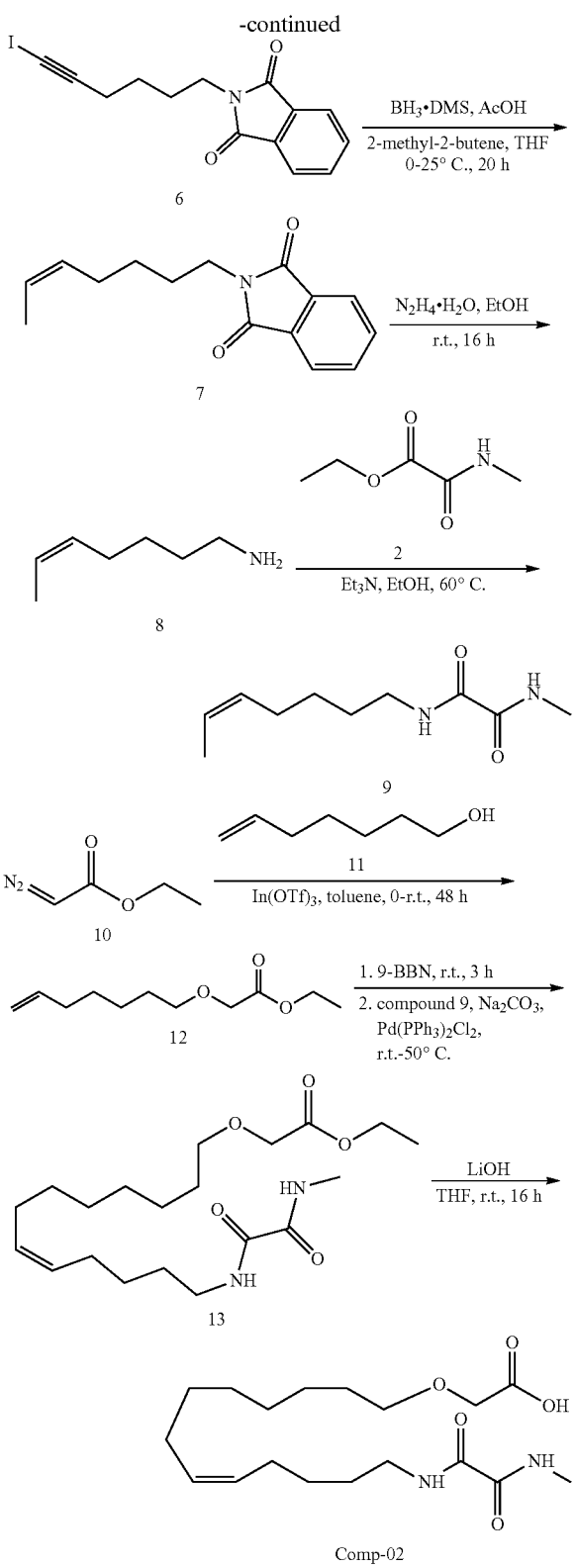

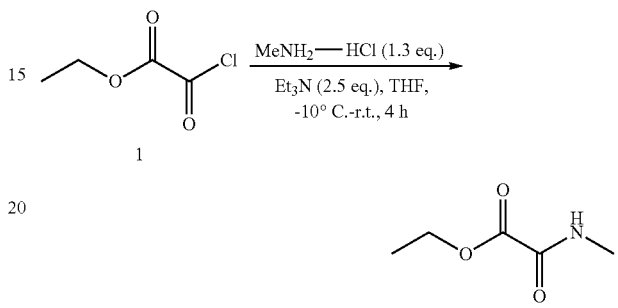

2010 (Column: sepax ODS 50×2.0 mm, 5 um) or Agilent 1200 HPLC, 1956 MSD (Column: Shim-pack XR-ODS 30×3.0 mm, 2.2 um) operating in ES (+) ionization mode. Chromatographic purifications were by flash chromatography using 100~200 mesh silica gel. Anhydrous solvents were pre-treated with 3A MS column before used. All commercially available reagents were used as received unless otherwise stated.

General Procedure for Preparation of Compound 2

| Reagent | MW. | Amount | Mmol | ratio | Other Info. |
|---|---|---|---|---|---|
| Compound 1 | 136.53 | 100 g | 732.44 | 1 | |
| MeNH$_2$—HCl | 67.52 | 64.29 g | 952.17 | 1.3 | |
| Et$_3$N | 101.19 | 185.29 g | 1830 | 2.5 | |
| THF | | 2 L | | | |
| Product (compound 2) | 131.13 | 70 g | 533.82 | | Yield: 73% |

Methanamine (64.29 g, 952.17 mmol, 1.30 Eq) in 500 mL THF was added Et$_3$N (75 g, 732.44 mmol), the solution was added to Compound 1 (100.00 g, 732.44 mmol, 1.00 eq), Et$_3$N (111 g, 1.1 mol) in THF (1.5 L) at −10° C. And the mixture was stirred at 25° C. for 16 h. Then the mixture was filtered, the filtrate was washed with 2N HCl (500 mL), extracted with EA (300 mL*4), concentrated and purified by silica gel (PE:EA=3:1 to 1:1) to afford Compound 2 (70.00 g, 533.82 mmol, 72.88% yield) as a yellow oil.

TLC Information (PE:EtOAc=2:1); R$_f$(Comp-02)=0.39; LCMS: ET2662-1-P1A (M+H$^+$): 131.7; $^1$H NMR (CDCl$_3$, 400 MHz) 4.36~4.24 (q, J=8 Hz, 2H), 2.93~2.85 (d, J=4 Hz, 3H), 1.38~1.30 (t, J=8 Hz, 3H)

General Procedure for Preparation of Compound 4

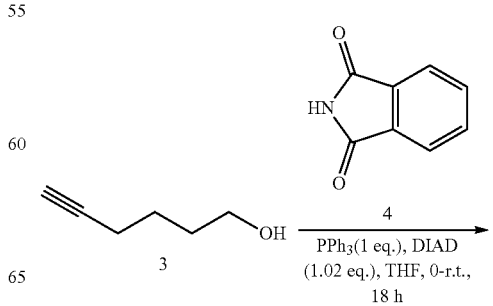

General Method

NMR spectra were recorded on Bruker Avance 400 MHz for $^1$HNMR and 100 MHz for $^{13}$CNMR. LCMS were taken on a quadrupole Mass Spectrometer on Shimadzu LCMS

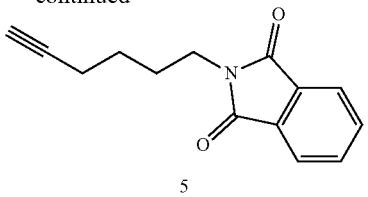

| Reagent | MW. | amount | mmol | ratio | Other Info. |
|---|---|---|---|---|---|
| Compound 3 | 98.14 | 47.5 g | 484 | 1 | |
| Compound 4 | 147.13- | 78.33 g | 532.4 | 1.1 | |
| PPh$_3$ | 262.29 | 133.3 g | 508.2 | 1.05 | |
| DIAD | 202.21 | 107.66 g | 532.4 | 1.1 | |
| THF | | 1.8 L | | | |
| Product (compound 5) | 227.26 | 42.5 g | 374.02 | | Yield 77.3% |

A solution of Compound 3 (47.50 g, 484.00 mmol, 1.00 eq.) and DIAD (107.66 g, 532.40 mmol, 1.10 eq.) in anhydrous THF (50 mL) was slowly added via cannula to a 0° C. solution of Compound 4 (78.33 g, 532.40 mmol, 1.10 eq.) and PPh$_3$ (133.30 g, 508.20 mmol, 1.05 eq.) in anhydrous THF (100 mL). The flask and cannula were washed with an additional portion of dry THF (30 mL) to ensure complete addition. The reaction was allowed to gradually warm to 25° C. and stirred for 18 h. Then H$_2$O (1000 mL) was added, extracted with EA (500 mL*2), concentrated and purified by silica gel (PE:EA=0-10:1) to give Compound 5 (42.5 g, 374.02 mmol, 77.28% yield) as a white solid.

TLC Information (PE:EtOAc=5:1); R$_f$ (Comp-03)=0.2; R$_f$(Comp-05)=0.5; 1H NMR (CDCl$_3$, 400 MHz) 7.86~7.79 (m, 2H), 7.72~7.67 (m, 2H), 3.73~3.66 (t, J=8 Hz, 2H), 2.27~2.20 (m, 2H), 1.95~1.91 (t, J=4 Hz, 1H), 1.85~1.75 (m, 2H), 1.61~1.52 (m, 2H)

General Procedure for Preparation of Compound 6

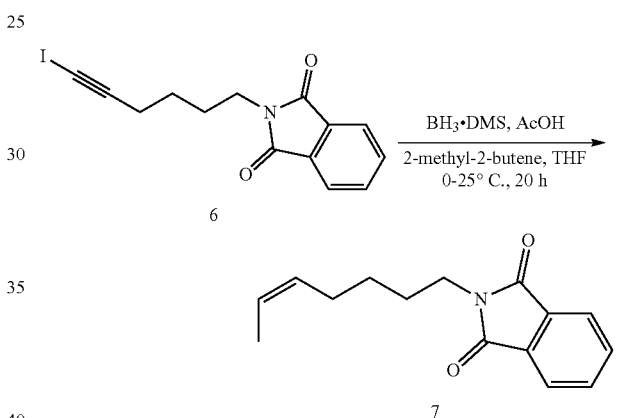

| Reagent | MW. | amount | mmol | ratio | Other Info. |
|---|---|---|---|---|---|
| Compound 5 | 227.26 | 88 g | 387.22 | 1 | |
| NIS | 224.98 | 130.68 g | 580.83 | 1.5 | |
| AgNO$_3$ | 169.87 | 16.44 g | 96.81 | 0.25 | |
| THF | | 1.6 L | | | |
| Product (Compound 6) | 353.15 | 118.6 g | 335.8 | | Yield: 86% |

NIS 130.68 g, 580.83 mmol, 1.50 eq. was added in one portion to a solution of Compound 5 (88.00 g, 387.22 mmol, 1.00 eq.) and AgNO$_3$ (16.44 g, 96.81 mmol, 0.25 eq.) in anhydrous THF (1600 mL) at 25° C. The reaction head space was flushed with N$_2$ and the reaction mixture was protected from light with an aluminum foil wrap and stirred for 16 h. The mixture was poured into water (1000 mL), extracted with EA (600 mL*3), concentrated and purified by silica (PE:EA=10:1 to 2:1) to give Compound 6 (118.6 g, 1.01 mol, 86.78% yield) as a white solid.

TLC Information (PE:EtOAc=20:1); R$_f$(Comp-05)=0.22; R$_f$(Cpd 6)=0.21; $^1$H NMR (CDCl$_3$, 400 MHz) 7.87~7.82 (m, 2H), 7.74~7.69 (m, 2H), 3.74~3.67 (t, J=8 Hz, 2H), 2.45~2.39 (t, J=8 Hz, 2H), 1.84~1.74 (m, 2H), 1.61~1.52 (m, 2H)

General Procedure for Preparation of Compound 7

| Reagent | MW. | amount | mmol | ratio | Other Info. |
|---|---|---|---|---|---|
| Compound 6 | 353.15 | 157 g | 444.57 | 1 | |
| BH$_3$•DMS | | 58 mL | 577.94 | 1.3 | |
| 2-methyl-2-butene | 70.13 | 87.3 g | 1240 | 2.8 | |
| AcOH | | 260 mL | | | |
| THF | | 1.2 L | | | |
| Product (compound 5) | 355.17 | 135 g | 380.1 | | Yield: 85% |

2-methylbut-2-ene (87.30 g, 1.24 mol, 2.80 eq.) was added over 30 min to a 0° C. solution of BH3·Me2S (43.91 g, 577.94 mmol, 1.30 eq.) in THF (300 mL). After 1 h, the reaction mixture was warmed to 25° C. and stirred for 90 min. After re-cooling to 0° C., a solution of Compound 6 (157.00 g, 444.57 mmol, 1.00 eq.) in THF (900 mL) was added slowly over 1 h. Upon complete addition, the cold bath was removed and the reaction mixture was stirred at 25° C. After 2 h, the reaction was cooled again to 0° C. where upon glacial AcOH (260 mL) was added slowly over 30 min (Caution: gas evolution) and stirred at 25° C. for 16 h. TLC (PE:EA=10:1) show the reaction was completed, the mixture was pour into water (1 L), extracted with EA (300 mL*2), concentrated and purified by silica gel(PE:EA=0-10:1) to give Compound 7 (135 g, 380.1 mmol, 85.50% yield) as a yellow oil.

TLC Information (PE:EtOAc=10:1); $R_f$ (Cpd 6)=0.5; $R_f$ (Cpd 7)=0.55; $^1$H NMR: (CDCl$_3$, 400 MHz) 7.88~7.80 (m, 2H), 7.75-7.67 (m, 2H), 6.24~6.11 (m, 2H), 3.74~3.66 (t, J=8 Hz, 2H), 2.24~2.15 (q, J=8 Hz, 2H), 1.78-1.67 (m, 2H), 1.55-1.44 (in, 2H)

General Procedure for Preparation of Compound 8

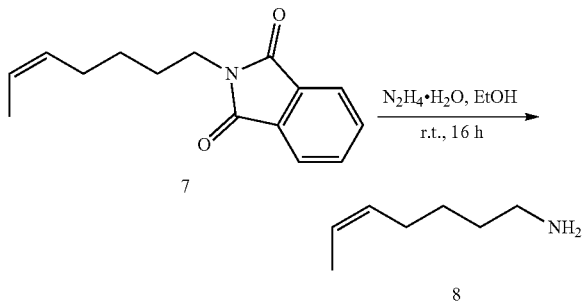

| Reagent | MW. | amount | mmol | ratio | Other Info. |
|---|---|---|---|---|---|
| Compound 7 | 355.17 | 138 g | 388.55 | 1 | |
| N$_2$H$_4$·H$_2$O | 50.06 | 97.25 g | 1940 | 5 | |
| MeOH | | 2 L | | | |
| Product (compound 8) | 225.07 | 81 g | 683.79 | | Yield: 92% |

N$_2$H$_4$·H$_2$O (97.25 g, 1.94 mol, 5.00 eq.) was added to a solution of Compound 7 (138.00 g, 388.55 mmol, 1.00 eq) in anhydrous MeOH (2.00 L) at 0° C. and stirred at 25° C. for 18 h, TLC (PE:EA=10:1) show the reaction was completed, the reaction mixture was concentrated, the residue was poured into DCM (5000 mL) and stirred for 30 mins. Filtered and the filter cake was washed with DCM (1 L*2), the filtrate was concentrated to give Compound 8 (162.00 g, crude) as a yellow oil.

TLC Information (PE:EtOAc=10:1); $R_f$ (Cpd 7)=0.5; $R_f$ (Cpd 8)=0; TLC Information (DCM:MeOH=10:1); $R_f$ (Cpd 7)=1; $R_f$ (Cpd 8)=0.2; $^1$H NMR: (CDCl$_3$, 400 MHz) 6.19~6.07 (m, 2H), 2.73~2.59 (m, 2H), 2.20~2.05 (m, 2H), 1.75~1.55 (m, 2H), 1.51~1.36 (m, 4H)

General Procedure for Preparation of Compound 9

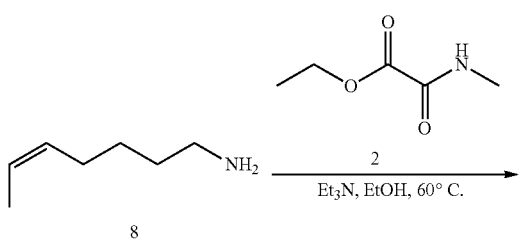

| Reagent | MW. | amount | mmol | ratio | Other Info. |
|---|---|---|---|---|---|
| Compound 8 | 225.07 | 92 g | 408.76 | 1 | |
| Compound 2 | 131.13 | 53.6 g | 408.76 | 1 | |
| Et$_3$N | 101.19 | 49.64 g | 590.51 | 1.2 | |
| EtOH | | 1.5 L | | | |
| Product (compound 9) | 310.13 | 90 g | 232.16 | | Yield: 57% |

Compound 8 (92.00 g, 408.76 mmol, 1.00 eq) Compound 2 (53.60 g, 408.76 mmol, 1.00 eq) and Et$_3$N (49.64 g, 490.51 mmol, 1.20 eq) in anhydrous ethanol (1.5 L) was heated at 60° C. for 20 h. TLC (DCM:MeOH=10:1) show the reaction was completed, the mixture was concentrated to about 300 mL. Filtered and concentrated to give Compound 9 (90 g, 232.16 mmol, 57% yield) as a white solid.

TLC Information (DCM:MeOH=10:1); $R_f$ (Cpd 8)=0.2; $R_f$ (Cpd 9)=0.5; $^1$H NMR: (CDCl$_3$, 400 MHz) 7.57~7.37 (s, 2H), 6.25~6.20 (d, J=8 Hz, 1H), 6.18~6.11 (q, J=8 Hz, 1H), 3.37-3.30 (q, J=8 Hz, 2H), 2.93~2.88 (d, J=4 Hz, 3H), 2.21~2.13 (m, 2H), 1.66~1.56 (m, 2H), 1.53~1.43 (m, 2H)

General Procedure for Preparation of Compound 12

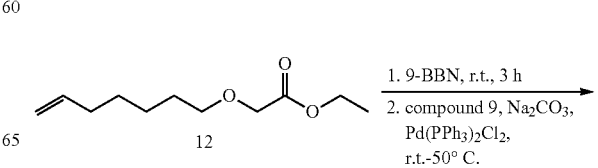

| Reagent | MW. | amount | mmol | ratio | Other Info. |
|---|---|---|---|---|---|
| Compound 10 | 114.1 | 25 g | 197.2 | 1 | 90% |
| Compound 11 | 114.18 | 27.02 g | 236.63 | 1.2 | |
| In(OTf)$_3$ | 560 | 22.09 g | 39.44 | 0.2 | |
| toluene | | 350 mL | | | |
| Compound 12 | 200.27 | 35 g | 139.81 | | Yield: 71% |

Compound 10 (25.00 g, 197.20 mmol, 1.00 eq.) in toluene (75 mL) was added to a solution of Compound 11 (27.02 g, 236.63 mmol, 1.20 eq.) In (OTf)$_3$ (22.09 g, 39.44 mmol, 0.20 eq) in toluene (275 mL) over 20 mins. Then the mixture was stirred at 25° C. for 48 h. The mixture was concentrated and purified by silica gel (PE:EA=20:1) to give ethyl Compound 12 (35.00 g, 139.81 mmol, 70.90% yield, 80% purity) as a yellow oil.

TLC Information (PE:EtOAc=10:1); $R_f$ (Cpd 11)=0.21; $R_f$(Cpd 12)=0.55; $^1$H NMR: (CDCl$_3$, 400 MHz) 5.86~5.72 (m, 1H), 5.03~5.86 (m, 2H), 4.24~4.17 (q, J=8 Hz, 2H), 4.07~4.01 (s, 2H), 3.54~3.47 (t, J=8 Hz, 2H), 2.09~1.98 (m, 2H), 1.68~1.55 (m, 2H), 1.45~1.32 (m, 4H), 1.30~1.25 (t, J=8 Hz, 3H)

General Procedure for Preparation of Compound 13

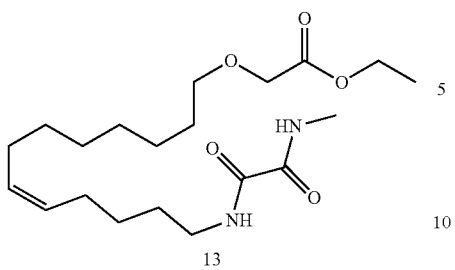

13

| Reagent | MW. | amount | mmol | ratio | Other Info. |
|---|---|---|---|---|---|
| Compound 12 | 200.27 | 10.07 g | 50.3 | 1.2 | 90% |
| Compound 9 | 310.13 | 13 g | 41.92 | 1 | |
| 9-BBN | | 100.6 mL | 100.6 | 2.4 | |
| Na$_2$CO$_3$ | | 200 mL | | | 2M |
| Pd(PPh$_3$)$_2$Cl$_2$ | 701.9 | 1.47 g | 2.1 | 0.05 | |
| THF | | 800 mL | | | |
| Compound 13 | 384.51 | 6.5 g | 16.06 | | Yield: 38% |

To an oven-dried as containing 9-BBN (17.53 g, 100.60 mmol, 2.40 eq) in THF (540 mL) was added a solution of Compound 12 (10.07 g, 50.30 mmol, 1.20 eq) in THF (60 mL) at 0° C. After stirring at 25° C. for 16 h, an aqueous solution of Na$_2$CO$_3$ (200 mL of 2 M soln prepared from argon sparged H$_2$O) was added. After 2 h, Pd(PPh$_3$)$_2$Cl$_2$ (1.47 g, 2.10 mmol, 0.05 eq) was added followed by Compound 9 (13.00 g, 41.92 mmol, 1.00 eq) dissolved in THF (200 mL). The resulting red solution was protected from light. The reaction was stirred at 50° C. for 5 h. LCMS show the reaction was completed. After cooling to 25° C., the reaction mixture was concentrated in vacuo and the residue was purified by silica gel (PE:EA=10:1 to 3:1) to give Compound 13 (6.5 g, 16.06 mmol, 38.31% yield, 95% purity) as a yellow solid.

TLC Information (PE:EtOAc=2:1); R$_f$ (Cpd 12)=0.3; R$_f$ (Cpd 13)=0.3; LCMS: ET2662-38-P1D (M+H$^+$): 385.1; $^1$H NMR: (CDCl$_3$, 400 MHz) ☐7.57~7.38 (s, 1H), 5.41~5.25 (m, 2H), 4.25~4.17 (q, J=8 Hz, 2H), 4.07~4.02 (s, 2H), 3.54~3.47 (t, J=8 Hz, 2H), 3.34~3.26 (q, J=8 Hz, 2H), 2.92~2.87 (d, J=8 Hz, 3H), 2.08~1.94 (m, 4H), 1.65~1.51 (m, 4H), 1.43~1.23 (m, 13H)

General Procedure for Preparation of Comp-02

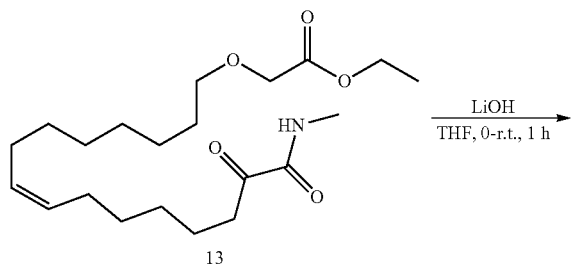

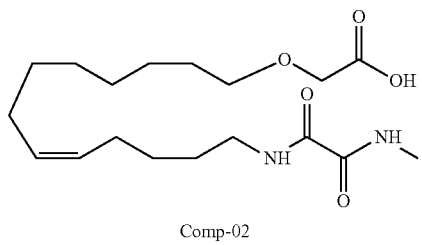

Comp-02

| Reagent | MW. | amount | mmol | ratio | Other Info. |
|---|---|---|---|---|---|
| Compound 13 | 384.51 | 7.5 g | 19.51 | 1 | 90% |
| LiOH | 23.95 | 0.9341 g | 39.02 | 2 | |
| H$_2$O | | 40 mL | | | |
| THF | | 70 mL | | | |
| Compound 13 | 356.46 | 4 g | 10.72 | | Yield: 55% |

To a solution of Compound 13 (7.50 g, 19.51 mmol, 1.00 eq.) in THF (70.00 mL) was added LiOH (934.31 mg, 39.02 mmol, 2.00 eq.) in H$_2$O (40.00 mL) at 0° C. and then the reaction mixture was stirred at 0-25° C. for 1 h. LCMS show the reaction was completed. Then H$_2$O (60 mL) was added to the reaction mixture, the aqueous phase was treated with 3 N HCl (10 mL) to pH=3-4, extracted with EA (100 mL*3), dried, the organic phase was concentrated to give crude product. The residue was purified by column on gel (PE:EA=5:1 to EA) to give Comp-02 (4.00 g, 10.72 mmol, 54.95% yield, 95.51% purity)

TLC Information (DCM:MeOH=10:1); R$_f$ (Cpd 13)=0.9; R$_f$(Comp-02)=0.4; MS: ET2662-43-P1C (M+Na$^+$): 379.2; $^1$H NMR (CDCl$_3$, 400 MHz) 7.84 (s, 1H), 7.74 (s, 1H), 5.40~5.32 (m, 2H), 4.11 (s, 2H), 3.59~3.55 (t, J=6.4 Hz, 2H), 3.35~3.32 (t, J=6.8 Hz, 2H), 2.92~2.91 (d, J=5.2 Hz, 3H), 2.07~2.00 (m, 4H), 1.64-1.59 (m, 4H), 1.42~1.32 (m, 10H); $^{13}$C NMR (CDCl3, 100 MHz) δ 173.7, 160.7, 159.8, 130.5, 129.0, 72.0, 67.8, 39.7, 29.4, 29.3, 29.0, 29.0, 28.6, 27.1, 26.8, 26.7, 25.8

Compound 3 (Comp-03)

Summary of Synthesis

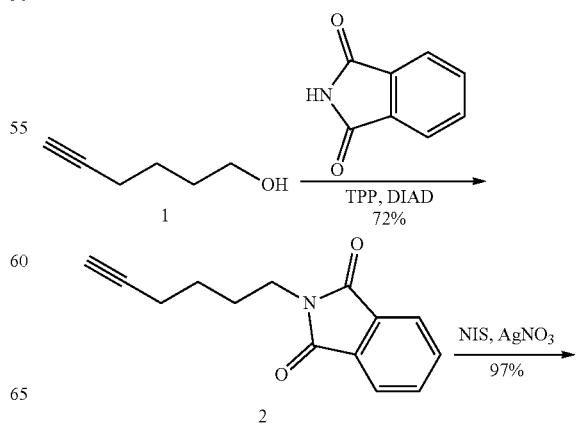

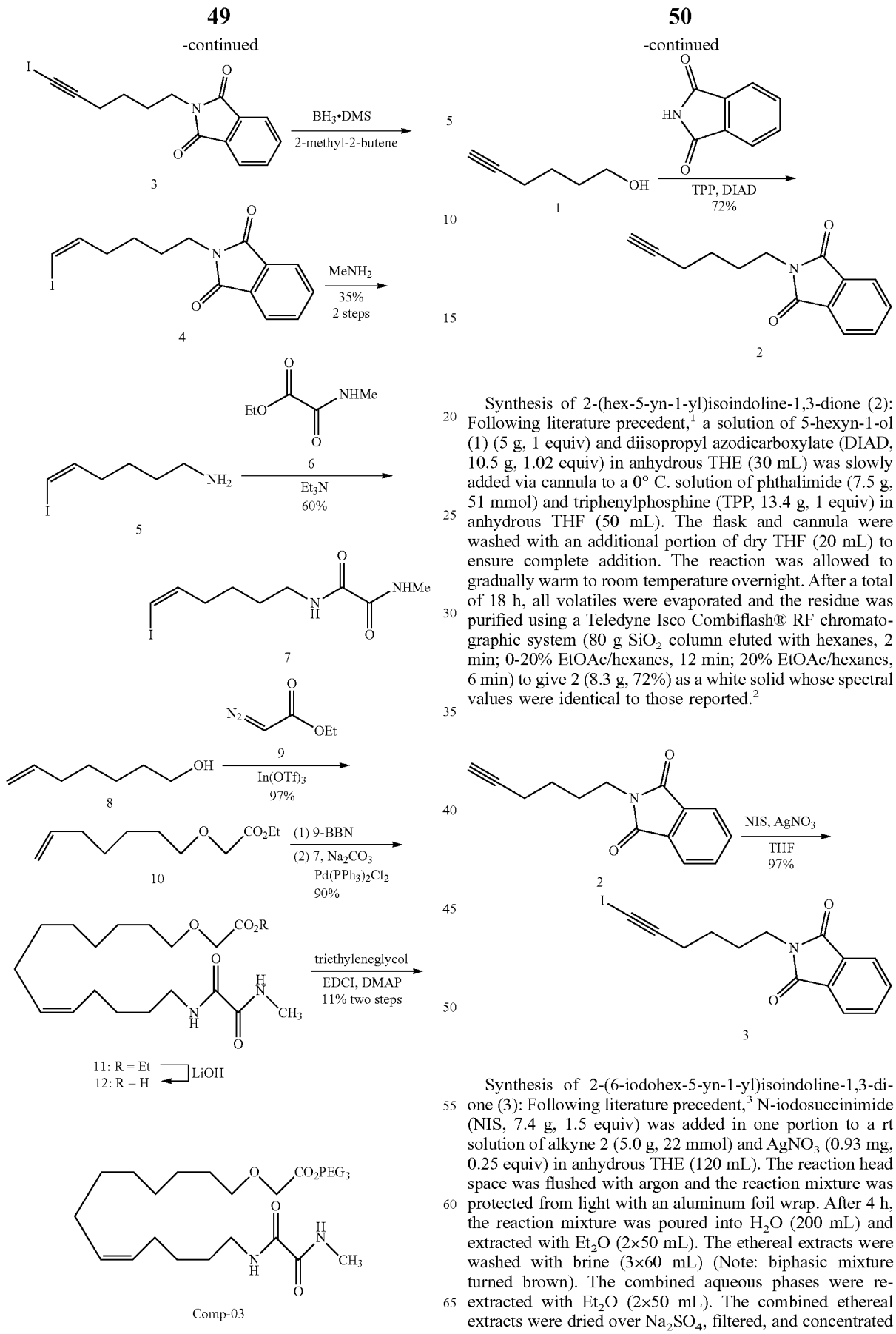

Synthesis of 2-(hex-5-yn-1-yl)isoindoline-1,3-dione (2): Following literature precedent,[1] a solution of 5-hexyn-1-ol (1) (5 g, 1 equiv) and diisopropyl azodicarboxylate (DIAD, 10.5 g, 1.02 equiv) in anhydrous THF (30 mL) was slowly added via cannula to a 0° C. solution of phthalimide (7.5 g, 51 mmol) and triphenylphosphine (TPP, 13.4 g, 1 equiv) in anhydrous THF (50 mL). The flask and cannula were washed with an additional portion of dry THF (20 mL) to ensure complete addition. The reaction was allowed to gradually warm to room temperature overnight. After a total of 18 h, all volatiles were evaporated and the residue was purified using a Teledyne Isco Combiflash® RF chromatographic system (80 g $SiO_2$ column eluted with hexanes, 2 min; 0-20% EtOAc/hexanes, 12 min; 20% EtOAc/hexanes, 6 min) to give 2 (8.3 g, 72%) as a white solid whose spectral values were identical to those reported.[2]

Synthesis of 2-(6-iodohex-5-yn-1-yl)isoindoline-1,3-dione (3): Following literature precedent,[3] N-iodosuccinimide (NIS, 7.4 g, 1.5 equiv) was added in one portion to a rt solution of alkyne 2 (5.0 g, 22 mmol) and $AgNO_3$ (0.93 mg, 0.25 equiv) in anhydrous THF (120 mL). The reaction head space was flushed with argon and the reaction mixture was protected from light with an aluminum foil wrap. After 4 h, the reaction mixture was poured into $H_2O$ (200 mL) and extracted with $Et_2O$ (2×50 mL). The ethereal extracts were washed with brine (3×60 mL) (Note: biphasic mixture turned brown). The combined aqueous phases were re-extracted with $Et_2O$ (2×50 mL). The combined ethereal extracts were dried over $Na_2SO_4$, filtered, and concentrated on a rotary evaporator. The residue was purified using a Teledyne Isco Combiflash® RF chromatographic system (80 g SiO2 column eluted with hexanes, 2 min; 0-40% EtOAc/hexanes, 8 min; 40% EtOAc/hexanes, 10 min; 40-100% EtOAc/hexanes, 5 min; 100%, EtOAc, 3 min) to give 3 (97%) as a white solid, mp 132.5-132.7° C. $^1$H NMR (500 MHz, CDCl$_3$) δ 7.85 (ddd, J=5.4, 3.0, 1.0 Hz, 2H), 7.72 (ddd, J=5.5, 3.0, 1.0 Hz, 2H), 3.71 (t, J=7.1 Hz, 2H), 2.42 (t, J=7.0 Hz, 2H), 1.83-1.73 (m, 2H), 1.61-1.51 (m, 2H); $^{13}$C NMR (100 MHz, CDCl$_3$) δ 168.62, 134.14, 132.30, 123.44, 94.04, 37.60, 27.91, 25.89, 20.60, −6.27.

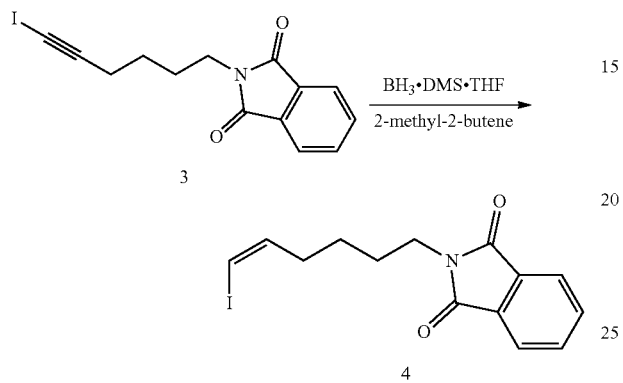

Synthesis of 2-(6-iodohex-5(Z)-en-1-yl)isoindoline-1,3-dione (4): Following literature precedent,[4] neat 2-methyl-2-butene (4.2 mL, 2.8 equiv) was added over 5 min to a 0° C. solution of BH$_3$·Me$_2$S (2.0 M in THF, 9.2 mL, 1.3 equiv) in THF (3 mL). After 1 h, the reaction mixture was warmed to room temperature and stirred for 90 min. After re-cooling to 0° C., a solution of iodoalkyne 3 (5 g, 1 equiv) in THF (30 mL) was added slowly over 5 min. Upon complete addition, the cold bath was removed and the reaction mixture was stirred at rt. After 2 h, the reaction was cooled again to 0° C. whereupon glacial AcOH (8.5 mL) was added slowly over 5 min (Caution: gas evolution). After stirring overnight (14 h), the reaction mixture was diluted with H$_2$O (20 mL), then carefully poured into a stirring, saturated sodium bicarbonate solution (40 mL). The biphasic mixture was extracted with ether (2×40 mL) and the combined ethereal extracts were washed with water, brine, dried over anhydrous MgSO$_4$, filtered, and concentrated in vacuo. The residue was purified using a Teledyne Isco Combiflash® RF chromatographic system (40 g SiO$_2$ column eluted with 0-20% EtOAc/hexanes, 8 min; 20% EtOAc/hexanes, 6 min) to give a mixture (4.52 g) of 4 and borane side-product. Further purification was postponed until the next step.

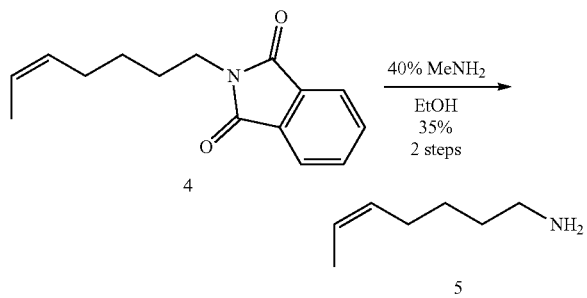

Synthesis of 6-iodohex-5(Z)-en-1-amine (5): Following literature precedent,[5] 40% wt MeNH$_2$ in H$_2$O (15 mL) was added to a rt solution of crude 4 (4.52 g) in anhydrous EtOH (20 mL). After stirring overnight (18 h), the reaction mixture was poured into ice water (100 mL) and extracted with Et$_2$O (30 mL×2). The combined ethereal extracts were washed with cold 1N HCl solution (20 mL×2). The combined aqueous washes were adjusted to pH 8 with dilute, aq. NaOH. The solution was extracted with Et$_2$O (30 mL×2), dried over anhydrous Na$_2$SO$_4$, filtered, and concentrated in vacuo to give crude 5 (1.12 g) as a brown oil that was used in the next step without further purification. $^1$H NMR (500 MHz, CDCl$_3$) δ 6.29-6.08 (m, 2H), 2.71 (tt, J=7.0, 1.8 Hz, 2H), 2.16 (app q, J=6.5 Hz, 2H), 1.78-1.52 (m, 2H).

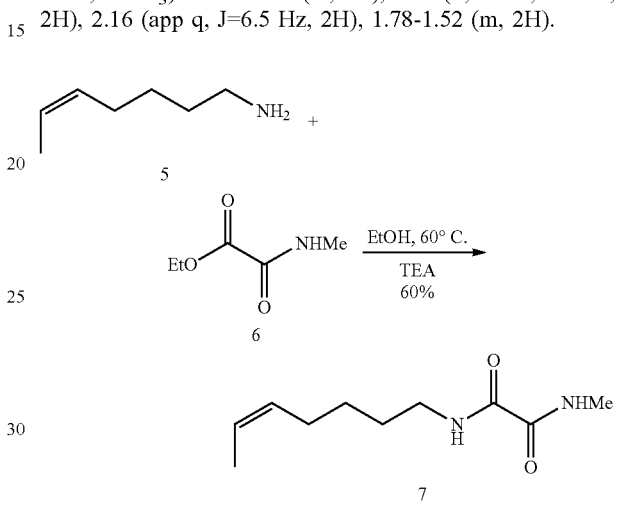

Synthesis of N$^1$-(6-iodohex-5(Z)-en-1-yl)-N$^2$-methyloxalamide (7): Following literature precedent,[6] a solution of iodoalkene 5 (1.12 g, 4.98 mmol), ethyl 2-(methylamino)-2-oxoacetate (6) (0.62 g, 1.2 equiv) and triethylamine (0.83 mL, 1.2 equiv) in anhydrous ethanol (10 mL) was heated at 60° C. After 20 h, the brown solution was cooled to rt and concentrated in vacuo. Purification of the residue using a Teledyne Isco Combiflash® RF chromatographic system (25 g SiO$_2$ column eluted with 0-50% EtOAc/hexanes, 10 min; 50% EtOAc/hexanes, 10 min) gave 7 (0.93 g, 60%) as a white solid, 99.7-99.8° C. $^1$H NMR (500 MHz, CDCl$_3$) δ 7.46 (br s, 2H), 6.32-6.02 (m, 2H), 3.34 (app q, J=6.9 Hz, 2H), 2.91 (d, 1=5.3 Hz, 3H), 2.18 (dt, J=7.5, 7.0 Hz, 2H), 1.68-1.59 (m, 2H), 1.54-1.42 (m, 2H); $^{13}$C NMR (100 MHz, CDCl$_3$) δ 160.47, 159.70, 140.43, 83.07, 39.40, 34.11, 28.61, 26.15, 25.11.

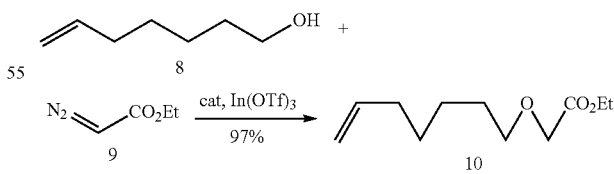

Synthesis of ethyl 2-(oct-7-en-1-yloxy)acetate (10): Following literature precedent,[7] neat 8 (1.92 g, 1.2 equiv) was added to a rt suspension of In(OTf)$_3$ (1.57 g, 20 mol %) in anhydrous toluene (20 mL). Ethyl diazoacetate (9) (1.60 g, 14 mmol) was added slowly under an argon atmosphere over 5 min (caution: exothermic) to give a yellow solution. After 2 days, the reaction mixture was concentrated in vacuo and the residue was purified using a Teledyne Isco Combiflash® RF chromatographic system (25 g SiO₂ column eluted with 0-10% EtOAc/hexanes, 5 min; 10% EtOAc/hexanes, 8 min) to give 10 (2.72 g, 97%) as a colorless oil. ¹H NMR (500 MHz, CDCl₃) δ 5.80 (ddt, J=16.9, 10.2, 6.6 Hz, 1H), 5.08-4.84 (m, 2H), 4.22 (q, J=7.1 Hz, 2H), 4.06 (s, 2H), 3.52 (t, J=6.7 Hz, 2H), 2.13-1.96 (m, 2H), 1.72-1.52 (m, 2H), 1.48-1.33 (m, 4H), 1.28 (t, J=7.1 Hz, 3H); ¹³C NMR (100 MHz, CDCl₃) δ 170.70, 138.99, 114.48, 71.97, 68.48, 60.86, 33.84, 29.55, 28.84, 25.63, 14.34.

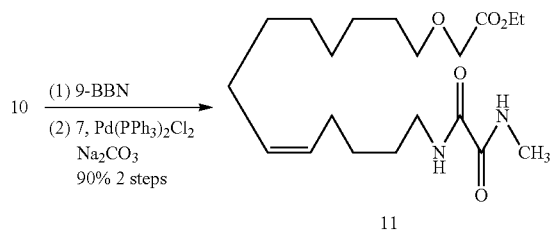 [SMILES: CCOC(=O)COCCCCCCC/C=C\CCCCNC(=O)C(=O)NC]

Synthesis of ethyl 2-((13-(2-(methylamino)-2-oxoacetamido)tridec-8(Z)-en-1-yl)oxy)acetate (11): To an oven-dried flask containing ethyl 2-(oct-7-en-1-yloxy)acetate (10) (220 mg, 1.2 equiv) was added a solution of 9-BBN (0.5 M in THF, 2.4 equiv, 4.40 mL). After stirring at rt for 3 h, an aqueous solution of Na₂CO₃ (1.5 mL of 2 M soln prepared from argon sparged H₂O) was added. After 5 min, Pd(PPh₃)₂Cl₂ (33 mg, 5 mol %) was added followed by 7 (284 mg, 0.92 mmol) dissolved in THF (4 mL). The resulting red solution was protected from light while another portion of aq. Na₂CO₃ (0.5 mL of 2 M soln) was added. The reaction was continued overnight (14 h) at rt, then at 50° C. for 4 h. After cooling to rt, the reaction mixture was concentrated in vacuo and the residue was purified using a Teledyne Isco Combiflash® RF chromatographic system (24 g SiO₂ column eluted with 0-40% EtOAc/hexanes, 6 min; 40% EtOAc/hexanes, 8 min; 40-100% EtOAc/hexanes, 4 min) to give ether 11 (330 mg, 90%) as an off-white solid. An analytical sample was purified by preparative TLC to give 11 as a white low melting solid.

TLC: 50% EtOAc/hexanes, R_f~ 0.49. ¹H NMR (500 MHz, CDCl₃) δ 7.45 (br s, 2H), 5.42-5.26 (m, 2H), 4.22 (q, J=7.2 Hz, 2H), 4.06 (s, 2H), 3.52 (t, J=6.7 Hz, 2H), 3.31 (dt, J=7.0, 6.5 Hz, 2H), 2.91 (d, J=5.1 Hz, 3H), 2.15-1.91 (m, 4H), 1.70-1.50 (m, 2H), 1.44-1.31 (m, 12H), 1.29 (t, J=7.1 Hz, 3H); ¹³C NMR (100 MHz, CDCl₃) δ 170.62, 160.55, 159.66, 130.58, 128.86, 71.96, 68.64, 39.55, 29.61, 29.51, 29.30, 29.19, 27.20, 26.83, 26.67, 26.15, 25.93, 14.21.

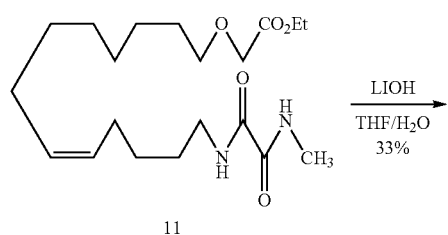

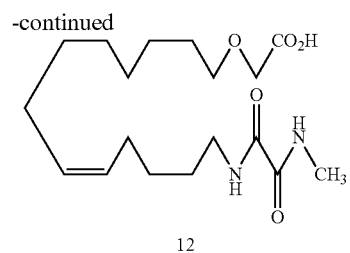

Synthesis of 2-((13-(2-(methylamino)-2-oxoacetamido)tridec-8(Z)-en-1-yl)oxy)acetic acid (12): To a rt solution of 11 (720 mg, 1.87 mmol) in THF (44 mL) was added LiOH (9 mL of 1.0 M aq. solution). After 48 h, the reaction was cooled to 4° C. and acidified to pH 4 using aq. 2 N HCl. The mixture was diluted with H₂O (10 mL) and extracted with EtOAc (15 mL×3). The combined organic extracts were dried over Na₂SO₄, filtered through a fritted funnel, and concentrated in vacuo. The crude material was purified using a Teledyne Isco Combiflash® RF chromatographic system (12 g SiO₂ column eluted with 0-80% EtOAc/hexanes, 15 min; 80% EtOAc/hexanes, 5 min) to give 12 (232 mg, 33%) as a white solid, mp 94.6-94.7° C.

¹H NMR (500 MHz, CDCl₃) δ 7.90 (s, 1H), 7.66 (s, 1H), 5.48-5.22 (m, 2H), 4.10 (s, 2H), 3.58 (t, J=6.5 Hz, 2H), 3.32 (dt, J=7.0, 6.5 Hz, 2H), 2.91 (d, J=5.2 Hz, 3H), 2.16-1.90 (m, 4H), 1.71-1.48 (m, 4H), 1.45-1.18 (m, 10H); ¹³C NMR (75 MHz, CD₃OD) δ 176.96, 160.32, 160.12, 130.65, 129.99, 72.51, 69.84, 39.45, 29.82, 29.58, 29.15, 27.71, 27.38, 27.24, 27.08, 26.83, 25.84, 25.03.

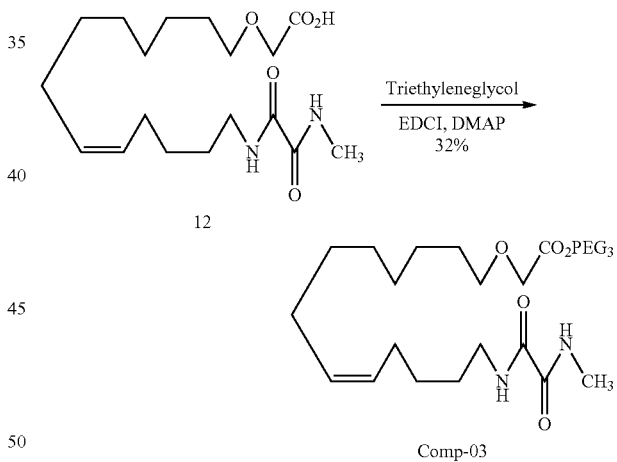

Synthesis of Comp-03: A mixture of EDCl (275 mg, 1.3 equiv) and triethyleneglycol (1.5 mL, 10 equiv) was dried under high vacuum for 90 min. The reaction flask was flushed with argon and DMAP (175 mg, 1.3 equiv), acetonitrile (50 mL), and acid 12 (395 mg, 1.1 mmol) dissolved in CH₂Cl₂ (20 mL) were added. After 3 days, the reaction mixture was concentrated in vacuo, the crude residue was dissolved in EtOAc (20 mL) and washed with 1N HCl (20 mL) and brine (20 mL). The aqueous washings were re-extracted with EtOAc (20 mL×2). The combined organic extracts were dried over Na₂SO₄, filtered, and concentrated in vacuo. The residue was purified using a Teledyne Isco Combiflash® RF chromatographic system (12 g SiO₂ column eluted with 0-80% EtOAc/hexanes, 8 min; 80% EtOAc/hexanes, 4 min; 80-100% EtOAc/hexanes, 3 min;

100% EtOAc, 15 min; 10% MeOH/CH₂Cl₂, 5 min) to give analog 13 (174 mg, 32%) as a white solid, mp 65.3-65.8° C.

¹H NMR (500 MHz, CDCl₃) δ 7.46 (s, 2H), 5.41-5.27 (m, 2H), 4.33 (t, J=4.7 Hz, 2H), 4.11 (s, 2H), 3.77-3.70 (m, 4H), 3.70-3.64 (m, 4H), 3.61 (app t, J=4.5 Hz, 2H), 3.52 (t, J=6.7 Hz, 2H), 3.42 (t, J=6.1 Hz, OH), 3.31 (dt, J=7.0, 6.5 Hz, 2H), 2.91 (d, J=5.2 Hz, 3H), 2.44 (s, 1H), 2.05 (dt, J=7.5, 7.0 Hz, 2H), 2.00 (dt, J=7.0, 6.5 Hz, 2H), 1.62-1.50 (m, 4H), 1.45-1.21 (m, 10H); ¹³C NMR (125 MHz, CDCl₃) δ 170.86, 160.83, 159.95, 130.76, 129.12, 72.76, 72.21, 70.77, 70.52, 69.19, 68.34, 63.84, 61.92, 39.78, 29.84, 29.73, 29.54, 29.42, 29.02, 27.44, 27.09, 26.92, 26.42, 26.15.

Compound 4 (Comp-04)

Synthesis of Compound 4 (Comp-04) was analogous to synthesis of compound 2 (Comp-02), while the urea-group was introduced following the synthetic route described in patent application WO2010/081683 (example 6).

Compound 5 (Comp-05)

Summary of Synthesis

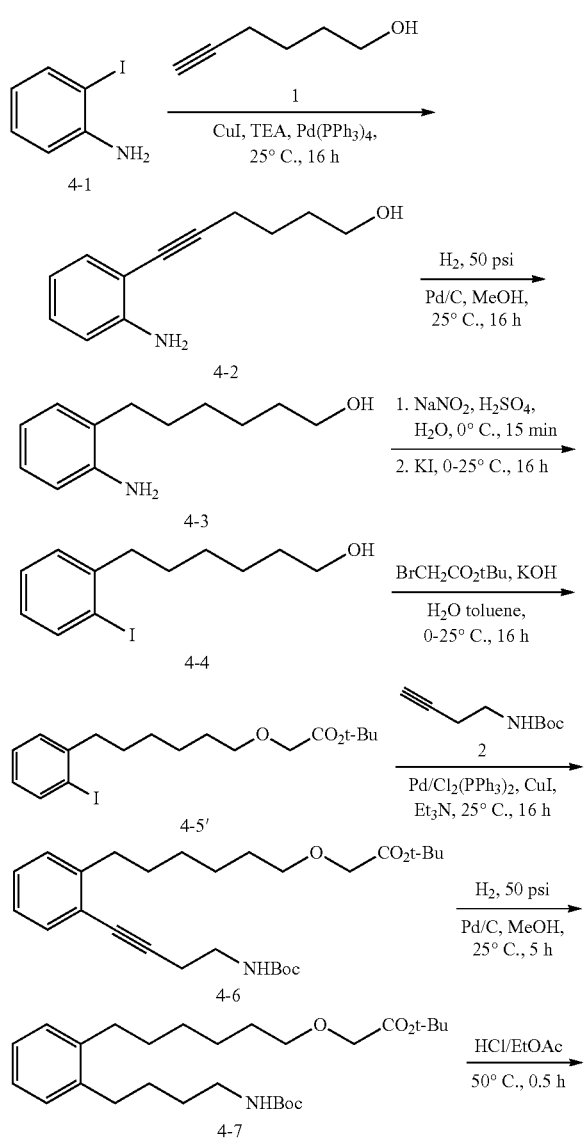

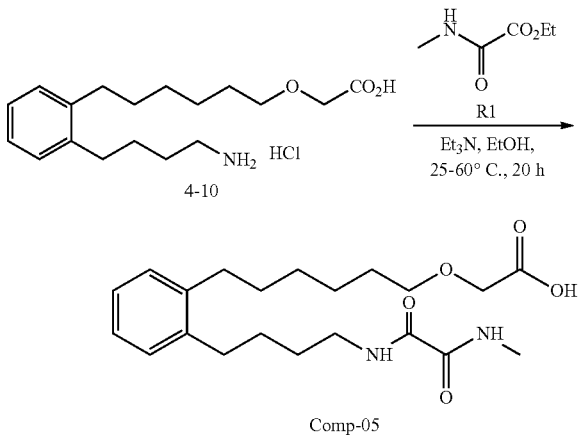

General Procedure for Preparation of Compound 4-2

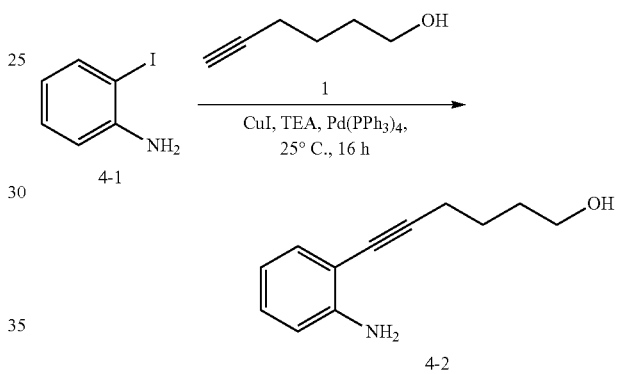

| Reagent | MW. | amount | Mol | Ratio | Other Info. |
|---|---|---|---|---|---|
| Cpd. 4-1 | 219.02 | 30.0 g | 137 mmol | 1.0 eq. | |
| Cpd. 1 | 98.14 | 13.4 g | 137 mmol | 1.0 eq. | |
| CuI | 190.45 | 522 mg | 2.74 mmol | 0.02 eq. | |
| Pd(PPh₃)₄ | 1155.56 | 1.58 g | 1.37 mmol | 0.01 eq. | |
| TEA | | 480 mL | | | |
| Product: (Cpd. 4-2) | 189.25 | 21.0 g | 99.9 mmol | | Yield: 73% |

A mixture of Cpd.4-1 (30.0 g, 137 mmol, 1.0 eq) in TEA (480 mL) was added Cpd.1 (13.4 g, 137 mmol, 1.0 eq), CuI (522 mg, 2.74 mmol, 0.02 eq), Pd(PPh₃)₄ (1.58 g, 1.37 mmol, 0.01 eq) under N₂ at 25° C. and stirred at 25° C. for 16 hrs. TLC (petroleum ether/ethyl acetate=1/1, R_f=0.5) showed that the reaction was complete. The solution was poured into aq·NH₄Cl (1.0 L), extracted with DCM (200 mL*5), the combined organic layers were washed with brine, dried over Na₂SO₄ and filtered. The filtrate was concentrated under reduced pressure. The crude product was purified by column chromatography on silica gel eluted with petroleum ether: EtOAc (10:1, 1:1) to give Cpd.4-2 (21.0 g, 73% yield) as yellow oil.

¹H NMR: ET5008-6-P1b1 400 MHz CDCl₃; 7.30-7.24 (m, 1H), 7.10 (t, J=7.6 Hz, 1H), 6.73-6.65 (m, 2H), 4.19 (br, 2H), 3.74 (m, 2H), 2.54 (t, J=6.0 Hz, 2H), 1.87-1.68 (m, 4H), 1.50-1.45 (m, 1H).

General Procedure for Preparation of Cpd.4-3

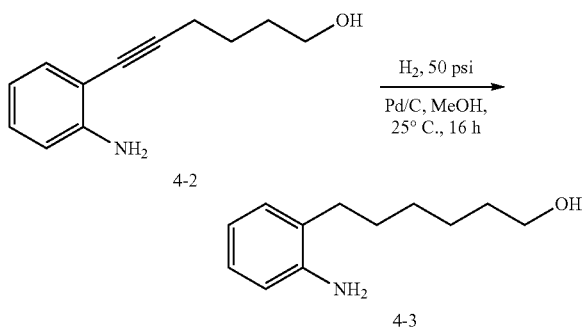

| Reagent | MW. | amount | Mol | Ratio | Other Info. |
|---|---|---|---|---|---|
| Cpd.4-2 | 189.25 | 21.0 g | 111 mmol | 1.0 eq. | |
| Pd/C | | 500 mg | | | |
| MeOH | | 500 mL | | | |
| Product: (Cpd.4-3) | 193.28 | 17.0 g | 83.6 mmol | | Yield: 75% |

A mixture of Cpd.4-2 (21.0 g, 111 mmol, 1.0 eq) in MeOH (500 mL) was added Pd/C (500 mg) and stirred at 25° C. under 50 psi of H$_2$ for 16 hrs. LC-MS (ET5008-10-P1A5, product: RT 1.10 min) show that the reaction was complete. Then the solution was filtered and concentrated to give Cpd.4-3 (17.0 g, 75% yield) as yellow oil.

$^1$H NMR: ET1668-10-P1b1 400 MHz CDCl$_3$; 7.08-7.03 (m, 2H), 6.78-6.69 (m, 2H), 3.69-3.62 (i, 4H), 2.52 (t, =8.0 Hz, 2H), 1.68-1.59 (m, 4H), 1.47-1.42 (m, 4H), 1.31-1.27 (n, 1H).

General Procedure for Preparation of Cpd.4-4

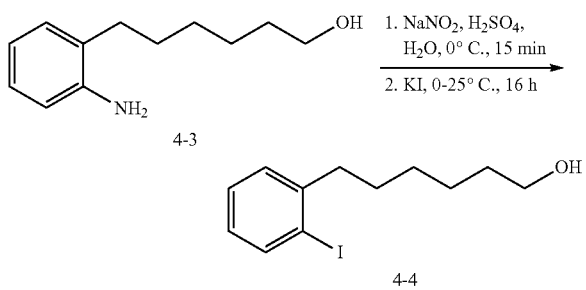

| Reagent | MW. | amount | Mol | Ratio | Other Info. |
|---|---|---|---|---|---|
| Cpd.4-3 | 193.28 | 17.0 g | 88.0 mmol | 1.0 eq. | |
| NaNO$_2$ | 69.00 | 6.07 g | 88.0 mmol | 1.0 eq. | |
| KI | 166.00 | 43.8 g | 264 mmol | 3.0 eq. | |
| Con•H$_2$SO$_4$ | 98.08 | 30.2 g | 308 mmol | 3.5 eq. | |
| H$_2$O | | 560 mL | | | |
| Product: (Cpd.4-4) | 304.17 | 17.0 g | 50.3 mmol | | Yield: 57% |

Con·H$_2$SO$_4$ (30.2 g, 308 mmol, 3.5 eq) was added to Cpd.4-3 (17.0 g, 88.0 mmol, 1.0 eq) in H$_2$O (500 mL) at 0° C. under N$_2$. A solution of NaNO$_2$ (6.07 g, 88.0 mmol, 1.0 eq) in H$_2$O (30.0 mL) was added to the solution at 0° C. and stirred at 0° C. for 15 mins. A solution of KI (43.8 g, 264 mmol, 3.0 eq) in H$_2$O (30.0 mL) was added at 0° C. and the resulting suspension was warmed to 25° C. and stirred for 45 mins. TLC (petroleum ether/ethyl acetate=1/1, R$_f$=0.9) showed that the reaction was complete. H$_2$O (400 mL) was added, extracted with EtOAc (350 mL*3), the combined organic layers were washed with brine, dried over Na$_2$SO$_4$ and filtered. The filtrate was concentrated under reduced pressure. The crude product was purified by column chromatography on silica gel eluted with petroleum ether: EtOAc (100:1, 10:1) to give Cpd.4-4 (17.0 g, 57% yield) as brown oil.

$^1$H NMR: ET5008-22-P1b1400 MHz CDCl$_3$; 7.80 (d, J=7.2 Hz, 1H), 7.28-7.23 (m, 1H), 7.21-7.18 (m, 1H), 6.89-6.85 (m, 1H), 3.65 (t, J=6.8 Hz, 2H), 2.71 (t, J=8.0 Hz, 2H), 1.61-1.50 (m, 4H), 1.45-1.40 (m, 4H), 1.31-1.28 (m, 1H).

General Procedure for Preparation of Compound 4-5'

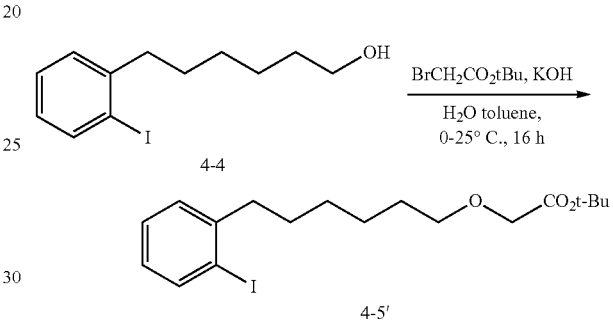

| Reagent | MW. | amount | Mol | Ratio | Other Info. |
|---|---|---|---|---|---|
| Cpd.4-4 | 304.17 | 10.0 g | 32.9 mmol | 1.0 eq. | |
| BrCH$_2$CO$_2$tBu | 195.05 | 7.70 g | 39.5 mmol | 1.2 eq. | |
| KOH | 56.11 | 33.0 g | 588 mmol | 18 eq. | |
| Bu$_4$NHSO$_4$ | 339.53 | 5.58 g | 16.4 mmol | 0.50 eq. | |
| Toluene | | 50.0 mL | | | |
| H$_2$O | | 50.0 mL | | | |
| Product: (Cpd.4-5') | 418.31 | 5.40 g | 12.3 mmol | | Yield: 37% |

A mixture of BrCH$_2$CO$_2$tBu (7.70 g, 39.5 mmol, 1.2 eq) and Cpd.4-4 (10.0 g, 32.9 mmol, 1.0 eq) in toluene (50.0 mL) was added Bu$_4$NHSO$_4$ (5.58 g, 16.4 mmol, 0.50 eq), KOH (33.0 g, 588 mmol, 17.9 eq) in H$_2$O (50.0 mL) at 0° C., then the mixture was stirred at 25° C. for 16 hrs. TLC (petroleum ether/ethyl acetate=10/1, R$_f$=0.62) show 40% SM remained. H$_2$O (200 mL) was added, extracted with DCM (200 mL*2), the combined organic layers were washed with brine, dried over Na$_2$SO$_4$ and filtered. The filtrate was concentrated under reduced pressure. The crude product was purified by column chromatography on silica gel eluted with petroleum ether: EtOAc (40:1) to give Cpd.4-5' (5.40 g, 37% yield) as yellow oil.

$^1$H NMR: ET5008-26-P1b1 400 MHz CDCl$_3$; 7.82 (d, J=7.2 Hz, 1H), 7.30-7.26 (m, 1H), 7.23-7.20 (m, 1H), 6.91-6.88 (m, 1H), 3.97 (s, 2H), 3.53 (t, J=6.8 Hz, 2H), 2.72 (t, J=8.0 Hz, 2H), 1.69-1.59 (m, 4H), 1.58-1.43 (m, 13H).

General Procedure for Preparation of Cpd.4-6

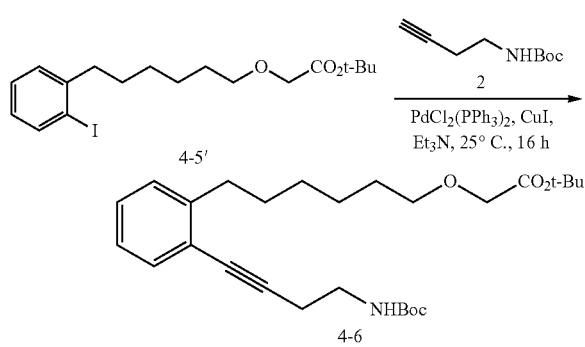

| Reagent | MW. | amount | Mol | Ratio | Other Info. |
|---|---|---|---|---|---|
| Cpd.4-5' | 418.31 | 5.40 g | 12.9 mmol | 1.0 eq. | |
| Cpd.2 | 169.22 | 2.18 g | 12.9 mmol | 1.0 eq. | |
| CuI | 190.45 | 49.2 mg | 258 umol | 0.02 eq. | |
| PdCl$_2$(PPh$_3$)$_2$ | 701.90 | 181 mg | 258 umol | 0.02 eq. | |
| Et3N | | 110 mL | | | |
| Product: (Cpd.4-6) | 459.62 | 3.00 g | 6.20 mmol | | Yield: 48% |

A mixture of Cpd.4-5' (5.40 g, 12.9 mmol, 1.0 eq) and Cpd.2 (2.18 g, 12.9 mmol, 1.0 eq) in Et$_3$N (110 mL) was added CuI (49.2 mg, 258 umol, 0.02 eq), PdCl$_2$(PPh$_3$)$_2$ (181 mg, 258 umol, 0.02 eq) at 25° C. under N$_2$ and stirred at 25° C. for 16 hrs. TLC (petroleum ether/ethyl acetate=1/1, R$_f$=0.3) show that the reaction was complete. Then aq·NH$_4$Cl (200 mL) was added, extracted with EtOAc (200 mL*3), the combined organic layers were washed with brine, dried over Na$_2$SO$_4$ and filtered. The filtrate was concentrated under reduced pressure. The crude product was purified by column chromatography on silica gel eluted with petroleum ether: EtOAc (10:1, 1:1) to give Cpd.4-6 (3.00 g, 48% yield) as yellow oil.

$^1$H NMR: ET5008-32-P1b1 400 MHz CDCl$_3$; □7.41-7.34 (m, 1H), 7.23-7.06 (m, 3H), 4.97-4.87 (m, 1H), 3.97 (s, 2H), 3.53 (t, J=6.8 Hz, 2H), 3.43-3.33 (m, 2H), 2.72 (t, J=8.0 Hz, 2H), 2.64 (J=8.0 Hz, 2H), 1.69-1.59 (m, 4H), 1.55-1.43 (m, 22H).

General Procedure for Preparation of Cpd.4-7

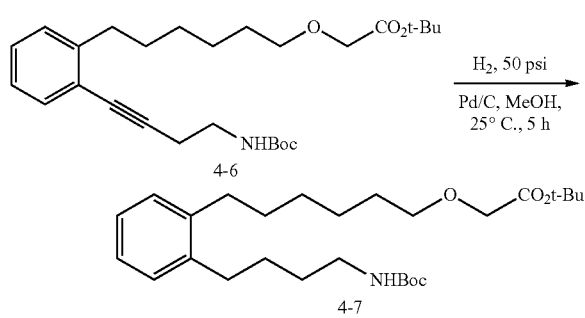

| Reagent | MW. | amount | Mol | Ratio | Other Info. |
|---|---|---|---|---|---|
| Cpd.4-6 | 459.62 | 3.00 g | 6.53 mmol | 1.0 eq. | |
| Pd/C | | 200 mg | | | |
| MeOH | | 20.0 mL | | | |
| Product: (Cpd.4-7) | 463.65 | 2.50 g | 4.91 mmol | | Yield: 75% |

A mixture of Cpd.4-6 (3.00 g, 6.53 mmol, 1.0 eq) in MeOH (20.0 mL) was added Pd/C (200 mg) and stirred at 25° C. under 50 psi of H$_2$ for 5 hrs. LC-MS (ET5008-33-P1A4, product: RT=1.04 min) show that the reaction was completed. Then the solution was filtered and concentrated to give Cpd.4-7 (2.50 g, 75% yield) as yellow oil.

$^1$H NMR: ET5008-33-P1b1 400 MHz CDCl$_3$; □7.13 (s, 4H), 4.54 (s, 1H), 3.96 (s, 2H), 3.52 (t, J=6.8 Hz, 2H), 3.18-3.14 (m, 2H), 2.65-2.57 (m, 4H), 1.75-1.54 (m, 10H), 1.53-1.37 (m, 20H).

General Procedure for Preparation of Cpd.4-10

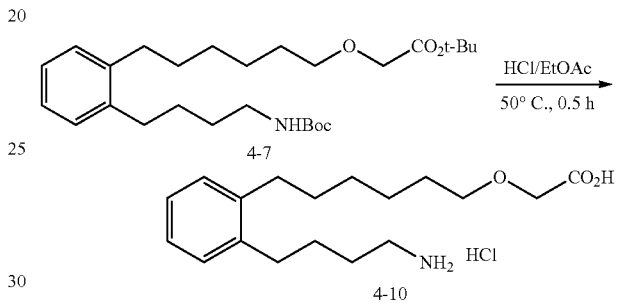

| Reagent | MW. | amount | Mol | Ratio | Other Info. |
|---|---|---|---|---|---|
| Cpd.4-7 | 463.65 | 1.00 g | 2.16 mmol | 1.0 eq. | |
| HCl/EtOAc | | 30.0 mL | | | 4N |
| Product: (Cpd.4-10) | 343.89 | 800 mg | 2.33 mmol | | crude |

A mixture of Cpd.4-7 (1.00 g, 2.16 mmol, 1.0 eq) in HCl/EtOAc (30.0 mL) at 50° C. and stirred at 50° C. for 0.5 h. LC-MS (ET5008-34-P1A4, product: RT=0.698 min) show that the reaction was completed. The mixture was concentrated to give crude Cpd.4-10 (800 mg) as yellow solid.

General Procedure for Preparation of Comp-05

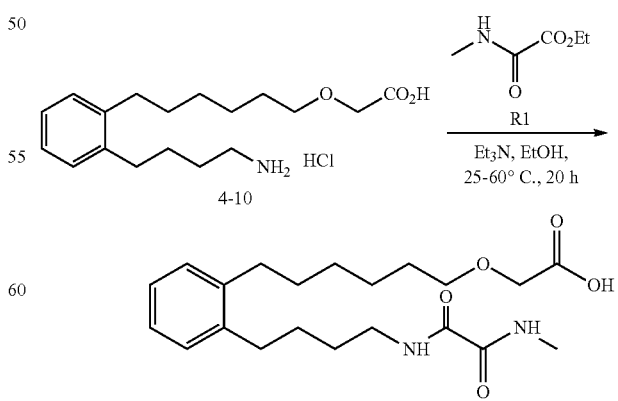

| Reagent | MW. | amount | Mol | Ratio | Other Info. |
|---|---|---|---|---|---|
| Cpd.4-10 | 343.89 | 800 mg | 2.33 mmol | 1.0 eq. | |
| Cpd.R1 | 131.13 | 611 mg | 4.66 mmol | 2.0 eq. | |
| Et$_3$N | 101.19 | 2.36 g | 23.3 mmol | 10 eq. | |
| EtOH | | 40.0 mL | | | |
| Product: Comp-05 | 392.49 | 370 mg | 933 umol | | Yield: 40% |

A mixture of Cpd.4-10 (800 mg, 2.33 mmol, 1.0 eq) in EtOH (40.0 mL) was added Et$_3$N (2.36 g, 23.3 mmol, 10.0 eq) and Cpd.R1 (611 mg, 4.66 mmol, 2.0 eq) at 25° C. Then the solution was stirred at 60° C. for 20 hrs. LC-MS (ET5008-35-P1A1, product: RT=0.81 min) show that the reaction was completed. The solution was concentrated. The residue was purified by prep-HPLC (TFA condition) to give Comp-05 (370 mg, 40% yield) as white solid.
HPLC Separation Method:

| Column | Luna C18 100 * 30 5u |
|---|---|
| Condition | 0.05% HCl-can |
| Begin B | 30 |
| End B | 60 |
| Gradient Time | 12 min |
| 100% B Hold Time | 4 min |
| Flow Rate | 25 mL/min |
| Injection | 12 |

$^1$H NMR: ET5008-35-P1b1 400 MHz CDCl$_3$; 10.46 (br, 1H), 8.35 (s, 1H), 7.74 (s, 1H), 7.12 (s, 4H), 4.12 (s, 2H), 3.59 (t, J=6.0 Hz, 2H 2H), 3.35 (q, J=7.2 Hz, 2H), 2.92 (d, J=5.2 Hz, 3H), 2.65-2.57 (m, 4H), 1.68-1.44 (m, 14H).
For the synthesis of Comp-14 to Comp-32 compounds, general building blocks have been synthesised beforehand:
Building Block 1 (BB-1)

N'-[(5Z)-6-iodohex-5-en-1-yl]-N-methylethanediamide

Step 1

PPh3 (140 g) and phthalimide (82.5 g) were suspended in dry THE (500.0 mL) and cooled to 0° C. A solution of 5-hexyn-1-ol (50.0 g) and diisopropyl azodicarboxylate (110 mL) in dry THE (100 mL) was then added dropwise over a period of 45 min. The resulting mixture was stirred at 0° C. for 1 h and then at r.t. over night.

THF was removed in vacuo as far as possible. The residue was suspended in PE/EtOAc=9:1 (700 mL) and stirred vigourously. The solvent was decanted off from the precipitated OPPh3. During this process, white needles (product) formed in the decanted solvent, which were filtered off and set aside (F1).

The OPPh3 precipitate was then further washed with PE/EtOAc=9:1 several times. All filtrates were then combined and evaporated in vacuo (F2). The needles from F1 were dissolved in EtOAc (200 mL) and washed with 1N NaOH (2×75 mL) and brine (50 mL), dried over Na2SO4 and concentrated in vacuo. The residue was filtered through a patch of SiO$_2$ (eluent CH$_2$Cl$_2$). The solvent was removed in vacuo and the oily residue was left standing in the fridge over weekend, after which white needles had been formed. The mixture was diluted with PE, the product was then filtered off, washed with PE and dried in vacuo to afford F1 as white needles. The mother liquor was combined with F2.

The yellow oil of F2 was dissolved in EtOAc (400 mL) and washed with 1 N NaOH (3×150 mL) and brine (50 mL). The organic layer was dried over Na$_2$SO$_4$ and concentrated in vacuo. The residue was purified by column chromatography on SiO$_2$ (eluent CH$_2$Cl$_2$). The product containing fractions were combined and evaporated. PE was added to the yellow oily residue, after which a precipitate formed. The mixture was cooled to 0° C., the solid was then filtered off and washed with PE to afford F2 as white solid. The mother liquor was evaporated. PE was added to the oily residue after which a precipitate formed. The mixture was left standing in the fridge for 2 h, the precipitate was then filtered off, washed with PE and dried in vacuo to afford F3 as pale yellow solid.

Step 2

2-(hex-5-yn-1-yl)-2,3-dihydro-1H-isoindole-1,3-dione (46.3 g), AgNO 3 (8.65 g) and NIS (68.8 g) were placed in a 1 L flask. Dry THE (500 mL) was added, the flask was flushed with argon and wrapped with aluminium foil to protect the reaction from light. The mixture was then stirred under an Ar-atmosphere at r.t. for 16 h. Control by LC/MS showed product.

The reaction mixture was decanted from the formed precipitate, diluted with water (400 mL) and extracted with EtOAc (3×200 mL). The combined organic layers were washed with water (100 mL), sat. Na$_2$SO$_3$ (3×100 mL) and brine (100 mL), dried over Na$_2$SO$_4$ and concentrated in vacuo. The residue was recrystallized from EtOH to afford F1 as white solid. The mother liquor was evaporated and again recrystallized from EtOH to afford F2 as yellow solid.

Step 3

2-Methyl-2-butene (29.4 mL) was added dropwise to a 0° C. cold solution of BH 3*SMe2 (2.00 M in THF, 64.4 mL) and stirred at 0° C. for 1 h and then at r.t. for 1 h. The mixture was then added dropwise to a 0° C. cold suspension of 2-(6-iodohex-5-yn-1-yl)-2,3-dihydro-1H-isoindole-1,3-dione (17.5 g) in THF (200 mL). After addition, the resulting mixture was stirred at r.t. for 1 h. Control by LC/MS showed complete consumption of starting material. The reaction mixture was cooled to 0° C., then HOAc (30.0 mL) was added dropwise, stirred for 30 min at 0° C. and then at r.t. over night. Control by LC/MS showed product.

THF was removed in vacuo as far as possible. The residue was then slowly poured into a solution of NaOH (15.0 g) in H2O (200 mL) and extracted with CH$_2$Cl$_2$ (3×100 mL). The combined organic layers were washed with brine, dried over Na$_2$SO$_4$ and concentrated in vacuo. The residue was used for further transformation as such.

Step 4

2-[(5Z)-6-iodohex-5-en-1-yl]-2,3-dihydro-1H-isoindole-1,3-dione (17.6 g, crude IK-0353/4) was dissolved in MeOH (150 mL). Hydrazine hydrate (6.00 mL) was added and the resulting mixture was stirred at r.t. for 16 h. Control by LC/MS showed product.

MeOH was removed in vacuo. The residue was suspended in CH$_2$Cl$_2$ (300 mL). The solid was filtered off and washed with CH$_2$Cl$_2$ (2×100 mL). The combined filtrates were then washed with water (2×100 mL), dried over Na$_2$SO$_4$ and concentrated in vacuo to afford the crude product as orange oil which was used for further transformation as such.

Step 5

Ethylchlorformylformiat (10.0 g) was dissolved in THF (50 mL) and cooled to 0° C. Pyridine (7.70 mL) was added dropwise and the mixture stirred at 0° C. for 30 min. Methylamine (2.0 M in THF, 47.6 mL) was then added dropwise. Stirring was continued at 0° C. for 3 h. Control by TLC (PE/EtOAc=1:3) showed product.

The precipitated salt was filtered off and the filtrate evaporated. The residue was taken up in EtOAc (200 mL), washed with 1N HCl (2×50 mL), dried over $Na_2SO_4$ and concentrated in vacuo to give the product in sufficient purity as brown oil.

Step 6

(5Z)-6-iodohex-5-en-1-amine (11.15 g) was dissolved in EtOH (200 mL). ethyl (methylcarbamoyl)formate (6.50 g) and $NEt_3$ (8.26 mL) were added and the resulting mixture was stirred at 50° C. for 24 h. Control by LC/MS showed incomplete conversion. Additional (methylcarbamoyl)formate (1.00 g) and $NEt_3$ (4.00 mL) were added and stirring was continued at 50° C. for 24 h. Control by LC/MS showed product.

EtOH was removed in vacuo. The residue was purified by column chromatography on $SiO_2$ ($CH_2Cl_2 \rightarrow CH_2Cl_2$/MeOH=50:1→CH2Cl2/MeOH=20:1). The product containing fractions were combined and evaporated. EtOAc (30 mL) was added to the partly solid residue, treated with sonication and left standing in the fridge over weekend. The precipitate was then filtered off, washed with little icecold EtOAc and dried in vacuo.

Yield: 10.3 g (67%) pale yellow solid.
Building Block 2 (BB-2)

N'-[4-(2-iodophenyl)butyl]-N-methylethanediamide

Step 1

PPh3 (95.5 g), phthalimide (56.1 g) and 3-Buten-1-ol (25.0 g) were suspended in dry THF (250 mL) and cooled to 0° C. Diisopropyl azodicarboxylate (75.1 mL) was then added dropwise over a period of 20 min. The resulting mixture was stirred at 0° C. for 30 min and then at r.t. over night. Control by LC/MS showed product.

THF was removed in vacuo as far as possible. The oily residue was diluted with PE/EtOAc=9:1 (400 mL) and stirred vigourously until a precipitate occurred. The precipitated OPPh3 was filtered off and washed extensively with PE/EtOAc=9:1. The combined filtrates were filtered through a patch of $SiO_2$ and then evaporated. The residue was diluted with PE (200 mL), mixed vigourously and placed in an icebath. The precipitated product was then filtered off and washed with PE to afford the product in sufficient purity as pale yellow solid.

Step 2

2-(but-3-en-1-yl)-2,3-dihydro-1H-isoindole-1,3-dione (22.1 g) was placed in a 1 L flask under and Ar-atmosphere. 9-BBN (0.5 M in THF, 273 mL) was then added dropwise at 0° C. and the resulting mixture was stirred at 0° C. for 30 min and then at r.t. over night. A solution of Na2CO3 (48.4 g) in water (250 mL) was then added and stirring was continued at r.t. for 30 min. Then 2-Iodo-phenylamine (20.0 g) and $PdCl_2(PPh_3)_2$ (2.80 g) was added and the mixture heated to 50° C. for 4 h. Control by LC/MS showed product.

The reaction mixture was diluted with EtOAc (200 mL) and the layers separated. The aqueous layer was extracted with EtOAc (300 mL) and the combined organic layers were washed with brine (200 mL) and dried over $Na_2SO_4$. The residue was purified by column chromatography on $SiO_2$ (PE/EtOAc=6:4).

Step 3

2-[4-(2-aminophenyl)butyl]-2,3-dihydro-1H-isoindole-1,3-dione (22.0) was dissolved in acetone (100 mL). Then water (200 mL) and conc. $H_2SO_4$ (13.9 mL) were added and the resulting suspension was cooled to 0° C. A solution of $NaNO_2$ (5.23 g) in water (50 mL) was added dropwise and the mixture stirred at 0° C. for 30 min. Then a solution of KI (37.2 g) in water (50 mL) was added dropwise, the reaction mixture warmed to r.t. and stirred for 20 h. Control by LC/MS showed product.

The reaction mixture was diluted with sat. $Na_2SO_3$ (200 mL) and extracted with EtOAc (3×200 mL). The combined organic layers were washed with brine (150 mL), dried over $Na_2SO_4$ and concentrated in vacuo. The residue was purified by column chromatography on $SiO_2$ (PE/EtOAc=8:2).

Step 4

2-[4-(2-iodophenyl)butyl]-2,3-dihydro-1H-isoindole-1,3-dione (21.2 g) was suspended in MeOH (300 mL). Hydrazine hydrate (5.10 mL) was added and the resulting mixture was stirred at r.t. for 3 d. Control by LC/MS showed product.

MeOH was removed in vacuo. The residue was suspended in $CH_2Cl_2$ (200 mL). The solid was filtered off and washed with $CH_2Cl_2$ (100 mL). The combined filtrates were then washed with water (2×100 mL). The combined aqueous layers were reextracted with $CH_2Cl_2$ (50 mL) and the combined organic layers were then dried over Na2SO4 and concentrated in vacuo to afford the product in sufficient purity as yellow oil.

Step 5

Ethylchlorformylformiat (10.0 g) was dissolved in THF (50 mL) and cooled to 0° C. Pyridine (7.70 mL) was added dropwise and the mixture stirred at 0° C. for 30 min. Methylamine (2.0 M in THF, 47.6 mL) was then added dropwise. Stirring was continued at 0° C. for 3 h. Control by TLC (PE/EtOAc=1:3) showed product.

The precipitated salt was filtered off and the filtrate evaporated. The residue was taken up in EtOAc (200 mL), washed with 1N HCl (2×50 mL), dried over $Na_2SO_4$ and concentrated in vacuo to give the product in sufficient purity as brown oil.

Step 6

4-(2-iodophenyl)butan-1-amine (11.0 g, crude IK-0355710) was dissolved in EtOH (100 mL). Ethyl (methylcarbamoyl) formate (5.76 g) and NEt3 (6.67 mL) were added and the resulting mixture was stirred at 50° C. for 18 h. Control by LC/MS showed product.

The reaction mixture was cooled to r.t. and EtOH was removed in vacuo. The residue was filtered through a patch of SiO2 ($CH_2Cl_2$/MeOH=98:2). Further purification by recrystallization from EtOAc.

Yield: 7.76 g (54%) beige solid.
Building Block 4 (BB-4)

2-{[(8Z)-13-[(methylcarbamoyl)formamido]tridec-8-en-1-yl]oxy}acetic acid

Step 1

NaH (60% in mineral oil, 771 mg) was suspended in dry THF (20.0 mL). The mixture was cooled to 0° C., then 6-Hepten-1-ol (1.18 mL) was added. Stirring was continued at 0° C. for 30 min, then a solution of bromoacetic acid (1.34 g) in THF (10.0 mL) was added dropwise. After complete addition, the ice bath was removed and stirred for 15 min, then the mixture was heated to 70° C. for 1.5 h. Control by TLC (PE/EtOAc=1:1) showed product.

The reaction mixture was poured into 1N NaOH (50 mL) and extracted with EtOAc (2×30 mL). The combined organic layers contained no product and were discarded. The aqueous layer was carefully acidified with conc. HCl and then again extracted with EtOAc (3×30 mL). The combined organic layers were dried over $Na_2SO_4$ and concentrated in vacuo to afford the product in sufficient purity as colorless oil.

Step 2

1,1'-Carbonyldiimidazole (15.6 g) was suspended in THF (200 mL). A solution of 2-(hept-6-en-1-yloxy)acetic acid (15.1 g) in THF (20 mL) was then added dropwise and the resulting mixture was stirred at r.t. for 6 h. THF was then removed in vacuo and MeOH (200 mL) was added to the residue. The mixture was stirred at r.t. for 3 d. Control by TLC (PE/EtOAc=9:1) showed product.

MeOH was removed in vacuo. PE (200 mL) was added to the residue and stirred vigourously for 5 min. The solvent was then decanted off from a thick, oily residue, which was further washed with PE (2×100 mL) and then discarded. The combined PE fractions were washed with 1N HCl (100 mL) and 1N NaOH (100 mL), dried over $Na_2SO_4$ and concentrated in vacuo to afford the product in sufficient purity as colorless liquid.

Step 3

Methyl 2-(hept-6-en-1-yloxy)acetate (2.88 g) was placed in 100 mL flask and cooled to 0° C. under and Ar atmosphere. 9-BBN (0.5 M in THF, 38.7 mL) was then added dropwise and the resulting mixture stirred at 0° C. for 30 min and then at r.t. for 2 h. A solution of $Na_2CO_3$ (6.84 g) in water (30.0 mL) was then added and stirring was continued at r.t. for 30 min. Then N'-[(5Z)-6-iodohex-5-en-1-yl]-N-methylethanediamide (BB-1, 4.00 g) and $PdCl_2(PPh_3)_2$ (453 mg) were added and the mixture heated to 50° C. for 1.5 h. Control by LC/MS showed product.

The reaction mixture was cooled to r.t. and the layers were separated. The aqueous layer was extracted with EtOAc (100 mL). The combined organic layers were washed with brine (50 mL), dried over Na2SO4 and concentrated in vacuo. The residue was purified by column chromatography on $SiO_2$ (PE/EtOAc 1:1).

Step 4

Methyl 2-{[(8Z)-13-[(methylcarbamoyl)formamido]tridec-8-en-1-yl]oxy}acetate (400 mg) was suspended in MeOH (20.0 mL). NaOH (3N, 5.00 mL) was added and the resulting mixture was stirred at r.t. for 15 min. Control by LC/MS showed product.

The reaction mixture was poured into 1N HCl (30 mL). The precipitated product was filtered off, washed with water and dried in vacuo.

Yield: 869 mg (86%) beige solid.

Building Block 6 (BB-6)

2-[3-(2-{4-[(Methylcarbamoyl)formamido]butyl}phenyl)propoxy]acetic acid

Step 1

NaH (60% in mineral oil, 15.2 g) was suspended in dry THF (250 mL). The mixture was cooled to 0° C., then allylalcohol (11.8 mL) was added. Stirring was continued at 0° C. for 30 min, then a solution of bromoacetic acid (26.3 g) in THF (50.0 mL) was added dropwise. After complete addition, the ice bath was removed and stirred for 15 min, the mixture was then heated to 70° C. for 3 h and stirred at r.t. over night.

The reaction mixture was poured into water (250 mL) and extracted with EtOAc (2×100 mL). The combined organic layers contained no product and were discarded. The aqueous layer was carefully acidified with conc. HCl and then again extracted with EtOAc (3×100 mL). The combined organic layers were dried over Na2SO4 and concentrated in vacuo to afford the product in sufficient purity as pale brown liquid.

Step 2

1,1'-Carbonyldiimidazole (30.7 g) was suspended in THF (200 mL). 2-(prop-2-en-1-yloxy)acetic acid (crude IK-0352/9) was then added dropwise and the resulting mixture was stirred at r.t. for 7 h. THF was then removed in vacuo and MeOH (200 mL) was added to the residue. The mixture was stirred at r.t. over night. Control by TLC (PE/EtOAc=8:2) showed product.

MeOH was removed in vacuo. PE (200 mL) was added to the residue and stirred vigourously for 5 min. The solvent was then decanted off from a thick, oily residue, which was further washed with PE (2×100 mL). Control by TLC showed most of the product remaining in the oily residue, which was thus washed with MTBE (4×100 mL). The PE and MTBE layers were combined and washed with 1N HCl (3×100 mL) and brine (50 mL), dried over $Na_2SO_4$ and concentrated in vacuo to afford the product in sufficient purity as pale yellow liquid.

Step 3

Methyl 2-(prop-2-en-1-yloxy)acetate (1.30 g) was placed in a 100 mL flask and cooled to 0° C. under and Ar atmosphere. 9-BBN (0.5 M in THF, 25.0 mL) was then added dropwise and the resulting mixture was stirred at 0° C. for 30 min and then at r.t. for 2 h. A solution of $Na_2CO_3$ (4.41 g) in water (25.0 mL) was then added and stirring was continued at r.t. for 30 min. Then N'-[4-(2-iodophenyl)butyl]-N-methylethanediamide (BB-2, 3.00 g) and $PdCl_2(PPh_3)_2$ (292 mg) were added and the mixture heated to 50° C. for 4 h and then stirred at r.t. overnight. Control by LC/MS showed incomplete conversion. Additional methyl 2-(prop-2-en-1-yloxy)acetate (650 mg) was placed in a separate flask under an Ar-atmosphere. 9-BBN (0.5 M in THF, 12.5 mL) was added at r.t. and the mixture stirred at r.t. for 2 h. A sat. solution of $Na_2CO_3$ (10 mL) was added and stirring was continued at r.t. for 30 min. The mixture was then added to the above reaction mixture. After adding fresh PdCl$_2$(PPh$_3$)$_2$ (200 mg), the mixture was stirred at 50° C. for 2 h. Control by LC/MS showed product.

The reaction mixture was cooled to r.t. and the layers were separated. The aqueous layer was extracted with EtOAc (100 mL). The combined organic layers were washed with brine (50 mL), dried over Na$_2$SO$_4$ and concentrated in vacuo. The residue was purified by column chromatography on SiO$_2$ (PE/EtOAc 3:7).

Step 4 methyl 2-[3-(2-{4-[(methylcarbamoyl)formamido]butyl}phenyl)propoxy]acetate (2.04 g) was dissolved in THF (30 mL). NaOH (3N, 30 mL) and MeOH (20 mL) were added and the resulting mixture was stirred at r.t. for 5 min. Control by LC/MS showed product.

The reaction mixture was acidified with 6N HCl and extracted with EtOAc (3×40 mL). The combined organic layers were washed with brine (30 mL), dried over Na$_2$SO$_4$ and concentrated in vacuo. The residue was purified by a short column on SiO2 (CH$_2$Cl$_2$/MeOH=9:1).

Yield: 1.56 g (80%) beige solid.

Building Block 8 (BB-8)

N'-[(5Z)-13-hydroxytridec-5-en-1-yl]-N-methyl-ethanediamide

Step 1

6-Hepten-1-ol (3.00 g) and imidazole (3.57 g) were dissolved in DMF (20.0 mL). TIPSCl (6.18 mL) was added and the resulting mixture was stirred at 60° C. for 6 h. Control by TLC (PE/EtOAc=8:2) showed almost complete conversion.

The reaction mixture was diluted with water (100 mL) and extracted with MTBE (3×40 mL). The combined organic layers were washed with 1N HCl (2×50 mL) and brine (20 mL), dried over Na$_2$SO$_4$ and concentrated in vacuo. The residue was purified by column chromatography on SiO$_2$ (PE/EtOAc=95:5).

Step 2

(Hept-6-en-1-yloxy)tris(propan-2-yl)silane (1.57 g) was placed in 100 mL flask and cooled to 0° C. under and Aratmosphere. 9-BBN (0.5 M in THF, 14.5 mL) was then added dropwise and the resulting mixture stirred at 0° C. for 30 min and then at r.t. for 2 h. A solution of Na$_2$CO$_3$ (2.56 g) in water (15.00 mL) was then added and stirring was continued at r.t. for 30 min. then N'-[(5Z)-6-iodohex-5-en-1-yl]-N-methylethanediamide (BB-1, 1.50 g) and PdCl$_2$(PPh$_3$)$_2$ (170 mg) were added and the mixture heated to 50° C. for 2 h. Control by LC/MS showed product.

The reaction mixture was cooled to r.t. and the layers were separated. The aqueous layer was extracted with EtOAc (2×50 mL). The combined organic layers were washed with brine (30 mL), dried over Na$_2$SO$_4$ and concentrated in vacuo. The residue was filtered through a patch of SiO$_2$ (PE/EtOAc=4:6). The so obtained crude product was used for further transformation as such.

Step 3

(hept-6-en-1-yloxy)tris(propan-2-yl)silane (2.20 g, crude IK-0357/16) was dissolved in THF (50 mL) and cooled to 0° C. TBAF*3H2O (2.29 g) was added and the resulting mixture was stirred at 0° C. for 30 min and then at r.t. for 6 h. Control by TLC (PE/EtOAc=1:1) and LC/MS showed complete conversion.

The reaction mixture was poured into water (100 mL) and extracted with EtOAc (3×40 mL). The combined organic layers were washed with brine (20 mL), dried over Na2SO4 and concentrated in vacuo. The residue was passed through a short column on SiO2 (PE/EtOAc=1:1→EtOAc).

Yield: 1.11 g (77%) beige solid.

Building Block 9 (BB-9)

N'-{4-[2-(3-hydroxypropyl)phenyl]butyl}-Nmethyl-ethanediamide

Step 1

2-Propen-1-ol (3.00 g) and imidazole (7.03 g) were dissolved in DMF (20.0 mL). TIPSCl (14.4 mL) was added and the resulting mixture was stirred at 60° C. for 6 h. Control by TLC (PE/EtOAc=8:2) showed almost complete conversion. The reaction mixture was diluted with water (100 mL) and extracted with MTBE (3×40 mL). The combined organic layers were washed with 1N HCl (2×50 mL) and brine (20 mL), dried over Na$_2$SO$_4$ and concentrated in vacuo. The residue was purified by column chromatography on SiO$_2$ (PE/EtOAc=95:5).

Step 2

(prop-2-en-1-yloxy)tris(propan-2-yl)silane (1.33 g) was placed in a 100 mL flask and cooled to 0° C. under and Ar-atmosphere. 9-BBN (0.5 M in THF, 14.2 mL) was then added dropwise and the resulting mixture was stirred at 0° C. for 30 min and then at r.t. for 2 h.

A solution of Na2CO3 (2.21 g) in water (15.0 mL) was then added and stirring was continued at r.t. for 30 min. Then N'-[4-(2-iodophenyl)butyl]-N-methylethanediamide (1.50 g) and PdCl$_2$(PPh$_3$)$_2$ (146 mg) were added and the mixture heated to 50° C. for 3 h. Control by LC/MS showed product. The reaction mixture was cooled to r.t. and the layers were separated. The aqueous layer was extracted with EtOAc (100 mL). The combined organic layers were washed with brine (50 mL), dried over Na$_2$SO$_4$ and concentrated in vacuo. The residue was passed through a short column of SiO$_2$ (PE/EtOAc 1:1). The still crude product was then used for further transformation as such.

Step 3

N-methyl-N'-{4-[2-(3-{[tris(propan-2-yl)silyl]oxy}propyl)phenyl]butyl}ethanediamide (1.87 g, crude IK-0357/17) was dissolved in THF (50 mL) and cooled to 0° C. TBAF*3H$_2$O (1.97 g) was added and the resulting mixture was stirred at 0° C. for 30 min and then at r.t. for 16 h. Control by LC/MS showed complete conversion. The reaction mixture was poured into water (100 mL) and extracted with EtOAc (3×40 mL). The combined organic layers were washed with brine (20 mL), dried over Na$_2$SO$_4$ and concentrated in vacuo. The residue was passed through a short column on SiO$_2$(PE/EtOAc=1:1→EtOAc).

Yield: 911 mg (75%) beige solid.

Building Block 11 (BB-11)

N'-[(5Z)-13-(2-aminoethoxy)tridec-5-en-1-yl]-Nm-ethylethanediamide

Step 1

NaH (60% in mineral oil, 7.71 g) was suspended in dry THE (200 mL). The mixture was cooled to 0° C., then 6-Hepten-1-ol (11.8 mL) was added. Stirring was continued at 0° C. for 30 min, then a solution of bromoacetic acid (13.4 g) in THF (100 mL) was added dropwise. After complete addition, the ice bath was removed and stirred for 15 min, then the mixture was heated to 70° C. for 3 h. Control by TLC (PE/EtOAc=1:1) showed product.

The reaction mixture was poured into 1N NaOH (300 mL) and extracted with EtOAc (2×100 mL). The combined organic layers contained no product and were discarded. The aqueous layer was carefully acidified with conc. HCl and then again extracted with EtOAc (3×100 mL). The combined organic layers were dried over $Na_2SO_4$ and concentrated in vacuo to afford the product in sufficient purity as pale brown oil.

Step 2

1,1'-Carbonyldiimidazole (15.6 g) was suspended in THE (200 mL). A solution of 2-(hept-6-en-1-yloxy)acetic acid (15.1 g) in THE (20 mL) was then added dropwise and the resulting mixture was stirred at r.t. for 6 h. THE was then removed in vacuo and MeOH (200 mL) was added to the residue. The mixture was stirred at r.t. for 3 d. Control by TLC (PE/EtOAc=9:1) showed product.

MeOH was removed in vacuo. PE (200 mL) was added to the residue and stirred vigourously for 5 min. The solvent was then decanted off from a thick, oily residue, which was further washed with PE (2×100 mL) and then discarded. The combined PE fractions were washed with 1N HCl (100 mL) and 1N NaOH (100 mL), dried over $Na_2SO_4$ and concentrated in vacuo to afford the product in sufficient purity as colorless liquid.

Step 3 methyl 2-(hept-6-en-1-yloxy)acetate (5.00 g) was dissolved in $CH_2Cl_2$ (100 mL) and cooled to 0° C. DIBALH (1.00 M in $CH_2Cl_2$, 61.7 mL) was added dropwise, and the resulting mixture was stirred at 0° C. for 30 min and then at r.t. over night. Control by TLC (PE/EtOAc=8:2) showed complete conversion.

The reaction mixture was cooled to 0° C. and carefully quenched with sat. aqueous $Na_2SO_4$. The mixture was then diluted with $CH_2Cl_2$ (100 mL), stirred vigourously for 20 min and then filtered through celite. The filtercake was washed with $CH_2Cl_2$ several times. The combined filtrates were concentrated in vacuo to afford the product in sufficient purity as colorless liquid.

Step 4

$PPh_3$ (7.17 g), phthalimide (4.21 g) and 2-(hept-6-en-1-yloxy)ethan-1-ol (4.12 g) were suspended in dry THE (100 mL) and cooled to 0° C. Diisopropyl azodicarboxylate (5.79 mL) was then added dropwise over a period of 20 min. The resulting mixture was stirred at 0° C. for 30 min and then at r.t. over night.

THE was removed in vacuo as far as possible. The oily residue was diluted with PE/EtOAc=9:1 (200 mL) and stirred vigourously until a precipitate occurred. The precipitated OPPh3 was filtered off and washed extensively with PE/EtOAc=9:1. The combined filtrates were filtered through a patch of $SiO_2$ (eluent PE/EtOAc=9:1) and evaporated. The residue was purified by column chromatography on $SiO_2$ (PE/EtOAc=8:2).

Step 5

2-[2-(hept-6-en-1-yloxy)ethyl]-2,3-dihydro-1H-isoindole-1,3-dione (2.22 g) was placed in 100 mL flask and cooled to 0° C. under and Ar-atmosphere. 9-BBN (0.5 M in THF, 19.3 mL) was then added dropwise and the resulting mixture stirred at 0° C. for 30 min and then at r.t. for 2 h. A solution of Na2CO3 (3.42 g) in water (20.0 mL) was then added and stirring was continued at r.t. for 30 min. then N'-[(5Z)-6-iodohex-5-en-1-yl]-N-methylethanediamide (BB-1, 2.00 g) and $PdCl_2(PPh_3)_2$ (226 mg) were added and the mixture heated to 50° C. for 1.5 h. Control by LC/MS showed product.

The reaction mixture was cooled to r.t. and the layers were separated. The aqueous layer was extracted with EtOAc (2×30 mL). The combined organic layers were washed with brine (30 mL), dried over $Na_2SO_4$ and concentrated in vacuo. The residue was purified by column chromatography on SiO2 (PE/EtOAc=4:6).

Step 6

N'-[(5Z)-13-[2-(1,3-dioxo-2,3-dihydro-1H-isoindol-2-yl) ethoxy]tridec-5-en-1-yl]-N-methylethanediamide (2.36 g) was suspended in MeOH (100 mL). Hydrazine hydrate (486 µL) was added and the resulting mixture was stirred at r.t. for 16 h. Control by LC/MS showed product.

MeOH was removed in vacuo. The residue was suspended in $CH_2Cl_2$/7N $NH_3$ in MeOH=9:1 (100 mL) and filtered through as patch of $SiO_2$ and further eluted with $CH_2Cl_2$/7N $NH_3$ in MeOH=9:1 (300 mL). The filtrate was concentrated in vacuo to afford 1.68 g of the crude product. 60 mg were subjected to purification by preparative TLC ($CH_2Cl_2$/7N $NH_3$ in MeOH=9:1). The rest of the crude material was used for further transformations as such.

Yield: 41 mg (2%) pale yellow solid (purified).
Compound 14 (Comp-14)

N-methyl-N'-[(5Z)-13-[(1H-1,2,3,4-tetrazol-5-yl) methoxy]tridec-5-en-1-yl] ethanediamide Step 1

NaH (60% in mineral oil, 7.71 g) was suspended in dry THE (200 mL). The mixture was cooled to 0° C., then 6-Hepten-1-ol (11.8 mL) was added. Stirring was continued at 0° C. for 30 min, then a solution of bromoacetic acid (13.4 g) in THE (100 mL) was added dropwise. After complete addition, the ice bath was removed and stirred for 15 min, then the mixture was heated to 70° C. for 3 h. Control by TLC (PE/EtOAc=1:1) showed product. The reaction mixture was poured into 1N NaOH (300 mL) and extracted with EtOAc (2×100 mL). The combined organic layers contained no product and were discarded. The aqueous layer was carefully acidified with conc. HCl and then again extracted with EtOAc (3×100 mL). The combined organic layers were dried over $Na_2SO_4$ and concentrated in vacuo to afford the product in sufficient purity as pale brown oil.

Yield: 14.1 g (93%) pale brown oil Step 2

A mixture of 2-(hept-6-en-1-yloxy)acetic acid (3.00 g) and $SOCl_2$ (15.00 mL) was heated to 70° C. for 1 h. Excess SOCl2 was then removed in vacuo and the residue was taken up in dichloroethane (15.0 ml). Then ammonia was slowly bubbled through the solution for 5 min. The reaction mixture diluted with water (50 mL) and extracted with CH2Cl2 (3×30 mL). The combined organic layers were washed with sat. NaHCO3 (30 mL) and brine (10 mL), dried over Na2SO4 and concentrated in vacuo to afford the product in sufficient purity as white solid. m=2.16 g (y=62%). Analog in TLC to IK-0367/1

Step 3

2-(hept-6-en-1-yloxy)acetamide (2.61 g) was dissolved in CH2Cl2 (50 mL). NEt3 (6.35 mL) was added and the mixture was cooled to 0° C. A solution of POCl3 (1.54 mL) in CH2Cl2 (4 mL) was slowly added. Stirring was then continued at 0° C. for 15 min. Control by TLC (PE/EtOAc=8:2) showed product.

sat. NaHCO$_3$ (5.00 mL) was added at 0° C. and stirred for 30 min at that temperature. The mixture was allowed to come to r.t., diluted with water (15.0 mL) and extracted with CH2Cl2 (3×20 mL). The combined organic layers were washed with sat. NaHCO$_3$ (10.0 mL) and brine (10.0 mL), dried over Na2SO4 and then filtered through a pad of SiO$_2$ (eluent CH2Cl2). The product was obtained after evaporation in sufficient purity as colorless oil. m=2.08 g, y=89%.

Step 4

2-(hept-6-en-1-yloxy)acetonitrile was placed in a 10 mL flask and cooled to 0° C. under and Ar-atmosphere. 9-BBN (0.5 M in THF, 1.63 mL) was then added dropwise and the resulting mixture was stirred at 0° C. for 30 min and then at r.t. for 2 h. A solution of Na$_2$CO$_3$ (288 mg) in degazed water (1 mL) was then added and stirring was continued at r.t. for 30 min. Then N'-[(5Z)-6-iodohex-5-en-1-yl]-N-methyl-ethanediamide (168 mg) and PdCl$_2$(PPh$_3$)$_2$ (19 mg) were added and the mixture heated to 50° C. overnight. Water was added and mixture was extracted with DCM. Organic layer was dried over MgSO4, filtered and solvent evaporated. Mixture was purified by preparative TLC (DCM/MeOH 95/5). m=70 mg, y=38%.

Step 5

N'-[(5Z)-13-(cyanomethoxy)tridec-5-en-1-yl]-N-methyl-ethanediamide, natrium azide and triethylamine hydrochloride were dissolved in THF and the reaction mixture stirred at 70° C. overnight.

Water and ethyl acetate were added. The mixture was acidified with HCl3N. The aqueous layer (acid pH) is then extracted with ethyl acetate (×3), and the combined organic layer washed with brine. The organic layer was dried over MgSO$_4$, filtered and solvent removed under vacuo. m=82 mg. Product was purified by preparative TLC (DCM/MeOH 95/5)

Yield: 8 mg (10%), as white powder.

Compound 15 (Comp-15)

N'-(4-{2-[3-(carbamoylmethoxy)propyl]phenyl}butyl)-N-methylethanediamide 250 mg (0.72 ol) 2-[3-(2-{4-[(Methylcarbamoyl)formamido]butyl}phenyl)propoxy]acetic acid (BB-6) and 164.1 mg (0.86 mmol) EDCl were dissolved in 20 ml DCM. 36.5 mg (2.14 mmol, 5.35 ml) ammonia (0.4 M in THF) were added and the mixture was stirred at rt over the weekend.

The mixture was poured into 50 ml water and extracted with DCM (3×50 ml). The combined organic layers were dried over Na$_2$SO$_4$ and concentrated.

Yield: 50 mg (20%), white solid.

Compound 16 (Comp-16)

N-Methyl-N'-[(5Z)-13-[(5-oxo-4,5-dihydro-1H-1,2,4-triazol-3-yl)methoxy]tridec-5-en-1-yl]ethanediamide

Step 1

NaH (60% in mineral oil, 7.71 g) was suspended in dry THF (200 mL). The mixture was cooled to 0° C., then 6-Hepten-1-ol (11.8 mL) was added. Stirring was continued at 0° C. for 30 min, then a solution of bromoacetic acid (13.4 g) in THF (100 mL) was added dropwise. After complete addition, the ice bath was removed and stirred for 15 min, then the mixture was heated to 70° C. for 3 h. Control by TLC (PE/EtOAc=1:1) showed product. The reaction mixture was poured into 1N NaOH (300 mL) and extracted with EtOAc (2×100 mL). The combined organic layers contained no product and were discarded. The aqueous layer was carefully acidified with conc. HCl and then again extracted with EtOAc (3×100 mL). The combined organic layers were dried over Na2SO4 and concentrated in vacuo to afford the product in sufficient purity as pale brown oil.

Step 2

1,1'-Carbonyldiimidazole (15.6 g) was suspended in THF (200 mL). A solution of 2-(hept-6-en-1-yloxy)acetic acid (15.1 g) in THF (20 mL) was then added dropwise and the resulting mixture was stirred at r.t. for 6 h. THF was then removed in vacuo and MeOH (200 mL) was added to the residue. The mixture was stirred at r.t. for 3 d. Control by TLC (PE/EtOAc=9:1) showed product. MeOH was removed in vacuo. PE (200 mL) was added to the residue and stirred vigorously for 5 min. The solvent was then decanted off from a thick, oily residue, which was further washed with PE (2×100 mL) and then discarded. The combined PE fractions were washed with 1N HCl (100 mL) and 1N NaOH (100 mL), dried over Na$_2$SO$_4$ and concentrated in vacuo to afford the product in sufficient purity as colorless liquid.

Step 3

500 mg (2.68 mmol) and 1.34 g (26.9 mmol, 1.30 ml) hydrazine hydrate were dissolved in 5 ml EtOH and stirred at 70° C. for 4.5 h (→clear solution).
→LC/MS: GH-0513/1-1
→TLC (EA/PE 1:1): Complete consumption of starting material
The mixture was evaporated to dryness

Step 4

500 mg (2.68 mmol) 2-(Hept-6-en-1-yloxy)acetohydrazide (GH-0513/1) were dissolved in 3 ml AcOH. 653.3 mg (8.05 mmol) potassium cyanate dissolved in 3 ml water were added and the mixture was stirred at rt for 1.5 h (h yellow solution). The mixture was evaporated to dryness.

Step 5

The oily residue was dissolved in 10 ml 2M NaOH and heated to reflux for 2 h.→LC/MS: GH-0515/1-2: Complete consumption of intermediate 1. The mixture was acidified using conc. HCl and extracted with EA (3×20 ml). The combined organic layers were dried over Na$_2$SO$_4$ and concentrated to dryness. The crude solid was recrystallized from ACN.

Step 6

Under Argon atmosphere 92.0 mg (0.44 mmol) 3-[(Hept-6-en-1-yloxy)methyl]-4,5-dihydro-1H-1,2,4-triazol-5-one (GH-0515/1) dissolved in 2 ml anhydrous THF were added to a solution of 88.5 mg (0.73 mmol, 1.45 ml) 9BBN (0.5M in THF) and the mixture was stirred at rt over night. A solution of 153.8 mg (1.45 mmol) Na$_2$CO$_3$ in 1 ml water were added and stirring at rt was continued for 15 min. Then 90.0 mg (0.29 mmol) N'-[(5Z)-6-iodohex-5-en-1-yl]-methylethanediamide (IK-0356/2) dissolved in 2 ml THF and 10.2 mg (14.5 µmol) PdCl2(PPh3)$_2$ were added and the mixture was heated to 50° C. for 4 h (a yellow biphasic mixture).

→LC/MS: GH-0516/1-1: Product was detected

The organic layer was separated via pipette and evaporated to dryness. The crude product was purified via flash column chromatography on silica gel (DCM/MeOH 20:1 à 9:1, Rf of possible product: 0.62). Recrystallization from CAN.

Yield: 51 mg (0.13 mmol, 45%).
Compound 17 (Comp-17)

N-methyl-N'-[(5Z)-13-[(phenylcarbamoyl)methoxy]tridec-5-en-1-yl]ethanediamide

2-{[(8Z)-13-[(methylcarbamoyl)formamido]tridec-8-en-1-yl]oxy}acetic acid (BB-4, 50.0 mg, 140.3 µmol), Aniline (26 µl, 280.5 µmol), HBTU (53.4 mg, 140.3 µmol) and DMAP (1.7 mg, 14.0 µmol) were placed in a G16 vial. DMF (2.00 ml) and NEt 3 (78.0 µl, 561.1 µmol) were added and the resulting mixture was stirred at r.t. for 16 h. Control by LC/MS showed product.

The reaction mixture was diluted with water (20 ml) and was extracted with Et2O (3×20 ml). The combined organic layers were washed with sat. NaHCO$_3$ (20 ml) and brine (10 ml), dried over Na$_2$SO$_4$ and concentrated in vacuo. The product was lyophilized.

Yield: 52 mg (87%), white solid.
Compound 18 (Comp-18)

N-methyl-N'-[(5Z)-13-{[(oxan-4-yl)carbamoyl]methoxy}tridec-5-en-1-yl] ethanediamide 2-{[(8Z)-13-[(methylcarbamoyl)formamido]tridec-8-en-1-yl]oxy}acetic acid (BB-4, 50.0 mg, 140.3 µmol), 4-Aminotetrahydropyran (29 µl, 280.5 µmol), HBTU (53.4 mg, 140.3 µmol) and DMAP (1.7 mg, 14.0 µmol) were placed in a G16 vial. DMF (2.00 ml) and NEt3 (78.0 µl, 561.1 µmol) were added and the resulting mixture was stirred at r.t. for 16 h. Control by LC/MS showed product. The reaction mixture was diluted with water (20 ml) and was extracted with Et2O (3×20 ml). The combined organic layers were washed with sat. NaHCO$_3$ (20 ml) and brine (10 ml), dried over Na2SO4 and concentrated in vacuo. The product was lyophilized.

Yield: m=58 mg (94%) white solid.
Compound 19 (Comp-19)

N-methyl-N'-[(5Z)-13-{[(1,3-oxazol-2-yl)carbamoyl]methoxy}tridec-5-en-1-yl]ethanediamide 2-{[(8Z)-13-[(methylcarbamoyl)formamido]tridec-8-en-1-yl]oxy}acetic acid (BB-4, 50.0 mg, 140.3 µmol), 1,3-Oxazol-2-amine (24 mg, 280.5 µmol), HBTU (53.4 mg, 140.3 µmol) and DMAP (1.7 mg, 14.0 µmol) were placed in a G16 vial. DMF (2.00 ml) and NEt$_3$ (78.0 µl, 561.1 µmol) were added and the resulting mixture was stirred at r.t. for 16 h. Control by LC/MS showed product.

The reaction mixture was diluted with water (20 ml) and was extracted with Et$_2$O (3×20 ml). The combined organic layers were washed with sat. NaHCO$_3$ (20 ml) and brine (10 ml), dried over Na$_2$SO$_4$ and concentrated in vacuo. The residue was purified by preparative TLC (DCM/MeOH=95:5).

Yield: 11 mg (19%), white solid.
Compound 20 (Comp-20)

N'-[(5Z)-13-{[(4-methoxyphenyl)carbamoyl]methoxy}tridec-5-en-1-yl]-Nmethylethanediamide 2-{[(8Z)-13-[(methylcarbamoyl)formamido]tridec-8-en-1-yl]oxy}acetic acid (BB-4, 50.0 mg, 140.3 µmol), p-Anisidine (35 mg, 280.5 µmol), HBTU (53.4 mg, 140.3 µmol) and DMAP (1.7 mg, 14.0 µmol) were placed in a G16 vial. DMF (2.00 ml) and NEt$_3$ (78.0 µl, 561.1 µmol) were added and the resulting mixture was stirred at r.t. for 16 h. Control by LC/MS showed product.

The reaction mixture was diluted with water (20 ml) and was extracted with Et$_2$O (3×20 ml). The combined organic layers were washed with sat. NaHCO$_3$ (20 ml) and brine (10 ml), dried over Na$_2$SO$_4$ and concentrated in vacuo. The residue was purified by preparative TLC (DCM/MeOH=98:2).

Yield: 18 mg (28%), beige solid.
Compound 21 (Comp-21)

N-Methyl-N'-[4-(2-{3-[(phenylcarbamoyl)methoxy]propyl}phenyl)butyl] ethanediamide 40 mg (0.11 mmol) 2-[3-(2-{4-[(Methylcarbamoyl)formamido]butyl}phenyl)propoxy]acetic acid (BB-6), 26.3 mg (0.14 mmol) EDCl and 11.7 mg (0.13 mmol, 11.5 µl) aniline were dissolved in 3 ml DCM and stirred at rt of the weekend (clear solution).

The mixture was evaporated to dryness and purified via pTLC (1 mm, DCM/MeOH 20:1, R$_f$ of possible product: 0.54).

Yield: 24 mg (51%), white solid.
Compound 22 (Comp-22)

N-Methyl-N'-[4-(2-{3-[2-oxo-2-(pyrrolidin-1-yl)ethoxy]propyl}phenyl)butyl] ethanediamide 50 mg (0.14 mmol) 2-[3-(2-{4-[(Methylcarbamoyl)formamido]butyl}phenyl)propoxy]acetic acid (BB-6), 32.8 mg (0.17 mmol) EDCl and 20.3 mg (0.29 mmol, 23.4 µl) Pyrrolidine were dissolved in 3 ml DCM and stirred at rt for 1.5 h (clear solution).

The mixture was evaporated to dryness and purified via pTLC (1 mm, DCM/MeOH 10:1, R$_f$ of possible product: 0.46).

Yield: 20 mg (35%), white solid.
Compound 23 (Comp-23)

N-Methyl-N'-[4-(2-{3-[2-(morpholin-4-yl)-2-oxoethoxy]propyl}phenyl)butyl] ethanediamide 50 mg (0.14 mmol) 2-[3-(2-{4-[(Methylcarbamoyl)formamido]butyl}phenyl)propoxy]acetic acid (BB-6, IK-0358/6), 32.8 mg (0.17 mmol) EDCl and 24.9 mg (0.29 mmol, 24.9 µl) morpholine were dissolved in 3 ml DCM and stirred at rt over the weekend (clear solution).

The mixture was evaporated to dryness and purified via pTLC (1 mm, DCM/MeOH 10:1, $R_f$ of possible product: 0.48).

Yield: 34 mg (58%), white solid.
Compound 24 (Comp-24)

4-{2-[3-(2-{4-[(methylcarbamoyl)formamido]butyl}phenyl)propoxy]acetamido}benzoic acid Step 1

50 mg (0.14 mmol) 2-[3-(2-{4-[(Methylcarbamoyl)formamido]butyl}phenyl)propoxy]acetic acid (BB-6, IK-0358/6), 32.8 mg (0.17 mmol) EDCl and 43.1 mg (0.29 mmol) Methyl 4-aminobenzoate were dissolved in 3 ml DCM and stirred at rt for 1.5 h (clear solution).

The mixture was evaporated to dryness and purified via pTLC (1 mm, EA/PE 4:1, R f of possible product: 0.31)

Step 2

To a solution of 48 mg (0.10 mmol) N-Methyl-N'-{4-[2-(3-{[(pyridin-2-yl)carbamoyl]methoxy}propyl)phenyl]butyl}ethanediamide (GH-0498/1) in 2 ml THF 16.7 mg (0.40 mmol) LiOH monohydrate dissolved in 0.5 ml water were added and the mixture was stirred at rt over night (a biphasic mixture).

The mixture was poured into 1 N HCl solution (10 ml) and extracted with DCM (3×20 ml). The combined organic layers were dried over $Na_2SO_4$ and concentrated to dryness. The crude product was purified via pTLC (DCM/MeOH/FA 100:10:1, $R_f$ of possible product: 0.43).

Yield: 10 mg (21%), white solid.
Compound 25 (Comp-25)

N'-[(5Z)-13-[2-(4-hydroxy-2-oxo-2,5-dihydrofuran-3-yl)-2-oxoethoxy]tridec-5-en-1-yl]-Nmethylethanediamide 2-{[(8Z)-13-[(methylcarbamoyl)formamido]tridec-8-en-1-yl]oxy}acetic acid (BB-4, 50 mg), DCC (34.7 mg), DMAP (22.3 mg) and 2,4 (3H,5H)-Furandione (15.4 mg) were placed in a G16 vial. $CH_2Cl_2$ (3.00 mL) was added and the resulting mixture was stirred at r.t. for 18 h. Control by LC/MS showed product.

The reaction mixture was diluted with water (30 mL) and extracted with $CH_2C_2$ (3×20 mL). The combined organic layers were washed with brine (10 mL), dried over $Na_2SO_4$ and concentrated in vacuo. The residue was purified by preparative TLC ($CH_2Cl_2$/MeOH=9:1).

Yield: 20 mg (33%), beige solid.
Compound 26 (Comp-26)

N'-[4-(2-(3-[2-(hydroxymethyl) phenoxyl]propyl) phenyl) butyl]-N-methylethanediamide Step 1

Salicylaldehyde (2.00 g) and imidazole (2.79 g) were dissolved in DMF (20.0 mL). TIPSCl (5.96 mL) was added and the resulting mixture was stirred at 60° C. for 2 d. Control by TLC (PE/EtOAc=95:5) and LC/MS showed incomplete conversion. Additional TIPSCl (2.00 mL) was added and stirring was continued at 60° C. for 3 d. Control by TLC (PE/EtOAc=95:5) and LC/MS showed almost complete conversion. The reaction mixture was diluted with water (100 mL) and extracted with MTBE (3×40 mL). The combined organic layers were washed with 1N NaOH (30 mL) and brine (20 mL), dried over $Na_2SO_4$ and concentrated in vacuo. The residue was purified by column chromatography on $SiO_2$ (PE/EtOAc=95:5).

Yield: 3.54 g (78%) pale yellow liquid

Step 2

2-{[tris(propan-2-yl)silyl]oxy}benzaldehyde (3.54 g) was dissolved in EtOH (30.0 mL) and cooled to 0° C. NaBH4 (481 mg) was added and the resulting mixture was stirred at 0° C. for 30 min and then at r.t. for 18 h. Control by TLC (PE/EtOAc=8:2) and LC/MS showed product. The reaction mixture was diluted with water (100 mL) and extracted with EtOAc (3×40 mL). The combined organic layers were washed with brine (30 mL), dried over $Na_2SO_4$ and concentrated in vacuo. The residue was purified by column chromatography on $SiO_2$ (PE/EtOAc=8:2).

Yield: 2.73 g (77%) yellow oil

Step 3

(2-{[tris(propan-2-yl)silyl]oxy}phenyl)methanol (400 mg) was dissolved in dry THF (15 mL). NaH (60% in mineral oil, 85.6 mg) was added and the mixture stirred at r.t. for 15 min. Allylbromide (309 µL) was then added and the resulting mixture was stirred at r.t. over night. Control by LC/MS showed product. The reaction mixture was diluted with water (50 mL) and extracted with $CH_2Cl_2$ (3×30 mL). The combined organic layers were washed with brine (20 mL), dried over $Na_2SO_4$ and concentrated in vacuo. The so obtained crude product was used for further transformation as such.

Yield: 480 mg (crude) yellow oil

Step 4

{2-[(prop-2-en-1-yloxy)methyl]phenoxy}tris(propan-2-yl)silane (178 mg) was placed in a 10 mL flask and cooled to 0° C. under and Ar-atmosphere. 9-BBN (0.5 M in THF, 1.38 mL) was then added dropwise and the resulting mixture was stirred at 0° C. for 30 min and then at r.t. for 2 h. A solution of Na2CO3 (147 mg) in water (1.50 mL) was then added and stirring was continued at r.t. for 30 min. Then N'-[4-(2-iodophenyl)butyl]-N-methylethanediamide (BB-2, 100 mg) and PdCl2(PPh3)$_2$ (9.7 mg) were added and the mixture heated to 50° C. for 3 h. Control by LC/MS showed product. The reaction mixture was cooled to r.t., diluted with water (20 mL) and the layers were separated. The aqueous layer was extracted with EtOAc (15 mL). The combined organic layers were washed with brine (10 mL), dried over Na2SO4 and concentrated in vacuo. The residue was passed through a short column of $SiO_2$ (PE/EtOAc 1:1). The still crude product was then used for further transformation as such.

Yield: 235 mg (crude) yellow oil.

Step 5

N-methyl-N'-[4-(2-{3-[(2-{[tris(propan-2-yl)silyl]oxy}phenyl)methoxy]propyl}phenyl)butyl]ethanediamide (154 mg, crude IK-0357/19) was dissolved in THF (5.00 mL). TBAF*3H2O (87.0 mg) was added and the resulting mixture was stirred at r.t. for 30 min. Control by LC/MS showed complete conversion. The reaction mixture was poured into water (20 mL) and extracted with EtOAc (3×10 mL). The combined organic layers were washed with brine (10 mL), dried over Na2SO4 and concentrated in vacuo. The residue was purified by preparative TLC (CH$_2$Cl$_2$/MeOH=95:5).

Yield: 75 mg (66%) white solid.
Compound 27 (Comp-27)

N'-[(5Z)-13-(2-hydroxyphenoxy)tridec-5-en-1-yl]-Nmethylethanediamide

Step 1

N'-[(5Z)-13-hydroxytridec-5-en-1-yl]-N-methylethanediamide (BB-8, 400 mg) was suspended in CH$_2$Cl$_2$ (20 mL). PPh 3 (598 mg) and CBr4 (756 mg) were added and the resulting mixture was stirred at r.t. for 1.5 h. Control by TLC (PE/EtOAc=1:1) and LC/MS showed complete conversion.

The reaction mixture was concentrated in vacuo and the residue was purified by preparative TLC (PE/EtOAc=1:1).

Step 2

N'-[(5Z)-13-bromotridec-5-en-1-yl]-N-methylethanediamide (50 mg), pyrocatechol (76.2 mg) and K$_2$CO$_3$ (57.4 mg) were placed in a G16 vial. DMF (3.00 mL) was added and the resulting mixture was stirred at 60° C. for 2.5 h. Control by LC/MS showed product.

The reaction mixture was diluted with water (40 mL) and extracted with MTBE (3×20 mL). The combined organic layers were washed with water (20 mL) and brine (10 mL), dried over Na$_2$SO$_4$ and concentrated in vacuo. The residue was purified by preparative TLC (CH$_2$Cl$_2$/MeOH=95:5).

Yield: 43 mg (80%), white solid.
Compound 28 (Comp-28)

N-Methyl-N'-[4-(2-{3-[2-(morpholin-4-yl)-2-oxoethoxy]propyl}phenyl)butyl] ethanediamide 50 mg (0.14 mmol) 2-[3-(2-{4-[(Methylcarbamoyl)formamido]butyl}phenyl)propoxy]acetic acid (BB-8, IK-0358/6), 32.8 mg (0.17 mmol) EDCl and 24.9 mg (0.29 mmol, 24.9 µl) morpholine were dissolved in 3 ml DCM and stirred at rt over the weekend (clear solution).

The mixture was evaporated to dryness and purified via pTLC (1 mm, DCM/MeOH 10:1, R$_f$ of possible product: 0.48).

Yield: 34 mg (58%), white solid.
Compound 29 (Comp-29)

N'-(4-{2-[3-(3-hydroxyphenoxy)propyl]phenyl}butyl)-Nmethylethanediamide

Step 1

N'-{4-[2-(3-hydroxypropyl)phenyl]butyl}-N-methylethanediamide (BB-9, 400 mg) was suspended in CH$_2$Cl$_2$ (20 mL). PPh$_3$ (610 mg) and CBr4 (771 mg) were added and the resulting mixture was stirred at r.t. for 30 min. Control by TLC (PE/EtOAc=1:1) and LC/MS showed complete conversion. The reaction mixture was concentrated in vacuo and the residue was purified by preparative TLC (PE/EtOAc=1:1).

Step 2

N'-{4-[2-(3-bromopropyl)phenyl]butyl}-N-methylethanediamide (50 mg), 1,3-Benzenediol (77.5 mg) and K$_2$CO$_3$ (58.4 mg) were placed in a G16 vial. DMF (3.00 mL) was added and the resulting mixture was stirred at 60° C. for 1 h. Control by LC/MS showed product.

The reaction mixture was diluted with water (40 mL) and extracted with MTBE (3×20 mL). The combined organic layers were washed with water (20 mL) and brine (10 mL), dried over Na$_2$SO$_4$ and concentrated in vacuo. The residue was purified by preparative TLC (CH$_2$Cl$_2$/MeOH=95:5).

Yield: 40 mg (74%), white solid.
Compound 30 (Comp-30)

N'-[(5Z)-13-(4-hydroxyphenoxy)tridec-5-en-1-yl]-Nmethylethanediamide

Step 1

N'-[(5Z)-13-hydroxytridec-5-en-1-yl]-N-methylethanediamide (BB-8, 400 mg) was suspended in CH 2C$_{12}$ (20 mL). PPh 3 (598 mg) and CBr4 (756 mg) were added and the resulting mixture was stirred at r.t. for 1.5 h. Control by TLC (PE/EtOAc=1:1) and LC/MS showed complete conversion.

The reaction mixture was concentrated in vacuo and the residue was purified by preparative TLC (PE/EtOAc=1:1).

Step 2

N'-[(5Z)-13-bromotridec-5-en-1-yl]-N-methylethanediamide (50 mg), hydroquinone (76.2 mg) and K$_2$CO$_3$ (57.4 mg) were placed in a G16 vial. DMF (3.00 mL) was added and the resulting mixture was stirred at 60° C. for 2.5 h. Control by LC/MS showed product.

The reaction mixture was diluted with water (40 mL) and extracted with MTBE (3×20 mL). The combined organic layers were washed with water (20 mL) and brine (10 mL), dried over Na$_2$SO$_4$ and concentrated in vacuo. The residue was purified by preparative TLC (CH$_2$Cl$_2$/MeOH=95:5).

Yield: 43 mg (80%), white solid
Compound 31 (Comp-31)

N'-(4-{2-[3-(4-hydroxyphenoxy)propyl]phenyl}butyl)-Nmethylethanediamide

Step 1

N'-{4-[2-(3-hydroxypropyl)phenyl]butyl}-N-methylethanediamide (BB-9, 400 mg) was suspended in CH2Cl2 (20 mL). PPh3 (610 mg) and CBr$_4$ (771 mg) were added and the resulting mixture was stirred at r.t. for 30 min. Control by TLC (PE/EtOAc=1:1) and LC/MS showed complete conversion.

The reaction mixture was concentrated in vacuo and the residue was purified by preparative TLC (PE/EtOAc=1:1).

Step 2

N'-{4-[2-(3-bromopropyl)phenyl]butyl}-N-methylethanediamide (50 mg), Hydroquinone (77.5 mg) and K$_2$CO$_3$ (58.4 mg) were placed in a G16 vial. DMF (3.00 mL) was added and the resulting mixture was stirred at 60° C. for 1 h. Control by LC/MS showed product.

The reaction mixture was diluted with water (40 mL) and extracted with MTBE (3×20 mL). The combined organic layers were washed with water (20 mL) and brine (10 mL), dried over Na$_2$SO$_4$ and concentrated in vacuo. The residue was purified by preparative TLC (CH$_2$Cl$_2$/MeOH=95:5).

Yield: 39 mg (72%), white solid
Compound 3" (Comp-3")

N'-[4-(2-{3-[(4-hydroxyphenyl)methoxy]propyl}phenyl)butyl]-N-methylethanediamide Step 1

4-Hydroxybenzaldehyde (2.00 g) and imidazole (2.79 g) were dissolved in DMF (20.0 mL). TIPSCl (5.96 mL) was added and the resulting mixture was stirred at 60° C. for 2 d.
Control by TLC (PE/EtOAc=95:5) and LC/MS showed complete conversion.
The reaction mixture was diluted with water (100 mL) and extracted with MTBE (3×40 mL). The combined organic layers were washed with 1N NaOH (30 mL) and brine (20 mL), dried over $Na_2SO_4$ and concentrated in vacuo. The residue was purified by column chromatography on $SiO_2$ (PE/EtOAc=95:5).
Yield: 3.94 g (86%) pale yellow oil Step 2

4-{[tris(propan-2-yl)silyl]oxy}benzaldehyde (3.94 g) was dissolved in EtOH (30.0 mL) and cooled to 0° C. NaBH4 (535 mg) was added and the resulting mixture was stirred at 0° C. for 30 min and then at r.t. for 18 h.
Control by TLC (PE/EtOAc=8:2) and LC/MS showed product.
The reaction mixture was diluted with water (100 mL) and extracted with EtOAc (3×40 mL). The combined organic layers were washed with brine (30 mL), dried over $Na_2SO_4$ and concentrated in vacuo. The residue was purified by column chromatography on $SiO_2$ (PE/EtOAc=8:2).

Step 3

(4-{[tris(propan-2-yl)silyl]oxy}phenyl)methanol (300 mg) was dissolved in dry THF (5.00 mL). NaH (60% in mineral oil, 64.2 mg) was added and the mixture stirred at r.t. for 15 min. Allylbromide (231 µL) was then added and the resulting mixture was stirred at r.t. for 2.5 h. Control by LC/MS showed complete conversion.
The reaction mixture was poured into water (30 mL) and extracted with EtOAc (3×10 mL). The combined organic layers were washed with brine, dried over $Na_2SO_4$ and concentrated in vacuo. The residue was used for further transformation as such.
Yield: 372 mg (crude) yellow oil Step 4

{4-[(prop-2-en-1-yloxy)methyl]phenoxy}tris(propan-2-yl)silane (356 mg) was placed in a 10 mL flask and cooled to 0° C. under and Ar-atmosphere. 9-BBN (0.5 M in THF, 3.33 mL) was then added dropwise and the resulting mixture was stirred at 0° C. for 30 min and then at r.t. for 2 h.
A solution of $Na_2CO_3$ (147 mg) in water (3.00 mL) was then added and stirring was continued at r.t. for 30 min. Then N'-[4-(2-iodophenyl)butyl]-N-methylethanediamide (BB-2, 100 mg) and $PdCl_2(PPh_3)_2$ (9.7 mg) were added and the mixture heated to 50° C. for 2 h. Control by LC/MS showed product. The reaction mixture was cooled to r.t., diluted with water (20 mL) and the layers were separated. The aqueous layer was extracted with EtOAc (15 mL). The combined organic layers were washed with brine (10 mL), dried over Na2SO4 and concentrated in vacuo. The residue was passed through a short column of $SiO_2$ (PE/EtOAc 1:1). The still crude product was then used for further transformation as such.
Yield: 248 mg (crude) yellow oil.

Step 5

N-methyl-N'-[4-(2-{3-[(4-{[tris(propan-2-yl)silyl]oxy}phenyl)methoxy]propyl}phenyl)butylethane-diamide (154 mg, crude IK-0357/20) was dissolved in THF (5.00 mL). TBAF*3H2O (131 mg) was added and the resulting mixture was stirred at r.t. for 30 min. Control by LC/MS showed complete conversion.
The reaction mixture was poured into water (40 mL) and extracted with EtOAc (3×20 mL). The combined organic layers were washed with brine (10 m, dried over $Na_2SO_4$ and concentrated in vacuo. The residue was purified by preparative TLC ($CH_2Cl_2$/MeOH=95:5).
Yield: 76 mg (68%), white solid.

TABLE 1

Calculated exact mass of Comp-14 to Comp-32

| Compound IUPAC name | Comp-00 | Calculated exact mass | M + 1 |
|---|---|---|---|
| N-methyl-N'-[(5Z)-13-[(1H-1,2,3,4-tetrazol-5-yl)methoxy]tridec-5-en-1-yl]ethanediamide | Comp-14 | 380.25359 | 381.260869 |
| N'-(4-{2-[3-(Carbamoylmethoxy)propyl]phenyl}butyl)-N-methylethanediamide | Comp-15 | 349.20016 | 350.207437 |
| N-Methyl-N'-[(5Z)-13-[(5-oxo-4,5-dihydro-1H-1,2,4-triazol-3-yl)methoxy]tridec-5-en-1-yl]ethanediamide | Comp-16 | 395.25326 | 396.260535 |
| N-methyl-N'-[(5Z)-13-[(phenylcarbamoyl)methoxy]tridec-5-en-1-yl]ethanediamide | Comp-17 | 431.27841 | 432.285687 |
| N-methyl-N'-[(5Z)-13-{[(oxan-4-yl)carbamoyl]methoxy}tridec-5-en-1-yl]ethanediamide | Comp-18 | 439.30462 | 440.311902 |
| N-methyl-N'-[(5Z)-13-{[(1,3-oxazol-2-yl)carbamoyl]methoxy}tridec-5-en-1-yl]ethanediamide | Comp-19 | 422.25292 | 423.260201 |
| N'-[(5Z)-13-{[(4-methoxyphenyl)carbamoyl]methoxy}tridec-5-en-1-yl]-N-methylethanediamide | Comp-20 | 461.28897 | 462.296252 |
| N-Methyl-N'-[4-(2-{3-[(phenylcarbamoyl)methoxy]propyl}phenyl)butyl]ethanediamide | Comp-21 | 425.23146 | 426.238737 |
| N-Methyl-N'-[4-(2-{3-[2-oxo-2-(pyrrolidin-1-yl)ethoxy]propyl}phenyl)butyl]ethanediamide | Comp-22 | 403.24711 | 404.254387 |
| N-Methyl-N'-[4-(2-{3-(2-(morpholin-4-yl)-2-oxoethoxy]propyl}phenyl)butyl]ethanediamide | Comp-23 | 419.24202 | 420.249302 |

TABLE 1-continued

Calculated exact mass of Comp-14 to Comp-32

| Compound IUPAC name | Comp-00 | Calculated exact mass | M + 1 |
|---|---|---|---|
| 4-{2-[3-(2-{4-[(methylcarbamoyl)formamido]butyl}phenyl)propoxy]acetamido}benzoic acid | Comp-24 | 469.22129 | 470.228567 |
| N'-[(5Z)-13-[2-(4-hydroxy-2-oxo-2,5-dihydrofuran-3-yl)-2-oxoethoxy]tridec-5-en-1-yl]-N-methylethanediamide | Comp-25 | 438.2366 | 439.243883 |
| N'-[4-(2-{3-[2-(hydroxymethyl)phenoxy]propyl}phenyl)butyl]-N-methylethanediamide | Comp-26 | 398.22056 | 399.227838 |
| N'-[(5Z)-13-(2-hydroxyphenoxy)tridec-5-en-1-yl]-N-methylethanediamide | Comp-27 | 390.25186 | 391.259138 |
| N'-[(5Z)-13-(3-hydroxyphenoxy)tridec-5-en-1-yl]-N-methylethanediamide | Comp-28 | 390.25186 | 391.259138 |
| N'-(4-{2-[(3-(3-hydroxyphenoxy)propyl]phenyl}butyl)-N-methylethanediamide | Comp-29 | 384.20491 | 385.212188 |
| N'-[(5Z)-13-(4-hydroxyphenoxy)tridec-5-en-1-yl]-N-methylethanediamide | Comp-30 | 390.25186 | 391.259138 |
| N'-(4-{2-[3-(4-hydroxyphenoxy)propyl]phenyl}butyl)-N-methylethanediamide | Comp-31 | 384.20491 | 385.212188 |
| N'-[4-(2-{3-[(4-hydroxyphenyl)methoxy]propyl}phenyl)butyl]-N-methylethanediamide | Comp-32 | 398.22056 | 399.227838 |

EXAMPLE 2: EFFICACY OF COMPOUND 1 IN A LASER INDUCED CHOROIDAL NEOVASCULARIZATION MODEL IN RAT EVALUATED BY MEASURING VASCULAR LEAKAGE USING FLUORESCENCE ANGIOGRAPHY

The laser induced CNV model in rat is a widely used model to prove the therapeutic efficacy of drugs for treatment of several ocular diseases characterized by angiogenesis and inflammation in the eye such as wet age-related macular degeneration (AMD). In this model a focused laser burn in the layer of Bruch's membrane causes a disruption of this membrane, a local injury, followed by inflammation and growth of new blood vessels. These newly formed blood vessels are typically leaky. This leakage is measured by extravasation of a fluorescent dye in the back of the eye (Fluorescein) and is a well-accepted marker for vascular leakage which is proportionally to the amount of newly grown blood vessels. This method is also the state of the art procedure in the clinical practice in man.

All standard operating procedures and protocols described in this study plan have been reviewed by Ethics Committee. All animals have been treated according to the Directive 2010/63/UE European Convention for the Protection of Vertebrate Animals used for Experimental and Other Scientific Purposes and to the Association for Research in Vision and Ophthalmology (ARVO) Statement for the Use of Animals in Ophthalmic and Vision Research.

Animals: Brown Norway rats at the age of 8-10 weeks at the day of induction.

Induction of neovascularization: Animals have been anesthetized by an intramuscular injection of a mix xylazine and ketamine. Right eye pupils have been dilated by instillation of one drop of 0.5% tropicamide before handling. Six burns on anesthetized animals have been created in the right eye by applying 170-180 mW of 532-nm laser light (Viridis laser, Quantel, France) on 75-μm spots around the optic nerve, between the main retinal vessel branches, for 0.1 s, through the slit lamp and a contact lens. Production of a bubble at the time of laser application confirmed the rupture of Bruch's membrane.

Treatment: For vehicle control group on Day 0, just after induction of neovascularization, vehicle was intravitreally injected (5 μL) in right eyes under an operating microscope using a 30-G-needle mounted on a 100 μL Hamilton syringe. The administrations have been made on anesthetized animals (same anesthesia than for neovascularization induction). In the first treatment group Compound 1, which has a structure as indicated in formula (VI) was intraperitoneally administrated (100 μL/100 g), once daily from Day 0 (3 hours±15 min prior induction) to Day 23. In another treatment group Compound 1 was orally administrated via gavage (1 mL/100 g), twice daily from Day 0 (3 hours±15 min prior induction) to Day 22 (q7 h±30 min).

Fluorescein angiography: Fluorescein angiography has been performed in the lasered right eyes on Days 14 and 21 using Heidelberg Retinal Angiograph (HRA). After anesthesia (see above), 250 μL/100 g body weight of a 10% sodium fluorescein will be injected subcutaneously, and fluorescence photos will be recorded 10 minutes after dye injection. For the evaluation by fluorescein angiography the leakage of fluorescein will be evaluated in the angiograms by two independent examiners masked to the study groups and graded as follows: Score 0: no leakage; Score 1: slightly stained; Score 2: moderately stained; Score 3: strongly stained.

In-life phase termination: At the end of the study on Day 23, all animals will be anesthetized (see above) then euthanized using an overdosed intracardiac injection of pentobarbital. This method is among the recommended methods by the European Authorities.

Statistical analysis: The statistical analyses have been performed using the software Prism. A Kruskal-Wallis analysis has been performed and the drug effect has been assessed using the Dunett's test for multiple comparisons; each treated group has been compared to that of the vehicle at each time-point. The p values lower than 0.05 will be significant.

Results are shown in FIG. 1.

EXAMPLE 3: COMP-02 DISTRIBUTION AFTER ORAL, TOPICAL OR INTRAVITREAL ADMINISTRATION IN DIFFERENT COMPARTMENTS OF THE RABBIT EYE

This example shows that highest ocular exposures of Comp-02 in the posterior eye are reached after intravitreal injection.

Materials and Methods

Study design: To gain insight into the distribution behaviour of synthetic 17,18-EEQ-agonists, ocular pharmacokinetic studies were performed in pigmented HY79b rabbits. Briefly, 15 male rabbits per administration route were anesthetized at the time-points for sampling indicated in tables 2-4 by an intramuscular injection of a mixed solution of xylazine and ketamine. Blood collection was performed by cardiac puncture in $K_3EDTA$ tubes and centrifuged at 2000 g, 10 min at 4° C. Approximately 3 mL of plasma were sampled, put in plastic tubes, snap frozen in liquid nitrogen and stored at −80° C. until assay. Then animals were euthanized by intracardiac injection of overdosed pentobarbital. This method is one of the recommended methods for euthanasia by the European authorities (*French decree No. 2013-118, dated Feb. 1, 2013 publishing the European directive 2010/63/UE. J.Offic. Rp. Fr.* 2013; *Text* 24 *out of* 130). Immediately after euthanasia, samples from both eyes were quickly and carefully taken, put in plastic tubes, weighed, snap frozen in liquid nitrogen and stored at −80° C. until assay. Content of Comp-02 was determined in ocular samples and plasma following an established RRLCMS/MS method. The results are presented in Tables 5-7 and are expressed as mean values for the different pharmacokinetic parameters. Chromatogram integration was done using MassHunter software. Apparent Cmax and Tmax, T½, AUC1-48 h were calculated by Excel® software. Concentrations were expressed in ng/g or ng/mL of tissue/eye compartment.

Results

After oral administration Comp-02 was below lower limit of detection (0.1 ng/10 µl injected) in both aqueous humor (except for one out of 15 animals) and retina (except for two out of 15 animals) samples. However, oral administration of Comp-02 reached effective dose level (246 ng/g) 1 h after administration of 2 mg/kg (0.2 mg/mL) in choroid tissue as well as considerable plasma level (1213 ng/mL, 1 h after administration). Corresponding to the maximal level considerable exposures were only seen in choroid and plasma ($AUC_{1\text{-}48\ hrs}$ (ng*h/mL): 1387 and 6331).

For topical administration it was found, that the Comp-02 formulation was macroscopically very well tolerated, as checked by ophthalmoscopy. Table 6 shows, besides generally very low level, that highest dose level were seen in aqueous humor (88 ng/mL 1 h post-administration), followed by the choroid (79 ng/g 1 h post-administration). Both in the retina and in plasma only low level were reached (24 ng/g 1 h post-administration and 31 ng/mL 0.5 h post-administration, respectively). $AUC_{1\text{-}48\ hrs}$ values were low after topical administration in all tested ocular tissues ($AUC_{1\text{-}48\ hrs}$ (ng*h/mL): 324 for aqueous humor, 117 for choroid and 21 for retina) as well as in plasma (262 ng*h/mL).

Also for intravitreal injection it was found, that the Comp-02 formulation was macroscopically very well tolerated, as checked by ocular examination with a slit lamp. Table 6 shows, that considerable Comp-02 level were found in all tissues of the eye and in plasma. Highest level were found in the choroid (14957 ng/g 1 h post-injection) followed by retina and vitreous (10052 ng/g and 6647 ng/mL 1 h post-injection). Exposures were >55000 ($AUC_{1\text{-}48\ hrs}$ (ng*h/mL): 55401 for vitreous, 63283 for choroid and 79866 for retina) except for plasma (287 ng*h/mL)).

In summary, the highest ocular exposures of Comp-02 in the posterior eye were reached after intravitreal injection compared to oral and topical administration.

TABLE 2

Study design for oral administration

| Group | Formulation | Administration | Time-points for sampling | Animal number |
|---|---|---|---|---|
| 1 | Comp-02 in | T0 h: | 1 h ± 6 min | 1, 2, 3 |
| 2 | isotonic salt | Single oral | 4 h ± 24 min | 4, 5, 6 |
| 3 | solution | administration | 8 h ± 48 min | 7, 8, 9 |
| 4 | | 2 mg/kg, | 24 h ± 144 min | 10, 11, 12 |
| 5 | | 0.2 mg/mL | 48 h ± 288 min | 13, 14, 15 |

TABLE 3

Study design for topical administration

| Group | Formulation | Administration | Time-points for sampling | Animal number |
|---|---|---|---|---|
| 1 | Comp-02 in | T0 h: Single | 30 min ± 3 min | 1, 2, 3 |
| 2 | isotonic salt | instillation | 1 h ± 6 min | 4, 5, 6 |
| 3 | solution | 50 µl (1 mg/mL) | 2 h ± 12 min | 7, 8, 9 |
| 4 | | in both eyes | 4 h ± 24 min | 10, 11, 12 |
| 5 | | | 24 h ± 144 min | 13, 14, 15 |

TABLE 4

Study design for intravitreal administration

| Group | Formulation | Administration | Time-points for sampling | Animal number |
|---|---|---|---|---|
| 1 | Comp-02 in | T0 h: | 1 h ± 6 min | 1, 2, 3 |
| 2 | isotonic salt | Single vitreal | 2 h ± 12 min | 4, 5, 6 |
| 3 | solution | injection of 50 µl | 8 h ± 48 min | 7, 8, 9 |
| 4 | | (1 mg/mL) in both | 24 h ± 144 min | 10, 11, 12 |
| 5 | | eyes | 48 h ± 288 min | 13, 14, 15 |

TABLE 5

Pharmacokinetic parameters in ocular tissue and plasma after oral administration

| | Aqueous humor | Retina | Choroid | Plasma |
|---|---|---|---|---|
| $C_{max}$ | 8 | 15 | 246 | 1213 |
| $T_{max}$ | 1 | 4 | 1 | 1 |
| $t_{1/2}$ | NA | NA | 9 | 6 |
| $AUC_{1\text{-}48\ hours}$ | 12 | 64 | 1387 | 6331 |

$C_{max}$ = the highest mean value measured (ng/g or mL of tissue)
$T_{max}$ = time-point when the highest mean value is measured (hours)
AUC time 1 to time 2 = area under the curve in ng/g or mL of tissue
$t_{1/2}$ = ln(2)/(-a) with a = slope of ln (concentration) = f(t)
$t_{1/2}$ = calculated from the Tmax value
NA = Not applicable, insufficient data available

TABLE 6

Pharmacokinetic parameters in ocular tissue and plasma after topical administration

| | Aqueous humor | Retina | Choroid | Plasma |
|---|---|---|---|---|
| $C_{max}$ | 88 | 24 | 79 | 31 |
| $T_{max}$ | 1 | 1 | 1 | 0.5 |
| $t_{1/2}$ | 1 | NA | 0.7 | 5.4 |
| $AUC_{1\text{-}48\ hours}$ | 324 | 21 | 117 | 262 |

$C_{max}$ = the highest mean value measured (ng/g or mL of tissue)
$T_{max}$ = time-point when the highest mean value is measured (hours)
AUC time 1 to time 2 = area under the curve in ng/g or mL of tissue
$t_{1/2}$ = ln(2)/(-a) with a = slope of ln (concentration) = f(t)
$t_{1/2}$ = calculated from the Tmax value
NA = Not applicable, insufficient data available

TABLE 7

Pharmacokinetic parameters in ocular tissue and plasma after intravitreal injection

|  | Vitreous | Retina | Choroid | Plasma |
|---|---|---|---|---|
| $C_{max}$ | 6647 | 10052 | 14957 | 19 |
| $T_{max}$ | 1 | 1 | 1 | 2 |
| $t_{1/2}$ | 4.6 | 2.6 | 2.4 | 4.2 |
| $AUC_{1\text{-}48\ hours}$ | 55401 | 79866 | 63283 | 287 |

$C_{max}$ = the highest mean value measured (ng/g or mL of tissue)
$T_{max}$ = time-point when the highest mean value is measured (hours)
AUC time 1 to time 2 = area under the curve in ng/g or mL of tissue
$t_{1/2}$ = ln(2)/(-a) with a = slope of ln (concentration) = f(t)
$t_{1/2}$ = calculated from the Tmax value
NA = Not applicable, insufficient data available

EXAMPLE 4: ANTI-INFLAMMATORY EFFECT OF A METABOLICALLY ROBUST ANALOG OF 17,18-EEQ (COMP-02) ON HL-1 CARDIOMYOCYTES

Materials and Methods

In order to investigate the anti-inflammatory potential of compounds being part of the invention in vitro, a cardiomyocyte cell line was used (mouse derived immortalized cardiomyocytes, HL-1 cells). Cells were either treated with vehicle (0.01% ethanol) or different concentrations of test compound (Comp-02: $c_E$=10 nM, 100 nM or 1 µM). Simultaneously, the cells were challenged with 1 µg/mL lipopolysaccharide (LPS). After 24 h of incubation, the cells were processed to measure viability (FIG. 2) and release of the pro-inflammatory cytokine TNF alpha (FIG. 3).

Results

The results are presented in FIG. 2 and FIG. 3. The inflammatory stimulus LPS leads to a significant reduction in cell viability. This cytotoxic effect was dose-dependently reversed by Comp-02, FIG. 2. Moreover, LPS-incubation significantly induced the production of the pro-inflammatory cytokine TNF alpha (FIG. 3). Comp-02 alone did not have an influence on TNF alpha production. LPS-induced TNF alpha release from the HL-1 cells was significantly and dose-dependently reduced by Comp-02 (FIG. 3).

EXAMPLE 5: INHIBITORY EFFECT OF A METABOLICALLY ROBUST ANALOG OF 17,18-EEQ (COMP-02) ON RENAL AND CARDIAC INFLAMMATION IN A RAT MODEL OF SEVERE HYPERTENSION AND END-ORGAN DAMAGE

Materials and Methods

The aim of this study was to assess and compare the effect of continuous oral treatment of a metabolically robust analog of 17,18-EEQ (Comp-02) or vehicle (isotonic salt solution) on physiological parameters, clinical chemistry and end-organ damage in male double transgenic rats (dTGR). Non-treated Sprague-Dawley rats (SD) of same genetic background were used as control. Double transgenic rats, overexpressing the human renin and angiotensinogen genes, develop severe hypertension and are a model for Ang-II induced end-organ damage with cardiac hypertrophy and kidney failure. Moreover, the dTGR model features severe atrial hypertension, cardiac hypertrophy and nephrosclerosis with marked fibrosis and inflammation.

Before start of the experiment the animals were randomly assigned to either compound or vehicle treatment. Prior to the experiment chow was changed to an omega-6 rich chow for all treatment groups as well as the SD-control animals. dTGR compound treated animals were dosed twice daily with 1.33 mg/kg for 21 days by gavage. Comp-02 was prepared in 61.6 ppm Na2CO3 and 0.9% NaCl ready to use solution for application, while dTGR animals were dosed twice daily with 0.9% NaCl ready to use solution for vehicle control. The application volume was 5.0 mL/kg b.w. After 21 days of treatment, at the age of seven weeks, animals were sacrificed through heart removal under pentobarbital anaesthesia (20 mg/kg b.w., heparin 500 I.E./mL) and blood and organs were harvested. Heart and kidney were removed and weighed. Heart and kidney were divided and snap frozen in liquid nitrogen for molecular biology analyses, frozen in −40° C. isopentane and stored at −80° C. for cryoslides. Frozen kidneys and hearts embedded in TissueTek were cryosectioned to 5 m thickness. Cryo sections were fixed with ice-cold acetone, washed with PBS and blocked with normal donkey serum at room temperature. Afterwards sections were incubated in a dark humid chamber over night at 4° C. with primary monoclonal antibody mouse anti-ED1(cD68) (AbD serotec). After washing with PSB slides were incubated with secondary antibody donkey anti-mouse (Cy3) for 90 minutes in a dark humid chamber at room temperature followed by mounting with vectashield. Samples were analysed using a Zeiss Axioplan-2 imaging microscope with the digital image-processing program AxioVision 4.8. All evaluations were done by a single blinded investigator. Analysis of infiltrating macrophages was done by enumerating ED1 positive cells in heart (ventricle) and kidney tissue (outer medulla and cortex) sections. Data were expressed as sum of 20 randomly chosen view fields, non-overlapping fields per section.

Statistical analyses were performed with software R for immunohistochemistry. As the data are nonparametric (counts) Kruskall-Wallis-tests were applied for overall group differences while pairwise U-tests with FDR correction were used to analyze differences between individual groups. P-values below 0.05 were considered significant.

Results

FIG. 4 and FIG. 5 show the potential of a robust analog of 17,18-EEQ (Comp-02) to modulate inflammation in dTGR animals. This was measured both in heart (FIG. 4) and kidney (FIG. 5) with macrophages infiltration via ED1 staining as a marker for inflammation. The values shown are expressed as median with interquartile range. Count values are pooled in bins of 20 view fields. The results show that dTGR animals have significant higher amounts of infiltrated macrophages in the cardiac or renal tissue compared to non-treated SD animals (FIG. 4 and FIG. 5). However, Comp-02 treatment led to a significant reduction of macrophage infiltration (ED1 positive cells) in dTGR animals compared to vehicle treated dTGRs.

The invention claimed is:
1. A method of treating a disorder associated with neovascularization and/or inflammation in a subject, the method comprising: administering to the subject in need thereof an effective amount of a compound of formula (V):

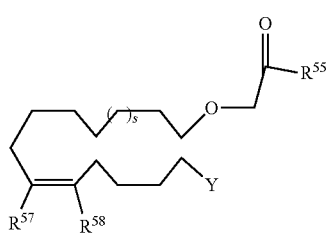

formula (V)

wherein
R$^{55}$ represents —OH; —OR$^{22}$; or —(OCH$_2$—CH$_2$)$_i$—R$^{23}$;
R$^{22}$ is a hydrogen atom or a C$_1$-C$_6$alkyl group;
R$^{23}$ is —OH;
i is an integer of from 1 to 10;
Y represents a group selected from the group consisting of:

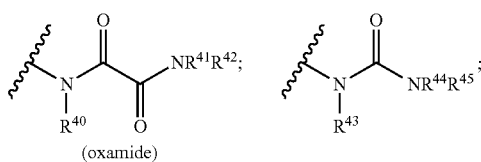

(oxamide)

R$^{40}$, R$^{41}$, R$^{43}$, and R$^{44}$ each independently represents a hydrogen atom or —C$_1$-C$_6$alkyl;
R$^{42}$ and R$^{45}$ each independently represents a —C$_1$-C$_3$alkyl;
R$^{57}$ and R$^{58}$ are hydrogen;
s is 0, 1 or 2; and
the double bond in formula (V) represents a double carbon-carbon bond in cis-configuration;
wherein the disorder is selected from age-related macular degeneration (AMD), vasculitis, nephritis, diabetic vasculopathy, diabetic nephropathy, diabetic retinopathy, ischemia reperfusion injury, renal fibrosis, tumor necrosis factor receptor associated periodic syndrome (TRAPS) and atherosclerosis.

2. The method according to claim 1, wherein
R$^{55}$ represents —OH or —(OCH$_2$—CH$_2$)$_i$—R$^{23}$; i is 2 to 4; and
Y is

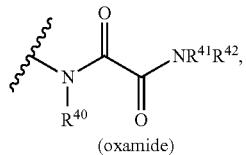

(oxamide)

wherein R$^{40}$ to R$^{42}$ are as defined in claim 1.

3. The method according to claim 1, wherein the compounds is of formula (VI)

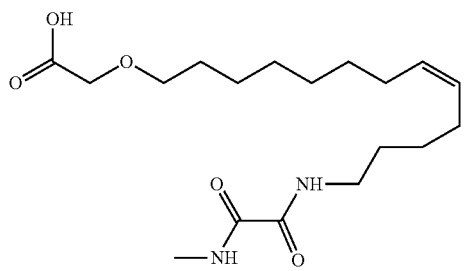

formula (VI)

or a pharmaceutically acceptable salt thereof.

4. The method according to claim 1, wherein the compound is administered orally, topically, subcutaneously, intramuscularly, intravenously, intranasally, intraocularly, or intraperitoneally.

5. The method according to claim 1, wherein the compound is a dosage form selected from the group consisting of a spray, an aerosol, a foam, an inhalant, a powder, a tablet, a capsule, a soft gelatin capsule, a tea, a syrup, a granule, a chewable tablet, a salve, a cream, a gel, a suppository, a lozenge, a liposome composition and a solution suitable for injection.

* * * * *